United States Patent [19]

Tamada et al.

[11] Patent Number: 5,071,856

[45] Date of Patent: Dec. 10, 1991

[54] CARBOSTYRIL DERIVATIVES AND SALTS THEREOF

[75] Inventors: Shigeharu Tamada; Takafumi Fujioka; Hidenori Ogawa; Shuji Teramoto; Kazumi Kondo, all of Tokushima, Japan

[73] Assignee: Otsuka Pharmaceutical Co., Ltd., Tokyo, Japan

[21] Appl. No.: 405,295

[22] Filed: Sep. 11, 1989

Related U.S. Application Data

[62] Division of Ser. No. 79,875, Jul. 30, 1987, Pat. No. 4,886,809.

[30] Foreign Application Priority Data

Jul. 31, 1986 [JP] Japan .................................. 61-181662
Jun. 24, 1987 [JP] Japan .................................. 62-156887

[51] Int. Cl.⁵ ..................... A61K 31/47; C07D 217/24
[52] U.S. Cl. .................................. 514/312; 544/121; 544/128; 544/363; 546/19; 546/115; 546/157; 546/158
[58] Field of Search .................. 546/157, 158; 514/312

[56] References Cited

FOREIGN PATENT DOCUMENTS

2,512,019 4/1983 France .
2,094,789 9/1982 United Kingdom .
2,071,094 9/1981 United Kingdom .

OTHER PUBLICATIONS

"Chemical Abstracts", vol. 98, 1983, col. 98:34510e.
"Chemical Abstracts", vol. 100, 1984, col. 100:51465w.
"Chemical Abstracts," vol. 100, 1984, col. 100:68187e.
Tominaga, et al., "Chemical Abstracts," vol. 108, 1988, col. 108:131551.

*Primary Examiner*—C. Warren Ivy
*Assistant Examiner*—James H. Turnipseed
*Attorney, Agent, or Firm*—Finnegan, Henderson, Farabow, Garrett & Dunner

[57] ABSTRACT

Novel carbostyril derivatives and salts thereof having useful pharmacological activities such as myocardial contraction increasing activity (positive inotropic activity), coronary blood flow increasing activity, hypotensive activity, activity for inhibiting vasoconstriction induced by norepinephrine, and anti-inflammatory effect in one hand, while they do not possess activity for increasing heart beat at all substantially as well as show quite low toxicity and low side-effects in central nervous system activities.

6 Claims, No Drawings

CARBOSTYRIL DERIVATIVES AND SALTS THEREOF

This is a division of application Ser. No. 07/079,875, filed July 30, 1987, now U.S. Pat. No. 4,886,809.

FIELD OF THE INVENTION

The present invention relates to novel carbostyril derivatives and salts thereof. More particularly, the invention relates to the carbostyril derivatives and salts thereof, processes for preparing the same, and a cardiotonic composition containing said carbostyril derivative as the active ingredient.

PRIOR ART

There have been known some carbostyril derivatives and salts thereof having the chemical structural formula similar to those of the novel carbostyril derivatives and salts thereof represented by the general formula (1) according to the present invention. (Cf. U.S. Pat. No. 4,415,572; U.S. Pat. No. 4,435,404; U.S. Pat. No. 4,454,130; U.S. Pat. No. 4,487,772; U.S. Pat. No. 4,514,401; U.S. Pat. No. 4,593,035; European Patent No. 0 187 322; European Patent No. 0 202 760; British Patent No. 2,017,701; British Patent No. 2,063,869; British Patent No. 2,071,094; Japanese Patent Kokai (Laid-open) No. 51-68574 (1976); Japanese Patent Kokai (Laid-open) No. 54-16478 (1979); Japanese Patent Kokai (Laid-open) No. 55-85520 (1980); Japanese Patent Kokai (Laid-open) No. 57-154129 (1982); Japanese Patent Kokai (Laid-open) No. 58-135865 (1983); Japanese Patent Kokai (Laid-open) No. 59-29668 (1984) and Japanese Patent Kokai (Laid-open) No. 55-83749 (1980).

SUMMARY OF THE INVENTION

An object of the present invention is to provide novel carbostyril derivatives and salts thereof represented by the general formula (1).

Another object of the present invention is to provide processes for preparing novel carbostyril derivatives and salts thereof represented by the general formula (1).

Further object of the present invention is to provide a cardiotonic composition containing said novel carbostyril derivative or salt thereof represented by the general formula (1) as the active ingredient.

DETAILED DESCRIPTION OF PREFERRED EMBODIMENTS

Novel carbostyril derivatives and salts thereof according to the present invention are represented by the general formula (1),

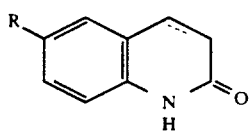
(1)

wherein R is a group of the formula

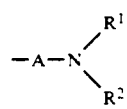

(wherein A is a group of the formula

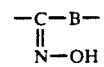

((wherein B is a lower alkylene group)) or a group of the formula

$R^1$ and $R^2$ are each the same or different and are each a lower alkyl group or a phenyl-lower alkyl group which may have lower alkoxy groups as the substituents on the phenyl ring; furthermore, $R^1$ and $R^2$ may form, together with the adjacent nitrogen atom being bonded thereto, a group of the formula

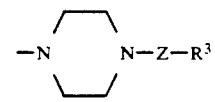

((wherein $R^3$ is a phenyl group which may have 1 to 2 substituents selected from the group consisting of a halogen atom, a lower alkyl group, a lower alkoxy group, a lower alkylthio group and a lower alkylenedioxy group; Z is a group of the formula

a group of the formula

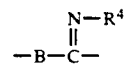

wherein $R^4$ is a hydroxyl group, a lower alkanoyloxy group or a lower alkoxy group, or a group of the formula

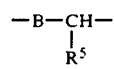

wherein B is the same as defined above, and $R^5$ is a cyano group, a halogen atom or a group of the formula

wherein $R^6$ and $R^7$ are each the same or different, and are each a hydrogen atom, a lower alkyl group, a lower alkoxycarbonyl group, a benzoyl group or a lower alkanoyl group; further $R^6$ and $R^7$ may form, together with the adjacent nitrogen atom being bonded thereto, and further with or without an additional nitrogen atom or oxygen atom, a 5- or 6-membered saturated or unsaturated heterocyclic group)) );
or a group of the formula

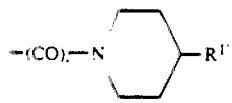

(wherein $R^{1'}$ is a lower alkylenedioxy group, an oxo group, a hydroxyimino group, a lower alkanoyloxyimino group, a group of the formula $=N-A'$ wherein $A'$ is a lower alkyl group, a phenyl-lower alkyl group, a lower alkylsulfonyl group or a phenoxy-lower alkyl group)) or a group of the formula

((wherein $R^{4'}$ and $R^{5'}$ are each the same or different and are each a hydrogen atom, a lower alkyl group, a lower alkanoyl group, a phenyl-lower alkyl group, a lower alkoxycarbonyl group, a lower alkylsulfonyl group, a benzoyl group which may have 1 to 3 substituents selected from the group consisting of a lower alkoxy group and a halogen atom on the phenyl ring, a phenyl-lower alkanoyl group, a phenyl-lower alkenylcarbonyl group which may have lower alkoxy groups as the substituents on the phenyl ring, or a phenoxy-lower alkyl group)); and l is 0 or 1);

or a group of the formula

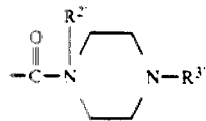

(wherein $R^{2'}$ is a hydrogen atom or a lower alkyl group; $R^{3'}$ is a hydrogen atom, a lower alkyl group, a lower alkanoyl group, a phenyl-lower alkyl group which may have 1 to 3 substituents on the phenyl ring, selected from the group consisting of a lower alkoxy group, a halogen atom and a nitro group, further the alkyl moiety may be substituted with a halogen atom, a cyano group or a hydroxyl group; a benzoyl-lower alkyl group, a phenyl-lower alkenyl group, a lower alkenyl group, a phenoxy-lower alkyl group, a phenylthio-lower alkyl group or an anilino-lower alkyl group in which the amino moiety may be substituted with a lower alkyl group);

the carbon-carbon bond between 3- and 4-positions in the carbostyril skeleton is a single or double bond;

provided that, when $R^1$ and $R^2$ are each the same or different and are each a lower alkyl group or a phenyl-lower alkyl group which may have lower alkoxy groups as the substituents on the phenyl ring, and when $R^1$ and $R^2$ form, together with the adjacent nitrogen atom being bonded thereto, a group of the formula

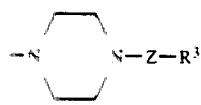

(wherein $R^3$ is the same as defined above; and Z is a group of the formula

then A is a group of the formula

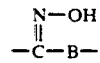

(wherein B is the same as defined above);

further provided that, when l is 0, and $R^{4'}$ hydrogen atom, a lower alkyl group or a phenyl-lower alkyl group, then $R^{5'}$ should be neither a hydrogen atom, a lower alkyl group nor a phenyl-lower alkyl group.

Novel carbostyril derivatives and salts thereof represented by the general formula (1) according to the present invention possess useful pharmacological activities such as myocardial contraction increasing activity (positive inotropic activity), coronary blood flow increasing activity, hypotensive activity, activity for inhibiting vasoconstriction induced by norepinephrine, and anti-inflammatory effect, therefore they are useful as cardiotonic agents for curing and treating various heart diseases such as congestive heart failure, mitral valve disease, arterial fibrillation, arterial flutter, paroxysmal arterial tachycardia and the like; hypotensive agents and anti-inflammatory agents. Specifically, carbostyril derivatives and salts thereof represented by the general formula (1) show excellent positive inotropic activity, coronary blood flow increasing activity as well as hypotensive activity in one hand, while they do not possess activity for increasing heart beat at all substantially on the other hand, also novel carbostyril derivatives and salts thereof represented by the general formula (1) are featured in that they show quite low toxicity as well as possess low side-effects in central nervous system activities such as vomiting, decreasing of motorium and tremor or thrill.

In the present specification, the specific examples of the substituents being defined in the respective symbols are explained as follows.

The term "a lower alkyl group" means a straight or branched chain alkyl group having 1 to 6 carbon atoms, and the examples including, methyl, ethyl, propyl, isopropyl, butyl, tert-butyl, pentyl and hexyl groups and the like.

The term "a lower alkanoyl group" means a straight or branched chain alkanoyl group having 1 to 6 carbon atoms, and the examples including, formyl, acetyl, propionyl, butyryl, pentanoyl, tert-butylcarbonyl and hexanoyl groups and the like.

The term "a phenyl-lower alkyl group" means a phenylalkyl group in which the alkyl moiety is a straight or branched chain alkyl group having 1 to 6 carbon atoms, and the examples including, benzyl, 2-phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups and the like.

The term "a lower alkoxycarbonyl group" means a straight or branched chain alkoxycarbonyl group having 1 to 6 carbon atoms, and the examples including, methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

The term "a lower alkylsulfonyl group" means a straight or branched chain alkylsulfonyl group having 1 to 6 carbon atoms, and the examples including, methylsulfonyl, ethylsulfonyl, propylsulfonyl, isopropylsulfonyl, butylsulfonyl, tert-butylsulfonyl, pentylsulfonyl and hexylsulfonyl groups as the like.

The term "a benzoyl group which may have 1 to 3 substituents on the phenyl ring, selected from the group consisting of a lower alkoxy group and a halogen atom" means a benzoyl group which may have 1 to 3 substituents, on the phenyl ring, selected from the group consisting of a straight or branched chain alkoxy group having 1 to 6 carbon atoms and a halogen atom, and the examples including, benzoyl, 4-fluorobenzoyl, 3-bromobenzoyl, 2-chlorobenzoyl, 3-chlorobenzoyl, 4-chlorobenzoyl, 4-iodobenzoyl, 4-methoxybenzoyl, 3-ethoxybenzoyl, 2-propoxybenzoyl, 4-n-butoxybenzoyl, 3-pentyloxybenzoyl, 2-hexyloxybenzoyl, 3,4-dichlorobenzoyl, 2,6-dichlorobenzoyl, 2,4-dibromobenzoyl, 2,4,6-trichlorobenzoyl, 3,4-dimethoxybenzoyl, 2,6-dimethoxybenzoyl and 2,4,6-trimethoxybenzoyl groups and the like.

The term "a phenyl-lower alkanoyl group" means a phenylalkanoyl group in which the alkanoyl moiety is a straight or branched chain alkanoyl group having 2 to 6 carbon atoms, the examples including, 3-phenylpropionyl, 4-phenylbutyryl, 5-phenylpentanoyl, 6-phenylhexanoyl, 2-methyl-3-phenylpropionyl and 2,2-dimethyl-3-phenylpropionyl groups and the like.

The term "a phenyl-lower alkenylcarbonyl group which may have lower alkoxy groups as the substituents on the phenyl ring" means a phenylalkenylcarbonyl group which may have 1 to 3 straight or branched chain alkoxy groups having 1 to 6 carbon atoms as the substituents on the phenyl ring, and the alkenylcarbonyl moiety is a straight or branched chain alkenylcarbonyl group having 3 to 6 carbon atoms, the examples including, cinnamoyl, 4-phenyl-2-butenoyl, 5-phenyl-3-pentenoyl, 5-phenyl-4-pentenoyl, 4-phenyl-2-methyl-2-butenoyl, 6-phenyl-3-hexenbyl, 4-methoxycinnamoyl, 3,4-dimethoxycinnamoyl, 4-(3-ethoxyphenyl)-2-butenoyl, 5-(2-propoxyphenyl)-3-pentenoyl, 5-(4-n-butoxyphenyl)-4-pentenoyl, 4-(3-pentyloxyphenyl)-2-methyl-2-butenoyl, 6-(2-hexyloxyphenyl)-3-hexenoyl and 3,4,5-trimethoxycinnamoyl groups and the like.

The term "a phenoxy-lower alkyl group" means a phenoxyalkyl group in which the alkyl moiety is a straight or branched chain alkyl group having 1 to 6 carbon atoms, the examples including, phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl and 2-methyl-3-phenoxypropyl groups and the like.

The term "a phenyl-lower alkyl group which may have 1 to 3 substituents selected from the group consisting of a lower alkoxy group, a halogen atom and a nitro group on the phenyl ring, further the alkyl moiety may substituted with a halogen atom, a cyano group or a hydroxyl group" means a phenylalkyl group which may have 1 to 3 substituents on the phenyl ring, selected from the group consisting of a straight or branched chain alkoxy group having 1 to 6 carbon atoms, a halogen atom and a nitro group, further the alkyl moiety is a straight or branched chain alkyl group having 1 to 6 carbon atoms which may substituted with a halogen atom, a cyano group or a hydroxyl group, further substituted with 1 to 2 phenyl groups, the examples including, in addition to the examples in .the above-mentioned "phenyl-lower alkyl group", 4-methoxybenzyl, 3-ethoxybenzyl, 2-propoxybenzyl, 4-n-butoxybenzyl, 3-pentyloxybenzyl, 2-hexyloxybenzyl, 4-nitrobenzyl, 2-nitrobenzyl-, 2-nitrobenzyl, 2-(4-methoxyphenyl)ethyl, 1-(3-ethoxyphenyl)ethyl, 3-(2-propoxyphenyl)propyl, 4-(4-n-butoxyphenyl)butyl, 5-(2-nitrophenyl)pentyl, 4-fluorobenzyl, 3-bromobenzyl, 2-chlorobenzyl, 3-chlorobenzyl, 4-chlorobenzyl, 4-iodobenzyl, 2,6-dichlorobenzyl, 3,4-dichlorobenzyl, 2,4-dibromobenzyl, 2,4,6-trichlorobenzyl, 3,4-dimethoxybenzyl, 2,6-dimethoxybenzyl, 2,4,6-trimethoxybenzyl, 2,4-dinitrobenzyl, 6-(4-chlorophenyl)hexyl, 5-(2-chlorophenyl)pentyl, 3-(3-chlorophenyl)propyl, 2-(2,6-dichlorophenyl)ethyl, 2-phenyl-2-hydorxyethyl, 2-cyano-3-phenylpropyl, 1-phenyl-1-hydroxymethyl, 3-hydroxy-3-phenypropyl, 2-hydroxy-3-phenylpropyl, 4-hydroxy-4-phenylbutyl, 5-hydroxy-5-phenylpentyl, 6-hydroxy-6-phenylhexyl, 3-hydroxy-5-phenylpentyl, 4-hydroxy-6-phenylhexyl, 2-hydroxy-4-phenylbutyl, 1-phenyl-1-cyanomethyl, 2-phenyl-2-cyanoethyl, 1-phenyl-1-chloromethyl, 2-phenyl-2-bromoethyl, 2-fluoro-3-phenylpropyl, 4-iodo-4-phenylbutyl, 5-chloro-5-phenylpentyl, 6-chloro-6-phenylhexyl, 3-chloro-5-phenylpentyl, 4-bromo-6-phenylhexyl, 2-fluoro-4-phenylbutyl, diphenylmethyl, 2,2-diphenylethyl, 3,3-diphenylpropyl, 3,4-diphenylbutyl, 4,5-diphenylpentyl, 6,6-diphenylhexyl, 2-cyano-3-phenylpropyl, 4-cyano-4-phenylbutyl, 5-cyano-5-phenylpentyl, 6-cyano-6-phenylhexyl, 3-cyano-5-phenylpentyl, 4-cyano-6-phenylhexyl, 2-cyano-4-phenylbutyl, 3-cyano-3-(4-methoxyphenyl)propyl, 2-(2-chlorophenyl)-2-hydroxyethyl, 3-hydroxy-3-(4-nitrophenyl)propyl, 3-hydroxy-3-(3,4-dimethoxyphenyl)propyl, 2-(3-chlorophenyl)-2-hydroxyethyl, 3-hydroxy-3-(4-chlorophenyl)propyl, 3-cyano-3-(2,6-dichlorophenyl)propyl and 3-cyano-3-(3-nitrophenyl)propyl groups and the like.

The term "a benzoyl-lower alkyl group" means a benzoylalkyl group in which the alkyl moiety is a straight or branched chain alkyl group having 1 to 6 carbon atoms, the examples including, benzoylmethyl, 2-benzoylethyl, 1-benzoylethyl, 3-benzoylpropyl, 4-benzoylbutyl, 1,1-dimethyl-2-benzoylethyl, 5-benzoylpentyl, 6-benzoylhexyl and 2-methyl-3-benzoylpropyl groups and the like.

The term "a phenyl-lower alkenyl group" means a phenylalkyl group in which the alkenyl group is a straight or branched chain alkenyl group having 2 to 6 carbon atoms, the examples including, styryl, 3-phenyl-1-propenyl, 3-phenyl-2-propenyl, 4-phenyl-3-butenyl, 4-phenyl-2-butenyl, 5-phenyl-4-pentenyl, 5-phenyl-3-pentenyl, 5-phenyl-2-pentenyl, 6-phenyl-5-hexenyl, 6-phenyl-4-hexenyl, 6-phenyl-3-hexenyl, 6-phenyl-2-hexenyl, 2-methyl-4-phenyl-3-butenyl, 2-methylstyryl and 1-methylstyryl groups and the like.

The term "an alkenyl group" means a straight or branched chain alkenyl group having 1 to 12 carbon atoms, the examples including, vinyl, allyl, 2-butenyl, 3-butenyl, 1-methylallyl, 2-pentenyl, 2-hexenyl, 1-heptenyl, 1-octenyl, 1-nonenyl, 1-decenyl, 1-undecenyl, 1-dodecenyl, 1-heptenyl, 3 -heptenyl, 2-methyl-4-heptenyl, 2-methyl-5-heptenyl, 4-methyl-2-heptenyl, 3-methyl-1-heptenyl, 1,3-heptadienyl, 1,4-heptadienyl, 1,5-heptadienyl, 1,6-heptadienyl, 2,4-heptadienyl, 2-methyl-2,4-heptadienyl, 2,6-dimethyl-2,4-heptadienyl, 2,5-dimethyl-1,3-heptadienyl, 2,4,6-trimethyl-2,4-heptadienyl, 2-octenyl, 3-octenyl, 4-octenyl, 2-methyl-5-octenyl, 2-methyl-6-octenyl, 2-methyl-6-octenyl, 2-methyl-7-octenyl, 1,3-octadienyl, 1,4-octadienyl, 1,5-octadienyl, 1,6- octadienyl, 1,7-octadienyl,2,4-octadienyl, 3,7-octadienyl, 4,8-dimethyl-3,7-octadienyl, 2,4,6-trimethyl-3,7-octadienyl, 3,4-dimethyl-2,5-octadienyl, 4,8-dimethyl-2,6-octadienyl, 2-nonenyl, 3-nonenyl, 4-nonenyl, 2-methyl-5-nonenyl, 2-methyl-6-nonenyl, 2-methyl-7-nonenyl, 2-methyl-8-nonenyl, 1,3-nonadienyl, 1,4-nonadienyl, 1,5-nonadienyl, 1,6-nonadienyl, 1,7-nonadienyl, 1,8-nonadienyl, 2,4-nonadienyl, 3,7-nonadienyl, 4,8-dimethyl-3,7-nonadienyl, 2,4,6-trimethyl-3,7-nonadienyl, 3,4-dimethyl-2,5-nonadienyl, 4,8-dimethyl-2,6-nonadienyl, 2-decenyl, 3-decenyl, 4-decenyl, 5-decenyl, 2-methyl-6-decenyl, 3-methyl-7-decenyl, 4-methyl-8-decenyl, 5-methyl-9-decenyl, 1,3-decadienyl, 1,4-decadienyl, 1,5-decadienyl, 1,6-decadienyl, 1,7-decadienyl, 1,8-decadienyl, 1,9-decadienyl, 2-methyl-2,4-decadienyl, 3-methyl-2,5-decadienyl, 4,8-dimethyl-2,6-decadienyl, 2,4,6-trimethyl-3,7-decadienyl, 2,9-dimethyl-3,7-decadienyl, 2-undecenyl, 3-undecenyl, 4-undecenyl, 5-undecenyl, 2-methyl-6-undecenyl, 3-methyl-7-undecenyl, 4-methyl-8-undecenyl, 5-methyl-9-undecenyl, 2-methyl-10-undecenyl, 1,3-undecadienyl, 1,4-undecadienyl, 1,5-undecadienyl, 1,6-undecadienyl, 1,7-undecadienyl, 1,8-undecadienyl, 1,9-undecadienyl, 1,10-undecadienyl, 2-methyl-2,4-undecadienyl, 3-methyl-2,5-undecadienyl, 4,8-dimethyl-2,6-undecadienyl, 2,4,6-trimethyl-3,8-undecadienyl, 2,9-dimethyl-3,8-undecadienyl, 2-dodecenyl, 3-dodecenyl, 4-dodecenyl, 5-dodecenyl, 6-dodecenyl, 2-methyl-dodecenyl, 3-methyl-8-dodecenyl, 4-methyl-9-dodecenyl, 5-methyl-10-dodecenyl, 6-methyl-11-dodecenyl, 2-methyl-2,4-dodecadienyl, 3-methyl-2,5-dodecadienyl, 4,8-dimethyl-2,6-dodecadienyl, 2,4,6-trimethyl-2,7-dodecadienyl, 2,10-dimethyl-2,8-dodecadienyl, 2,5-dimethyl-3,7-dodecadienyl, 4,8,12-trimethyl-3,7,11-dodecadienyl, 1,3,5-heptatrienyl, 2,4,6-octatrienyl, 2,4,6-octatrienyl, 1,3,6-nonatrienyl, 2,6,8-decatrienyl and 1,5,7-undecatrienyl groups and the like.

The term "a phenylthio-lower alkyl group" means a phenylthioalkyl group in which the alkyl moiety is a straight or branched chain alkyl group having 1 to 6 carbon atoms, the examples including, phenylthiomethyl, 2-phenylthioethyl, 1-phenylthioethyl, 3-phenylthiopropyl, 4-phenylthiobutyl, 1,1-dimethyl-2-phenylthioethyl, 5-phenylthiopentyl, 6-phenylthiohexyl and 2-methyl-3-phenylthiopropyl groups and the like.

The term "an anilino-lower alkyl group in which the amine moiety is substituted with lower alkyl groups" means a anilinoalkyl group in which the alkyl moiety is a straight or branched chain alkyl group having 1 to 6 carbon atoms and the amine moiety is substituted with straight or branched chain alkyl groups having 1 to 6 carbon atoms, the examples including, anilinomethyl, 2-anilinoethyl, 1-anilinoethyl, 3-anilinopropyl, 4-anilinobutyl, 1,1-dimethyl-2-anilinoethyl, 5-anilinopentyl, 6-anilinohexyl, 2-methyl-3-anilinopropyl, N-methylanilinomethyl, 2-(N-methylanilino)ethyl, 1-(N-ethylanilino)ethyl, 3-(N-propylanilino)propyl, 4-(N-butylanilino)butyl, 1,1-dimethyl-2-(N-pentylanilino)ethyl, 5-(N-hexylanilino)pentyl, 6-(N-methylanilino)hexyl and 2-methyl-3-(N-ethylanilino)propyl groups and the like.

The term "a lower alkanoyloxy group" means a straight or branched chain alkanoyloxy group having 1 to 6 carbon atoms, the examples including, formyloxy, acetyloxy, propionyloxy, butyryloxy, isobutyryloxy, pentanoyloxy, tert-butylcarbonyloxy and hexanoyloxy groups and the like.

The term "a lower alkylenedioxy group" means a straight or branched chain alkylenedioxy group having 1 to 4 carbon atoms, the examples including, methylenedioxy, ethylenedioxy, trimethylenedioxy and tetramethylenedioxy groups and the like.

The term "a lower alkoxy group" means a straight or branched chain alkoxy group having 1 to 6 carbon atoms, the examples including, methoxy, ethoxy, propoxy, isopropoxy, butoxy, tert-butoxy, pentyloxy and hexyloxy groups and the like.

The term "a lower alkylene group" means a straight or branched chain alkylene group having 1 to 6 carbon atoms, the examples including, methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups and the like.

The term "a halogen atom" means a fluorine atom, chlorine atom, a bromine atom, and an iodine atom or the like.

The term "a lower alkylthio group" means a straight or branched chain alkylthio group having 1 to 6 carbon atoms, the examples including, methylthio, ethylthio, propylthio, isopropylthio, butylthio, tert-butylthio, pentylthio and hexylthio groups and the like.

The term "$R^6$ and $R^7$ may form, together with the adjacent nitrogen atom being bonded thereto, and further with or without an additional nitrogen atom or oxygen atom, a 5- or 6-membered saturated or unsaturated heterocyclic group" means a piperidino, piperazino, morpholino, imidazolyl, pyrrolyl and pyrrolidyl groups and the like.

Novel carbostyril derivatives and salts thereof of the present invention can be prepared according to various processes such as for example reaction process formulas as follows.

Reaction process formula-1

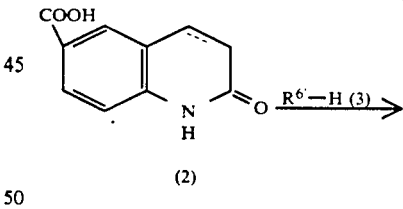

(2)

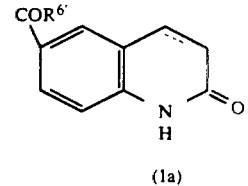

(1a)

wherein $R^6$ is a group of the formula

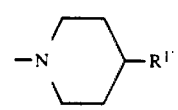

(wherein $R^{1'}$ is the same as defined above), or a group of the formula

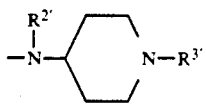

(wherein R²' and R³' are the same as defined above); and the carbon-carbon bond between 3- and 4-positions in the carbostyril skeleton are the same as defined above.

According to reaction process formula-1, a carbostyril derivative represented by the general formula (1a) can be prepared by reacting a carbostyril derivative or its carboxylic group-activated compound represented by the general formula (2) with an amine or its amino group-activated compound represented by the general formula (3) under a conventional amide bond forming reaction condition.

As to the amide bond forming reaction condition, the following methods can be exemplified, for example, p
(a) mixed acid anhydride method: e.g., a method by reacting a carboxylic acid (2) with an alkyl halocarboxylic acid to form a mixed acid anhydride, then the mixed acid anhydride is reacted with an amine (3);

(b) activated ester method: e.g., a method by reacting an activated ester of a carboxylic acid (2), for example p-nitrophenyl ester, N-hydroxysuccinimide ester, 1-hydroxybenzotriazol ester, with an amine (3);

(c) carbodiimide method: e.g., a method by condensing a carboxylic acid (2) with an amine (3) in the presence of a dehydrating agent, for example, dicyclohexylcarbodiimide, carbonyldiimidazol or the like;

(d) other method: e.g., a method by reacting a carboxylic acid (2) with a dehydrating agent, for example, acetic anhydride, to obtain a carboxylic acid anhydride, then the carboxylic acid anhydride is reacted with an amine (3);

(e) a method by reacting an ester of a carboxylic acid (2), being prepared from it with a lower alcohol, with an amine (3) under a high pressure and high temperature condition;

(f) carboxylic acid halide method: e.g., a method by changing a carboxylic acid (2) into an acid halide form, then the halide of carboxylic acid (2) is reacted with an amine (3);

(g) a method by activating a carboxylic acid (2) with a phosphorus compound, for example, triphenylphosphine, diethyl cyanophosphate or diethyl chlorophosphate, then said activated compound of carboxylic acid (2) is reacted with an amine (3).

In the mixed acid anhydride method (a), the mixed acid anhydride is obtained by a conventional Schotten-Baumann reaction, and generally the mixed acid anhydride is reacted with an amine (3), without being separated from the reaction mixture of Schotten-Baumann reaction, to obtain carbostyril derivative (1a) of the present invention. The Schotten-Baumann reaction is carried out in the presence of a basic compound, for example, an organic basic compound such as triethylamine, trimethylamine, pyridine, dimethylaniline, N-methylmorpholine, 4-dimethylaminopyridine, 1,5-diazabicyclo[4.3.0]nonene-5 (DBN), 1,8-diazabicyclo[5.4.0]-undecene-7 (DBU), 1,4-diazabicyclo[2.2.2]octane (DABCO) or the like, an inorganic basic compound, such as potassium carbonate, sodium carbonate, potassium hydrogen carbonate, sodium hydrogen carbonate or the like, at a temperature about −20° C. to 100° C., preferably, at 0° C. to 50° C., for about 5 minutes to 10 hours, preferably, for 5 minutes to 2 hours.

Reaction of the thus obtained mixed acid anhydride with an amine (3) is carried out at a temperature of −20° C. to 150° C., preferably, at 10° C. to 50° C., for about 5 minutes to 10 hours, preferably, for 5 minutes to 5 hours.

The above-mentioned mixed acid anhydride method is generally carried out in the absence or presence of a suitable solvent usually used for this type of mixed acid anhydride method, concretely a halogenated hydrocarbon for example, methylene chloride, chloroform, dichloroethane or the like, an organic hydrocarbon for example, benzene, toluene, xylene or the like, an ether for example, diethyl ether, tetrahydrofuran, dimethoxyethane or the like, an ester for example, methyl acetate, ethyl acetate or the like, an aprotic polar solvent for example, N,N-dimethylformamide, dimethyl sulfoxide, hexamethylphosphoric triamide or the like can be exemplified.

As to the alkylhalocarboxylic acid used for preparing above-mentioned mixed acid anhydride can be exemplified such as methyl chloroformate, methyl bromoformate, ethyl chloroformate, isobutyl chloroformate or the like, and generally said alkylhalocarboxylic acid is used in at least an equimolar quantity, preferably, 1 to 2 times the molar quantity of the carboxylic acid (2). The amine (3) is generally used in at least an equimolar quantity, preferably, preferably 1 to 2 times the molar quantity of the carboxylic acid (2).

The activated ester method (b) as mentioned above, for example, in using N-hydroxysuccinimide ester, the reaction is generally carried out in a suitable inert solvent. As to the solvent, concretely a halogenated hydrocarbon for example, methylene chloride, chloroform, dichloroethane or the like, an aromatic hydrocarbon for example, benzene, toluene, xylene or the like, an ether for example, diethyl ether, tetrahydrofuran, dimethoxyethane or the like, an ester for example, methyl acetate, ethyl acetate or the like, an aprotic polar solvent for example, N,N-dimethylformamide, dimethyl sulfoxide, hexamethylphosphoric triamide or the like can be exemplified.

The reaction is carried out at a temperature of 0° C. to 150° C., preferably at 10° C. to 100° C., for 5 to 30 hours. The amine (3) is usually used in an equimolar quantity, preferably 1 to 2 times the molar quantity of the N-hydroxysuccinimide ester.

In the carboxylic acid halide method (d) as above, that is by reacting a carboxylic acid halide with an amine (3), the reaction can be carried out in a suitable solvent in the presence of a dehydrohalogenating agent. As to the dehydrohalogenating agent, a common basic compound which is known widely can be used, for example, a basic compound used in the above-mentioned Schotten-Baumann reaction can be used, additionally sodium hydroxide, potassium hydroxide, sodium hydride, silver carbonate, an alcoholate, for example, sodium methylate or sodium ethylate can be exemplified. An excess amount of amine (3) can also be used as the dehydrohalogenating agent. As to the solvent used in the carboxylic acid halide method, any solvent used in the above-mentioned Schotten-Baumann reaction can also be used, further an alcohol such as, methanol, ethnaol, propanol, butanol, 3-methoxy-1-butanol, ethyl cellosolve, methyl cellosolve or the like, pyridine, acetone, acetonitrile or the like or a mixture of the solvents in combination of two or more of of the above-mentioned solvents can also be exemplified.

There is not any restriction to the ratio of the amount of an amine (3) to the amount of a carboxylic acid halide in the above reaction, the ratio can be selected from a wide range, and the latter may be used at least in an equimolar quantity, preferably an equimolar to 2 times the molar quantity to the former.

The reaction is generally carried out at a temperature of −30° C. to 180° C., preferably at about 0° C. to 150° C., and the reaction is completed for 5 minutes to 30 hours.

The carboxylic acid halide used in this reaction can be prepared by reacting a carboxylic acid derivative (2) with a halogenating agent in the absence or presence of a solvent. As to the solvent, any solvent which does not give any adverse effect to the reaction can be used, for example, an aromatic hydrocarbon such as benzene, toluene, xylene or the like, a halogenated hydrocarbon such as chloroform, methylene chloride, carbon tetrachloride or the like, an ether such as dioxane, tetrahydrofuran, diethyl ether or the like, dimethylformamide, dimethyl sulfoxide or the like can be exemplified. As to the halogenating agent, a common halogenating agent which changes the hydroxyl group in the carboxyl group into the halogen atom can be used, for example, thionyl chloride, phosphorus oxychloride, phosphorus oxybromide, phosphorus pentachloride, phosphorus pentabromide or the like can be exemplified.

There is not any specific restriction to the ratio of the amount of a carboxylic acid (2) to the amount of a halogenating agent in the reaction, the ratio can be selected from a wide range, when the reaction is carried out in the absence of a solvent, the latter is used in an excess amount to the former, and when the reaction is carried out in the presence of a solvent, the latter is used at least in an equimolar quantity, preferably, 2 to 4 times the molar quantity to the former. The reaction temperature (and the reaction time) may not be restricted, and generally the reaction can be carried out at room temperature to 100° C., preferably at 50° C. to 80° C., for 30 minutes to 6 hours.

In the method (g), by activating a carboxylic acid (2) with a phosphorus compound, for example, triphenylphosphine, diethyl cyanophosphate or diethyl chlorophosphate, then said activated compound of carboxylic acid (2) is reacted with an amine (3), the reaction can be carried out in a suitable solvent. As to the solvent, any solvent which does not give adverse effect to the reaction can be used, concretely for example, a halogenated hydrocarbon such as methylene chloride, chloroform, dichloromethane or the like, an aromatic hydrocarbon such as benzene, toluene, xylene or the like, an ether such as diethyl ether, tetrahydrofuran, dimethoxyethane or the like, an ester such as methyl acetate, ethyl acetate or the like, an aprotic polar solvent such as N,N-dimethylformamide, dimethyl sulfoxide, hexamethylphosphoric triamide or the like can be exemplified.

In this reaction, since an amine (3) per se performs as a basic compound, the reaction can be proceeded smoothly by using the amine (3) in an amount excessive to theoretical quantity, and further, if necessary other basic compound, for example an organic basic compound such as triethylamine, trimethylamine, pyridine, dimethylaniline, N-methylmorpholine, DBN, DBU, DABCO or the like, an inorganic basic compound, such as potassium carbonate, sodium carbonate, potassium hydrogen carbonate, sodium hydrogen carbonate or the like can be used.

The reaction can be carried out at a temperature of about 0° C. to 150° C., preferably at about 0° C. to 100° C., and the reaction time is about 1 to 30 hours. The ratio of the amounts of a phosphorus compound and an amine (3) to the amount of a carboxylic acid derivative (2) is generally at least in an equimolar quantity, preferably 1 to 3 times the molar quantity.

Reaction process formula-2

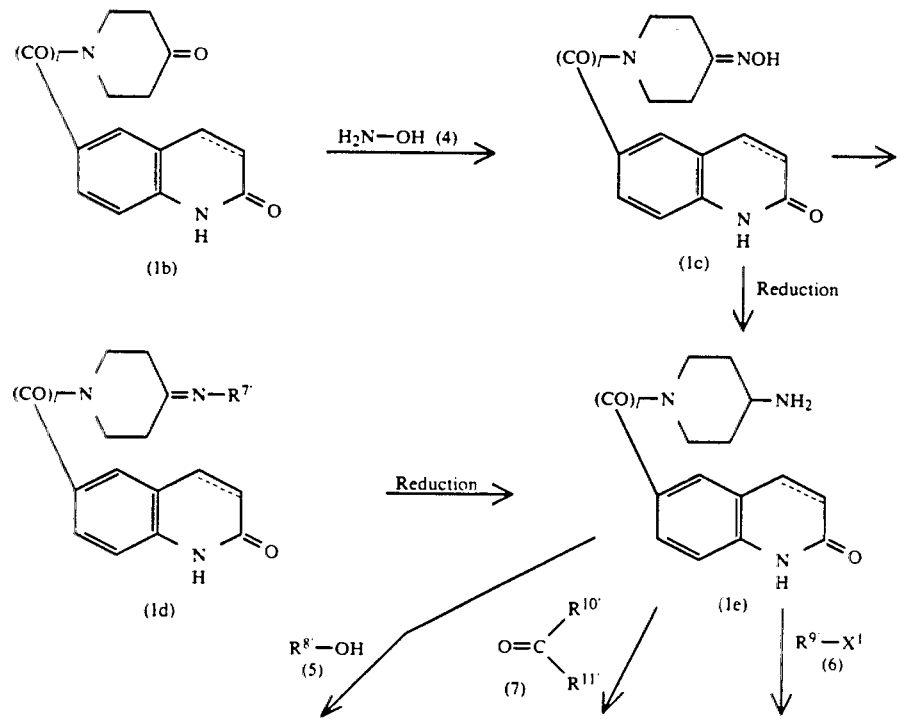

-continued
Reaction process formula-2

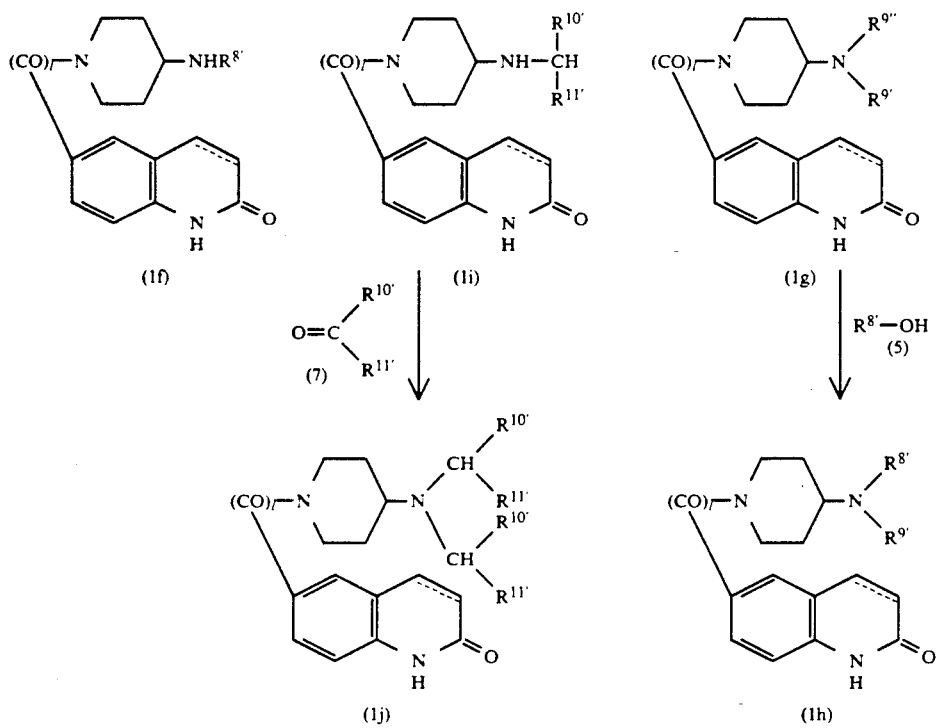

wherein l is 0 or 1; $R^{7'}$ is a lower alkanoyloxy group; $R^{8'}$ is a lower alkanoyl group, a lower alkoxycarbonyl group, a benzoyl group which may have 1 to 3 substituents, on the phenyl ring, selected from the group consisting of a lower alkoxy group and a halogen atom, a phenyl-lower alkanoyl group or a phenyl-lower alkenylcarbonyl group which may have lower alkoxy groups as the substituents on the phenyl ring; $R^{9'}$ is a lower alkyl group, a phenyl-lower alkyl group, a lower alkylsulfonyl group or a phenoxy-lower alkyl group; $R^{9''}$ is the same as defined in $R^{9'}$ and is further a hydrogen atom; $R^{10'}$ and $R^{11'}$ are each a hydrogen atom or a lower alkyl group; $X^{1'}$ is a halogen atom, a lower alkanesulfonyloxy group, an arylsulfonyloxy group or an aralkylsulfonyloxy group; the carbon-carbon bond between 3- and 4-positions in the carbostyril skeleton is a single or double bond.

In the general formula (6), in the definitions for the symbol $X^{1'}$, the halogen atom is specifically a chlorine, fluorine, bromine or iodine atom, the lower alkanesulfonyloxy group can be exemplified such as methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy groups and the like; the arylsulfonyloxy group is specifically a substituted or unsubstituted arylsulfonyloxy group such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy and α-naphthylsulfonyloxy group and the like; the aralkylsulfonyloxy group is specifically a substituted or unsubstituted aralkylsulfonyloxy group such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy groups and the like.

The reaction of a compound of the general formula (1b) with hydroxylamine (4) can be carried out in a suitable inert solvent, in the absence or presence of a basic compound. As to the basic compound used in this reaction, an inorganic basic compound such as sodium hydroxide, potassium hydroxide, sodium carbonate or the like; an organic basic compound such as pyridine, piperidine, triethylamine, 1,5-diazabicyclo[4.3.0] nonene-5 (DBN), 1,8-diazabicyclo [5.4.0] undecene-7 (DBU), 1,4-diazabicyclo [2.2.2] octane (DABCO), sodium acetate or the like can be exemplified. As to the inert solvent used in this reaction, any solvent which does not give any adverse effect to the reaction may be used, concretely, a lower alcohol such as methanol, ethanol, isopropanol or the like; an ether such as dioxane, tetrahydrofurane, diethyl ether, ethylene glycol monomethyl ether or the like; an aromatic hydrocarbon such as benzene, toluene, xylene or the like; a halogenated hydrocarbon such as dichloromethane, dichloroethane, chloroform, carbon tetrachloride or the like; an aprotic polar solvent such as dimethylformamide, dimethyl sulfoxide, hexamethylphosphoric triamide or the like can be exemplified. The ratio of the amount of hydroxylamine (4) to the amount of a compound of the general formula (1b) may be generally at least an equimolar quantity, preferably an equimolar to 5 times the molar quantity of the former to the latter. The reaction temperature is generally at room temperature to 200° C., preferably at room temperature to 150° C. and generally the reaction is completed in about 1 to 15 hours.

The reduction of a compound of the general formula (1c) or (1d) may be carried out in a suitable solvent, in the presence of a catalyst by means of catalytic hydrogenation. As to the solvent used in this reduction, water, acetic acid, a lower alcohol such as methanol, ethanol, isopropanol or the like, a hydrocarbon such as hexane, cyclohexane or the like, an ether such as diethylene glycol dimethyl ether, dioxane, tetrahydrofuran, diethyl ether or the like, an ester such as ethyl acetate, methyl acetate or the like, and an aprotic polar solvent such as dimethylformamide or the like can be exemplified. As to the catalyst used in this reduction, palladium, palladium black, palladium-carbon, platinum, platinum oxide, copper chromite, Raney-nickel or the like may be used. The catalyst may be used in an usual catalytic amount, preferably generally 0.02 times to an equivalent amount of the catalyst can be used to a compound of the general formula (1c) or (1d). The reduction may be carried out generally at a temperature of $-20°$ C. to about room temperature, preferably at $0°$ C. to about room temperature, and under 1 to 10 atmospheric pressure of hydrogen, the reduction is generally completed in about 0.5 to 1 hour.

The reduction can also be carried out by the following method. For example, reduction by using hydrogenating reducing agent may preferably be used. As to the hydrogenating reducing agent, sodium aluminum hydride, sodium borohydride, dibarane or the like can be exemplified. Said hydrogenating reducing agent is used generally at least in an equimolar quantity, preferably an equimolar quantity to 10 times the molar quantity of the reducing agent is used to a compound of the general formula (1c) or (1d). This reduction can be carried out in a suitable solvent, for example water, a lower alcohol such as methanol, ethanol, isopropanol or the like, an ether such as tetrahydrofuran, diethyl ether, diethylene glycol dimethyl ether or the like. This reduction can be carried out at a temperature of about $-60°$ C. to $50°$ C., preferably at $-30°$ C. to room temperature, for about 10 minutes to 15 hours. In carrying out the reduction by using lithium aluminum hydride or diborane as the reducing agent, an anhydrous solvent such as diethyl ether, tetrahydrofuran, diethylene glycol dimethyl ether may preferably be used.

The reaction for introducing a compound of the general formula (1c) to a compound of the general formula (1d) can be carried out in the presence of a lower alkanoylating agent. As to the lower alkanoylating agent, the examples including, a lower alkanoic acid such as formic acid, acetic acid, propionic acid or the like; a lower alkanoic acid anhydride such as acetic anhydride or the like; and a lower alkanoic acid halide such as acetyl chloride, propionyl bromide or the like. In the case of using a lower alkanoic acid anhydride or halide as to the lower alkanoylating agent, the reaction may be carried out in the presence of a basic substance. As to the basic substance, an alkali metal such as metallic sodium or metallic potassium and a hydroxide, carbonate and bicarbonate of these alkali metals; and an organic basic compound such as triethylamine, pyridine or piperidine can be exemplified. The reaction may be carried out in the absence or presence of a solvent, and generally the reaction is proceeded in a suitable solvent. As to the solvent, a ketone such as acetone, methyl ethyl ketone or the like; an ether such as diethyl ether, dioxane or the like; an aromatic hydrocarbon such as benzene, toluene, xylene or the like; a halogenated hydrocarbon such as chloroform, dichloromethane, carbon tetrachloride or the like; acetic acid, acetic anhydride, water and pyridine and the like can be exemplified.

The amount of the lower alkanoylating agent may be at least an equimolar quantity, generally in an equimolar quantity to a large excess quantity to a compound of the general formula (1c). The reaction proceeds generally at a temperature of $0°$ C. to $150°$ C., preferably at $0°$ C. to $100°$ C., and completes in about 5 minutes to 15 hours.

In the case of using a lower alkanoic acid as to the lower alkanoylating agent, the reaction may carried out in the presence of a dehydrating agent, for example, a mineral acid such as sulfuric acid, hydrochloric acid or the like; a sulfonic acid such as p-toluenesulfonic acid, benzenesulfonic acid, ethanesulfonic acid or the like. The reaction temperature is specifically determined in about $50°$ C. to $120°$ C.

The reaction of a compound of the general formula (1e) with a compound of the general formula (5) can be carried out under conditions similar to those employed in the reaction of a compound of the general formula (2) with a compound of the general formula (3) as mentioned in Reaction process formula-1.

The compound of the general formula (1g) is prepared by reacting a compound of the general formula (1e) with a compound of the general formula (6) under conditions similar to those employed in the reaction of using a carboxylic acid halide of the general formula (3).

The reaction of a compound of the general formula (1e) or (1i) with a compound of the general formula (7) may be carried out in the absence or presence of a suitable solvent in the presence of a reducing agent. As to the solvent, water, an alcohol such as methanol, ethanol, isopropanol or the like; acetic acid; an ether such as dioxane, diethyl ether, diethylene glycol dimethyl ether, tetrahydrofuran or the like; an aromatic hydrocarbon such as benzene, toluene, xylene or the like can be exemplified.

Reduction can be carried out by using a hydrogenating reducing agent such as formic acid, sodium borohydride, sodium cyanoborohydride, lithium aluminum hydride or the like, or by using a catalytic hydrogenation catalyst such as palladium black, palladium-carbon, platinum oxide, platinum black, Raney nickel or the like. In the case of using formic acid as the reducing agent, the reaction temperature is generally at room temperature to $200°$ C., preferably at $50°$ C. to $150°$ C., and the reaction is completed in about 1 to 10 hours. The amount of formic acid may be of a large excess amount to a compound of the general formula (1e) or (1i). In the case of using other hydrogenating reducing agent, the reaction temperature is generally at $-30°$ C. to $100°$ C., preferably at $0°$ C. to $70°$ C., and the reaction is completed in about 30 minutes to 12 hours. The amount of said reducing agent is generally in as equimolar to 20 times the molar quantity, preferably 1 to 5 times the molar quantity to a compound of the general formula (1e) or (1i). Specifically, when lithium aluminum hydride is used as the reducing agent, an ether such as diethyl ether, dioxane, tetrahydrofuran, diethylene glycol dimethyl ether, or the like; an aromatic hydrocarbon such as benzene, toluene, xylene or the like may preferably be used as the solvent.

In the case of using a catalytic hydrogenation catalyts, the reaction may be carried out under a normal pressure to 20 atmospheric pressure, preferably at a normal pressure to 10 atmospheric pressure of hydrogen gas stream, and generally at $-30°$ C. to $100°$ C., preferably at $0°$ C. to $60°$ C., and generally the reaction is completed in 1 to 12 hours. The amount of the catalyst may be generally 0.1 to 40 parts by weight, preferably in amount of 1 to 20 parts by weight to a compound of the general formula (1e) or (1i).

The amount of a compound of the general formula (7) to a compound of the general formula (1e) or (1i) is generally in an equimolar quantity, preferably in an equimolar to a large excess quantity.

A compound of the general formula (1g) wherein $R^{9'}$ is a lower alkyl group or a phenyl-lower alkyl group can be prepared by reducing a compound (1f) or (1h) wherein $R^{8'}$ is a lower alkanoyl group, benzoyl group or a phenyl-lower alkanoyl group. This reduction can be carried out by procedures similar to those employed in the reduction of a compound of the general formula (1c) or (1d) using a hydrogenation reducing agent. The reduction may be carried out generally at $-60°$ C. to $150°$ C., preferably at $-30°$ C. to $100°$ C.

Reaction process formula-3

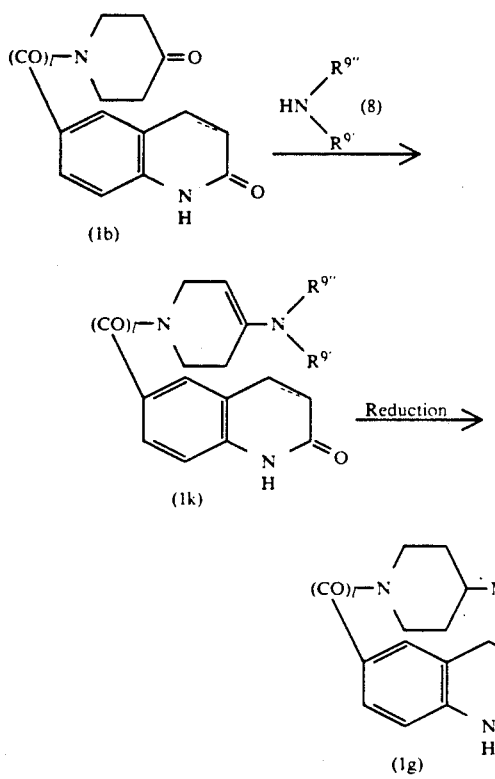

wherein l, $R^{9'}$, $R^{9''}$ and the carbon-carbon bond between 3- and 4-positrons in the carbostyril skeleton are the same as defined above.

The reaction of a compound of the general formula (1b) with a compound of the general formula (8) is carried out in a suitable solvent or without the solvent, and in the absence or presence of a dehydrating agent. As to the solvent, an alcohol such as methanol, ethanol, isopropanol or the like; an aromatic hydrocarbon such as benzene, toluene, xylene or the like; an aprotic polar solvent such as dimethylformamide, dimethylacetamide, N-methylpyrrolidone or the like can be exemplified. As to the dehydrating agent, a drying agent usually used in dehydrating a solvent such as molecular sieve or the like; a mineral acid such as hydrogen chloride, sulfuric acid, boron trifluoride or the like; an organic acid such as p-toluenesulfonic acid or the like can be exemplified. The reaction may be carried out generally at room temperature to $250°$ C., preferably at $50°$ C. to $200°$ C., and the reaction is generally completed in about 1 to 48 hours. The amount of a compound of the general formula (8) is not specifically restricted, and generally at least an equimolar quantity, preferably a large excess quantity may be used to a compound of the general formula (1b). As to the dehydrating agent, the drying agent may be used in a large excess quantity, and the acid may be used in a catalytic amount. Thus obtained a compound of the general formula (1k) can be used, without specifically separated from the reaction system, in the next reduction step.

The reduction of a compound of the general formula (1k) can be carried out under conditions similar to those employed in the reduction of a compound of the general formula (1c) or (1d) in the Reaction process formula-2.

When a compound of the general formula (8) wherein $R^{9''}$ is a hydrogen atom is used, then a compound of the general formula (11),

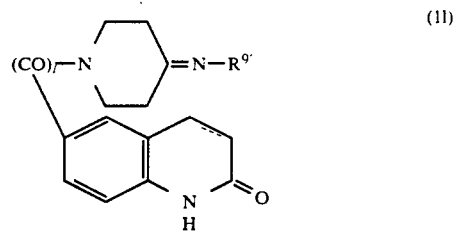

is formed, and this compound is reduced under condition similar to those employed in the reduction of a compound of the general formula (1k) to obtain a compound of the general formula (1m) as follows:

Reaction process formula-4

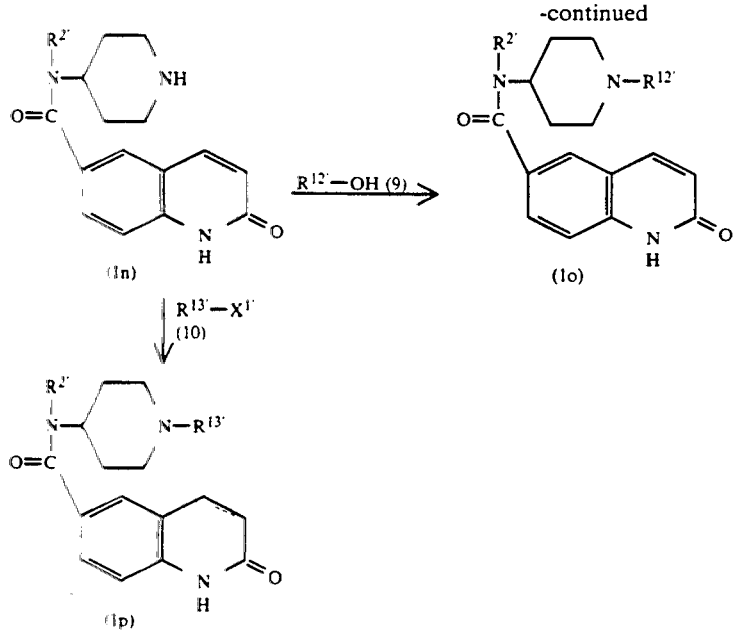

wherein $R^{2'}$, $X^{1'}$ and the carbon-carbon bond between 3- and 4-positions in the carbostyril skeleton are the same as defined above; $R^{12'}$ is a lower alkanoyl group; and $R^{13'}$ is a lower alkanoyl group and the same as defined in $R^{3'}$ except hydrogen atom.

The reaction of a compound of the general formula (1n) with a compound of the general formula (9) can be carried out under conditions similar to those employed in the reaction of a compound of the general formula (1e) with a compound of the general formula (5) in the above-mentioned Reaction process formula-2.

The reaction of a compound of the general formula (1n) with a compound of the general formula (10) can be carried out under conditions similar to those employed in the reaction of a compound of the general formula (1e) with a compound of the general formula (6) in the above-mentioned Reaction process formula-2.

Among compounds of the general formula (1p) obtained in the Reaction process formula-4, those having $R^{13'}$ is a phenyl-lower alkyl group can be dephenyl-lower alkylating (for example, debenzylating) to obtain the corresponding compound of the general formula (1n). Said dephenyl-lower alkylation can be carried out in a suitable solvent, for example, water, a lower alcohol such as methanol, ethanol, isopropanol and the like; an ether such as dioxane, tetrahydrofuran and the like; or acetic acid; or a mixed solvent of two or more of these solvents, in the presence of a catalytic reducing catalyst such as platinum oxide, palladium-carbon, palladium black and the like, at a temperature about 0° C. to 100° C., under 1 to 10 atmospheric pressure of hydrogen gas, for about 0.5 to 10 hours. (The reduction may be carried out by adding a mineral acid such as hydrochloric acid, or by heat-treating in an aqueous solution of hydrobromic acid.)

Further, the corresponding compound of the general formula (1n) can be obtained by hydrolyzing a compound of the general formula (1o) prepared in the above-mentioned Reaction process formula-4. Said hydrolysis can be carried out under conditions of usual hydrolysis, for example in the presence of a basic compound such as sodium hydroxide, potassium hydroxide, barium hydroxide, potassium carbonate and the like; a mineral acid such as sulfuric acid, hydrochloric acid, nitric acid and the like; an organic acid such as aromatic sulfonic acid, and in a solvent for example water, an alcohol such as methanol, ethanol, isopropanol and the like; a keton such as acetone, methyl ethyl ketone and the like; an ether such as dioxane, ethylene glycol and the like; acetic acid; or a mixed solvent of two or more of these solvents. The hydrolysis is carried out generally at a temperature of room temperature to 200° C., preferably at room temperature to about 150° C. and is completed in about 1 to 30 hours.

Among compounds of the general formula (1p), those having $R^{13'}$ is a phenyl-lower alkyl group can be converted into a compound of the general formula (1p) wherein $R^{13'}$ is formyl group by reducing and formulating the former in an alcohol such as methanol, ethnaol, isopropanol or the like, in the presence of a catalyst such as formic acid and palladium black. Said reduction and formulation are generally carried out at a temperature of 0° C. to 100° C., preferably at 0° C. to 70° C., and are completed in about 10 minutes to 5 hours.

Further, in compounds of the general formula (1), those having $R^{1'}$ is a lower alkylenedioxy group may be converted into compounds of the general formula (1) wherein $R^{1'}$ is an oxo group by hydrolyzing the former. Said hydrolyzing reaction can be carried out under conditions similar to those employed in the hydrolysis of a compound of the general formula (1o).

Reaction process fromula-5

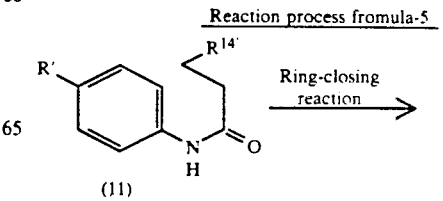

-continued
Reaction process fromula-5

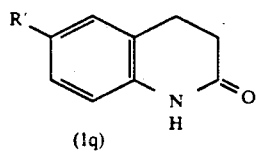

wherein R' is the same as defined above; and $R^{14'}$ is a halogen atom.

The ring-closing reaction of a compound of the general formula (11) is generally called as Friedel-Crafts reaction, and is carried out in a suitable solvent in the presence of a Lewis acid. As to the solvent used in this reaction, any solvent commonly used in this type of reaction can also be used, and carbon disulfide, nitrobenzene, chlorobenzene, dichloromethane, dichloroethane, trichloroethane, carbon tetrachloride, tetrachloroethane and the like can be exemplified. As to the Lewis acid used in this reaction, aluminum chloride, zinc chloride, ferrous chloride, tin chloride, boron tribromide, boron trifluoride, concentrated sulfuric acid can be exemplified. The Lewis acid is used as generally in an amount of 2 to 6 times the molar quantity, preferably 3 to 4 times the molar quantity to a compound of the general formula (11). The reaction temperature is generally about 20° C. to 120° C., preferably at about 40° C. to 70° C., and is generally completed in about 0.5 to 6 hours.

dium, palladium black, palladium-carbon, platinum, platinum oxide, copper chromite, Raney-nickel or the like may be used. The catalyst may be used in amount of 0.02 to 1.00 part by weight to a compound of the general formula (12). The reaction is generally carried out at about −20° C. to room temperature, preferably at 0° C. to room temperature, under 1 to 10 atmospheric pressure of hydrogen gas, and is completed generally in about 0.5 to 10 hours.

In the case of using a reducing method (ii), a mixture of iron, zinc, tin or stannous chloride with a mineral acid such as hydrochloric acid or sulfuric acid; or iron, ferrous sulfate, zinc or tin with an alkali metal hydroxide such as sodium hydroxide, a sulfide such as ammonium sulfide or the like, ammonia water and an ammonium salt such as ammonium chloride may be used as the reducing agent. As to the inert solvent used in the reduction, water, acetic acid, methanol, ethanol or dioxane or the like may be exemplified. The conditions of the above-mentioned reduction may be suitably selected according to the reducing agent used, for example. in the case of using a mixture of stannous chloride with hydrochloric acid, the reduction may be carried out advantageously at 0° C. to room temperature, for about 0.5 to 10 hours. The reducing agent may be used in at least an equimolar quantity, generally in an equimolar to 5 times the molar quantity to the stating material.

In carrying out the above-mentioned method (i), at about room temperature to 150° C., a compound of the general formula (1) can be prepared directly through a Reaction process formula-6

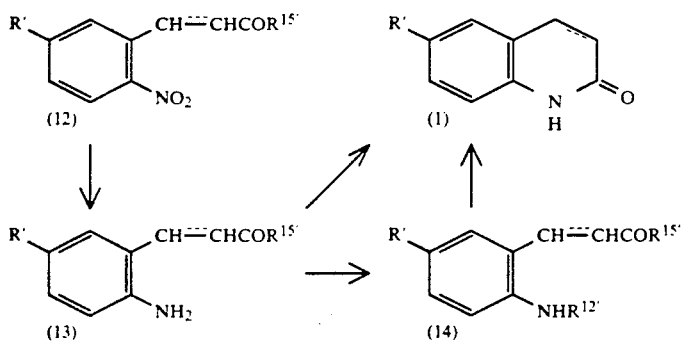

wherein R', $R^{12'}$ and the carbon-carbon bond between 3- and 4-positions in the carbostyril skeleton are the same defined above, and $R^{15'}$ is a hydroxyl group or a lower alkoxy group.

The reaction for obtaining a compound of the general formula (13) by reducing a compound of the general formula (12) can be carried out:

(i) by reducing in a suitable solvent by using a catalytic reducing catalyst, or (ii) by reducing in a suitable solvent by using, as the reducing agent, a mixture of a metal or metal salt with an acid, or a metal or metal salt with an alkalimetal hydroxide, sulfide, ammonium salt and the like.

In the case of using a catalytic reduction (i), as to the solvent, water, acetic acid, an alcohol such as methanol, ethanol, isopropanol and the like, a hydrocarbon such as hexane, cyclohexane or the like, an ether such as dioxane, diethylene glycol dimethyl ether, tetrahydrofuran, diethyl ether or the like, an ester such as ethyl acetate, methyl acetate or the like, an aprotic polar solvent such as dimethylformamide or the like can be exemplified. As to the catalyst used in the catalytic reduction, pallacompound of the general formula (13).

The acylation of a compound of the general formula (13) can be carried out under conditions similar to those employed in the reaction for introducing a compound of the general formula (1c) to a general formula (1d).

The reaction for obtaining a compound of the general formula (1) by ring-closing a compound of the general formula (13) or (14) is carried out in a suitable solvent in the presence of or absence of a basic compound or an acid, preferably in the presence or absence of an acid. As to the basic compound, any known compound can be used, for example, an organic basic compound such as triethylamine, pyridine, dimethylaniline, N-methylmorpholine, DBN, DBU, DABCO and the like; an inorganic basic compound such as potassium carbonate, sodium carbonate, sodium hydroxide, potassium hydroxide, sodium hydrogen carbonate, potassium hydrogen carbonate and the like can be exemplified. As to the acid, an inorganic acid such as hydrochloric acid, hydrobromic acid, sulfuric acid, nitric acid, polyphosphoric acid and the like, an organic acid such as p-toluenesulfonic acid, ethanesulfonic acid, trifluoroacetic acid and the like can be exemplified. As to the solvent, any inert solvent which may not give any adverse effect to the reaction can be used, for example, an alcohol such as methanol, ethanol, propanol, butanol, 3-methoxy-1-butanol, ethyl cellosolve, methyl cellosolve and the like; pyridine, acetone; a halogenated hydrocarbon such as dichloromethane, dichloroethane, chloroform and the like; an aromatic hydrocarbon such as benzene, toluene, xylene and the like; an ether such as dimethoxyethane, tetrahydrofuran, diethyl ether, diphenyl ether and the like; an ester such as ethyl acetate, methyl acetate; an aprotic polar solvent such as dimethylformamide, dimethyl sulfoxide, hexamethylphosphoric triamide and the like can be exemplified. The reaction is generally carried out at −20° C. to 150° C., preferably at 0° C. to 150° C., and is generally completed in 5 minutes to 30 hours.

Reaction process formula-7

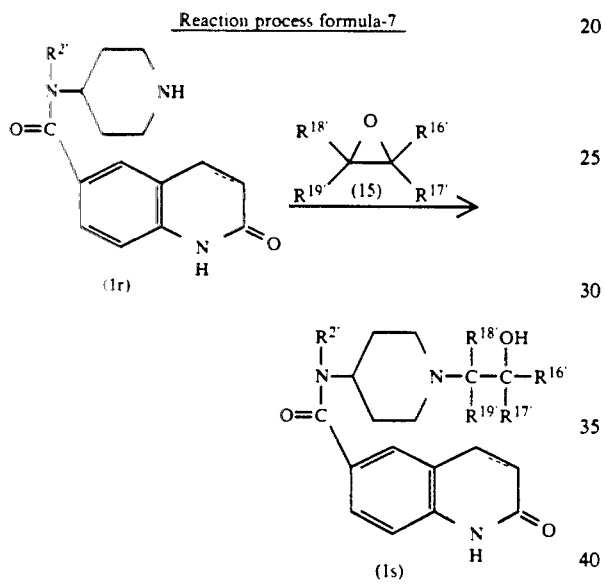

wherein $R^{2'}$ and the carbon-carbon bond between 3- and 4-positions in the carbostyril skeleton are the same as defined above; $R^{16'}$ is a phenyl group which may have 1 to 3 substituents selected from the group consisting of a lower alkoxy group, a halogen atom and a nitro group on the phenyl ring, a phenyl-lower alkyl group which may have 1 to 3 substituents, on the phenyl ring, selected from the group consisting of a lower alkoxy group, a halogen atom and a nitro group; $R^{17'}$ is a hydrogen atom or the same as the definition of the above-mentioned $R^{16'}$, $R^{18'}$ and $R^{19'}$ are each the same or different, and are each a hydrogen atom or a lower alkyl group.

The reaction of a compound of the general formula (1r) with a compound of the general formula (15) is carried out in the absence or presence of a solvent, and in the absence or presence of a basic compound. The reaction is generally proceeded at room temperature to 200° C., preferably at 60° C. to 120° C., and is completed in about 1 to 24 hours. As to the solvent used in this reaction, an ether such as dioxane, tetrahydrofuran, diethyl ether, ethylene glycol dimethyl ether and the like, an aromatic hydrocarbon such as benzene, toluene, xylene and the like, a lower alcohol such as methanol, ethanol, isopropanol and the like, a polar solvent such as N-methylpyrrolidone, dimethylformamide, dimethyl sulfoxide, hexamethylphosphoric triamide and the like can be exemplified. As to the basic compound, an inorganic basic compound such as potassium carbonate, sodium carbonate, sodium hydroxide, sodium hydrogen carbonate, sodium amide and the like, and an organic basic compound such as triethylamine, tripropylamine, pyridine, quinoline and the like can be exemplified. The amount of a compound of the general formula (1r) may be generally in an equimolar quantity, preferably in 1 to 5 times the molar quantity.

A compound of the general formula (15) used as the starting material can be prepared by a method as shown in the following Reaction process formula-8.

Reaction process formula-8

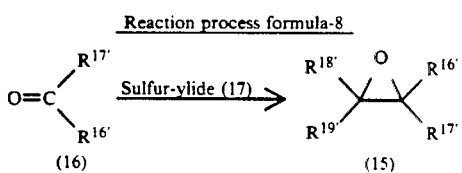

wherein $R^{16'}$, $R^{17'}$, $R^{18'}$ and $R^{19'}$ are the same as defined above.

The reaction of a compound of the general formula (16) with sulfur-ylide (17) is carried out in a suitable solvent. As to the solvent used in this reaction, an ether such as tetrahydrofuran or the like, a polar solvent such as dimethylformamide, dimethyl sulfoxide and the like can be exemplified. The reaction is generally proceeded at −50° C. to 70° C., preferably at −30° C. to 50° C., and is completed in about 10 minutes to 5 hours. As to the sulfur-ylide (17) used in this reaction, a compound represented by the general formula,

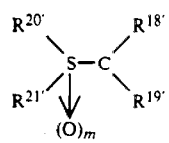

(wherein $R^{18'}$ and $R^{19'}$ are the same as defined above; m is 0 or 1; $R^{20'}$ and $R^{21'}$ are each the same or different, and are each a lower alkyl group, a phenyl group, a lower alkylamino group, a phenyl-lower alkyl group, a lower alkenyl group or a lower alkoxy group) can be exemplified.

The sulfur-ylide (17) may be used in an amount of at least an equimolar quantity, preferably an equimolar to 2 times the molar quantity to a compound of the general formula (16).

Reaction process formula-9

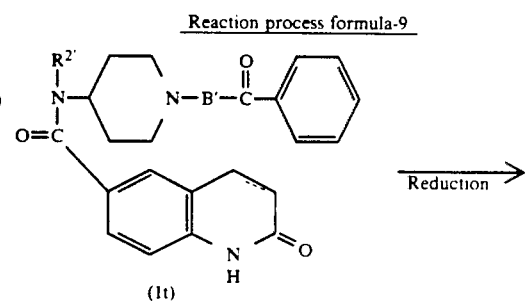

-continued
Reaction process formula-9

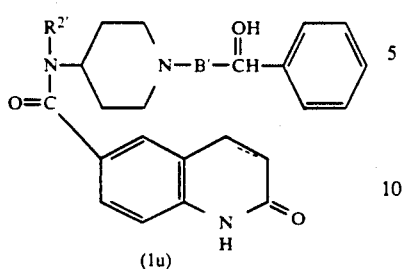

(1u)

wherein B' is a lower alkylene group and R²' and the carbon-carbon bond between 3- and 4-positions in the carbostyril skeleton are the same as defined above.

The reduction of a compound of the general formula (1t) can be carried out by various method, and preferably a method by using a hydrogenating reducing agent may be used.

As to the hydrogenating reducing agent, lithium aluminum hydride, sodium borohydride, diborane and the like can be exemplified. The amount of the hydrogenating reducing agent is generally at least an equimolar quantity, and preferably in the range of an equimolar to 10 times the molar quantity to a compound of the general formula (1t). The reduction is generally carried out in a suitable solvent, for example, water, a lower alcohol such as methanol, ethanol, isopropanol and the like, an ether such as diethylene glycol dimethyl ether, tetrahydrofuran, diethyl ether and the like, a polar solvent such as dimethylformamide, acetic acid and the like, or a mixed solvent of two or more of these solvents, and generally at $-60°$ C. to $50°$ C., preferably at $-30°$ C. to room temperature, for about 10 minutes to 3 hours.

In the case of using lithium aluminum hydride or diborane as the reducing agent, an anhydrous solvent such as diethyl ether, tetrahydrofuran or diethylene glycol dimethyl ether may preferably be used.

Reaction process formula-10

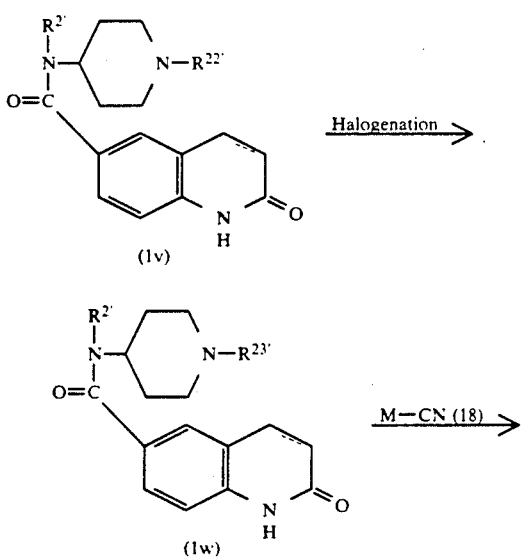

-continued
Reaction process formula-10

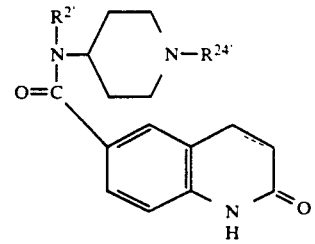

wherein R²' and the carbon-carbon bond between 3- and 4-positions in the carbostyril skeleton are the same as defined above; R²²' is a phenyl-lower alkyl group which may have 1 to 3 substituents, on the phenyl ring, selected from the group consisting of a lower alkoxy group, a halogen atom and a nitro group, further the lower alkyl moiety is substituted with hydroxyl groups; R²³' is a phenyl-lower alkyl group which may have 1 to 3 substituents, on the phenyl ring, selected from the group consisting of a lower alkoxy group, a halogen atom and a nitro group, further the lower alkyl moiety is substituted with halogen atoms; R²⁴' is a phenyl-lower alkyl group which may have 1 to 3 substituents, on the phenyl ring, selected from the group consisting of a lower alkoxy group, a halogen atom and a nitro group, further the lower alkyl moiety is substituted with cyano groups.

The halogenation of a compound of the general formula (1v) can be carried out in a suitable solvent or without the solvent, by reacting a compound of the general formula (1v) with a halogenating agent. As to the solvent used in the reaction, a aromatic hydrocarbon such as benzene, toluene, xylene or the like, a halogenated hydrocarbon such as dichloromethane, chloroform, carbon tetrachloride or the like, an ether such as dioxane, tetrahydrofuran, diethyl ether or the like, dimethylformamide, dimethyl sulfoxide or the like can be exemplified. As to the halogenating agent, a common halogenating agent which can be able to convert the hydroxyl group in the carboxyl group into halogen atoms can be selected from widely and used, for example, thionyl chloride, phosphorus oxychloride, phosphorus oxybromide, phosphorus pentachloride, phosphorus pentabromide can be exemplified.

There is not any restriction to the ratio of the amount of a compound of the general formula (1v) to the amount of the halogenating agent, and the ratio can suitably be selected from a wide range, in the case of carrying out the reaction in the absence of the solvent, generally a large excess amount of the halogenating agent may be used to the former. While in the case of carrying out the reaction in a solvent, the halogenating agent may be used at least in an equimolar quantity, preferably 2 to 4 times the molar quantity may be used to the former. The reaction temperature and the reaction time are not specifically restricted, and generally the reaction is carried out at room temperature to 100° C., and for about 30 minutes to 10 hours.

The reaction of a compound of the general formula (1w) with compound M—CN (18) can be carried out in a suitable solvent. As to the M—CN, potassium cyanide, sodium cyanide, silver cyanide, copper cyanide, calcium cyanide or the like can be exemplified. As to the solvent used in the reaction, water, an alcohol such as methanol, ethnaol, isopropanol, or the like, a halogenated hydrocarbon such as dichloromethane, chloroform, carbon tetrachloride or the like, a polar solvent such as acetonitrile, dimethylformamide, dimethyl sulfoxide or the like can be exemplified. The ratio of the amount of M—CN compound (18) to the amount of a compound of the general formula (1w) may be generally at least an equimolar quantity, preferably an equimolar to 1.5 times the molar quantity. The reaction is generally carried out at room temperature to 150° C., preferably at about 50° C. to 120° C., and is completed in about 30 minutes to 10 hours. The reaction can advantageously be proceeded by adding in the reaction system, a phase transfer catalyst for example an alkyl ammonium halide such as tetra-n-butyl ammonium iodide, tetrabutyl ammonium bromide or the like, or a crown ether such as 1,4,7,10-tetraoxacyclododecane, 1,4,7,10, 13-pentaoxacyclopentadecane, 1,4,7,10, 13,16-hexaoxacyclooctadecane or the like.

Reaction process formula-11

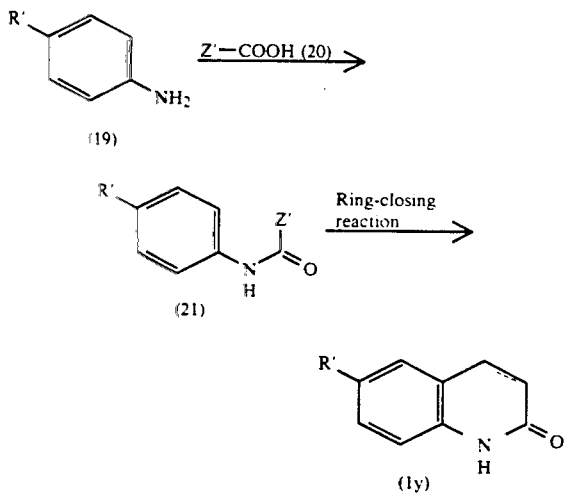

wherein R' is the same as defined above; Z' is a group of the formula R$^{25'}$—CH=CH— (wherein R$^{25'}$ is a lower alkoxy group or a halogen atom), a group of the formula

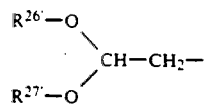

(wherein R$^{26'}$ and R$^{27'}$ are each a lower alkyl group), or a group of the formula CH≡C—.

The reaction of a compound of the general formula (19) with a compound of the general formula (20) can be carried out under conditions similar to those employed in the reaction of a compound of the general formula (1e) with a compound of the general formula (5).

The ring-closing reaction of a compound of the general formula (21) can be carried out in the presence of an acid in a suitable solvent or without the solvent. There is not any specific restriction to the acid used in this reaction, a common inorganic acid or organic acid which is known widely can be used, concretely an inorganic acid such as hydrochloric acid, hydrobromic acid, sulfuric acid and the like; a Lewis acid such as aluminum chloride, boron trifluoride, titanium tetrachloride and the like; an organic acid such as formic acid, acetic acid, ethanesulfonic acid, p-toluenesulfonic acid and the like can be exemplified. Among of these acids, hydrochloric acid, hydrobromic acid and sulfuric acid are preferably used. There is not any specific restriction to the ratio of the amount of an acid to the amount of a compound of the general formula (21), the ratio can be selected from a wide range, generally an equivalent part by weight, preferably 10 to 50 parts by weight of the acid may be used to a compound of the general formula (21). As to the solvent, any common inert solvent which is known widely can be used, for example, water, a lower alcohol such as methanol, ethanol, propanol, and the like; an ether such as dioxane, tetrahydrofuran and the like; an aromatic hydrocarbon such as benzene, toluene and the like; a halogenated hydrocarbon such as methylene chloride, chloroform, carbon tetrachloride and the like; acetone, dimethylformamide, dimethyl sulfoxide, hexamethylphosphoric triamide and the like can be exemplified. Among of these solvent, a water-soluble solvent such as a lower alcohol, an ether, aceton, dimethyl sulfoxide, dimethylformamide, hexamethylphosphoric triamide and the like are preferably used.

The reaction is generally carried out at 0° C. to 100° C., preferably at room temperature to 60° C., and is completed in about 5 minutes to 6 hours.

A compound of the general formula (12) used as the starting material in the above-mentioned Reaction process formula-6 can be prepared, for example, by the following Reaction process formula-12.

Reaction process formula-12

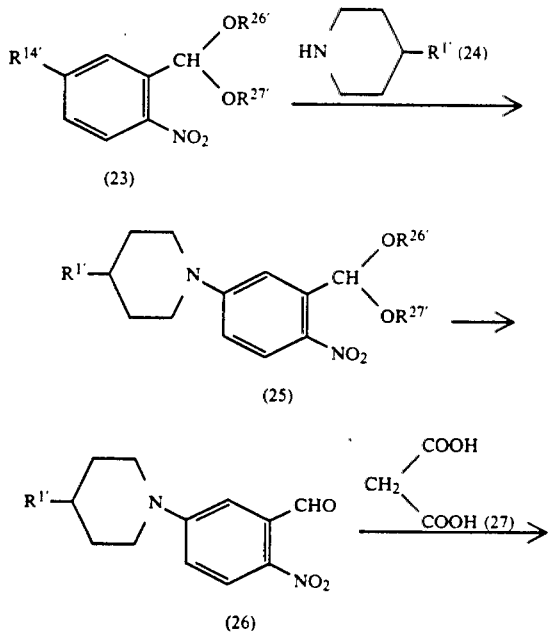

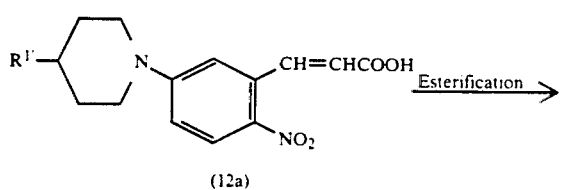

-continued
Reaction process formula-12

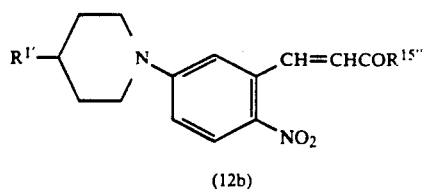

(12b)

wherein R$^{1'}$, R$^{14'}$, R$^{26'}$ and R$^{27'}$ are the same as defined above; and R$^{15''}$ is a lower alkoxy group.

The reaction of a compound of the general formula (23) with a piperidine derivative of the general formula (24) can be carried out in the presence of a solvent. As to the solvent used in the reaction, an aromatic hydrocarbon such as benzene, toluene, xylene and the like, a lower alcohol such as methanol, ethanol, isopropanol and the like, an ether such as dioxane, tetrahydrofuran, diethyl ether, ethylene glycol dimethyl ether and the like, a polar solvent such as N-methylpyrrolidone, dimethylformamide, dimethyl suloxide, hexamethylphosphoric triamide and the like can be exemplified. The reaction can advantageously be carried out by using a basic compound as the deacidifying agent. As to the basic compound, potassium carbonate, sodium carbonate, sodium hydroxide, sodium hydrogen carbonate, sodium amide, sodium hydride, a tertiary amine such as triethylamine, tripropylamine and the like, pyridine, quinoline and the like can be exemplified.

The ratio of the amount of a compound of the general formula (24) to the amount of a compound of the general formula (23) may be generally 1 to 10 times the molar quantity, preferably 3 to 7 times the molar quantity of the former to the latter. The reaction is carried out generally at 50° to 200° C., preferably at 50° to 150° C., and is completed in about 1.5 to 15 hours.

The hydrolysis reaction of a compound of the general formula (25) is carried out in a solvent for example an alcohol such as methanol, ethanol, isopropanol or the like, in the presence of a mineral acid such as hydrochloric acid, sulfuric acid or the like, at room temperature to the boiling temperature of the solvent used, and for 30 minutes to 3 hours.

The reaction of a compound of the general formula (26) with malonic acid (27) is carried out in a suitable solvent and in the presence of a bacid compound. As to the solvent used in the reaction, any solvent used in the above-mentioned reaction of a compound of the general formula (23) with a compound of the general formula (24) can also be used. Furthermore, any polar solvents including pyridine can also be used. As to the basic compound, potassium carbonate, sodium carbonate, sodium hydrogen carbonate, sodium amide, sodium hydride, a tertiary amine such as triethylamine, tripropylamine, piperidine or the like, pyridine, quinoline and the like can be exemplified. The ratio of the amount of a compound of the general formula (26) to the amount of malonic acid (27) may be at least an equimolar quantity, preferably 1 to 7 times the molar quantity of the latter may be used to the former. The reaction is carried out generally at 0° C. to 200° C., preferably at 70° C. to 150° C., and is completed in about 1 to 10 hours.

The esterification of a compound of the general formula (12a) is carried out in a solvent for example an alcohol such as methanol, ethanol, isopropanol or the like, in the presence of an acid such as hydrochloric acid or sulfuric acid or a halogenating agent such as thionyl chloride, phosphorus oxychloride, phosphorus pentachloride, phosphorus trichloride or the like, and generally at 0° C. to 150° C., preferably at 50° C. to 100° C., for about in 1 to 10 hours. The acid may be used generally in an amount of 1 to 1.2 times the molar quantity to a compound of the general formula (12a), and the halogenating agent may be used in an amount of at least an equimolar quantity, preferably 1 to 5 times the molar quantity to a compound of the general formula (12a).

Reaction process formula-13

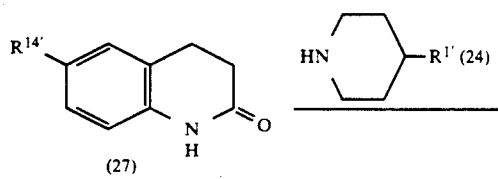

(27)

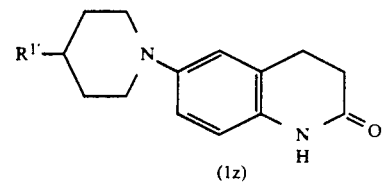

(1z)

wherein R$^{1'}$, R$^{14'}$ and the carbon-carbon bond between 3- and 4-positions in the carbostyril skeleton are the same as defined above.

The reaction of a compound of the general formula (27) with a compound of the general formula (24) is carried out generally in a suitable inert solvent, in the presence or absence of a basic condensing agent. As to the inert solvent, an aromatic hydrocarbon such as benzene, toluene, xylene, an alcohol such as methanol, ethnaol, propanol, butanol, 3-methoxy-1-butanol, ethyl cellosolve, methyl cellosolve and the like, pyridine, acetone, dimethylformamide, dimethyl sulfoxide, hexamethylphosphoric triamide and the like can be exemplified. As to the basic condensing agent, sodium carbonate, potassium carbonate, sodium hydrogen carbonate, potassium hydrogen carbonate, sodium hydroxide, potassium hydroxide, sodium hydride, potassium hydride, triethylamine and the like can be exemplified.

The ratio of the amount of a compound of the general formula (27) to the amount of a compound of the general formula (24) is not specifically restricted, and can be selected from a wide range, generally at least an equimolar quantity, preferably 1 to 5 times the molar quantity of the latter may be used to the former. The reaction is generally carried out at room temperature to 180° C., preferably at 100° C. to 150° C., and generally is completed in about 3 to 30 hours. This reaction can advantageously be proceeded by adding copper powder as the catalyst.

Reaction process formula-14

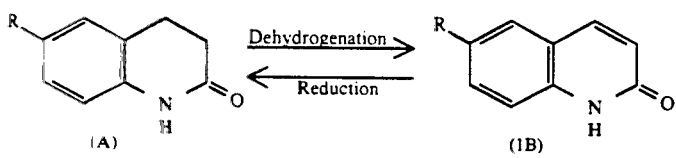

wherein R is the same as defined above.

The dehydrogenation of a compound of the general formula (1A) is carried out in a solvent by using an oxidizing agent. As to the oxidizing agent, a benzoquinone such as 2,3-dichloro-5,6-dicyanobenzoquinone, chloranil (2,3,5,6-tetrachlorobenzoquinone) and the like, a halogenating agent such as N-bromosuccinimide, N-chlorosuccinimide, bromine and the like, a dehydrogenating catalyst such as selenium dioxide, palladium carbon, palladium black, palladium oxide, Raney-nickel and the like can be exemplified. The amount of the oxidizing agent is not specifically restricted, and may be selected from a wide range, and in the case of using the halogenating agent, generally an equimolar to 5 times the molar quantity, preferably 1 to 2 times the molar quantity of the halogenating agent may be used to a compound of the general formula (1A). In the case of using the dehydrogenating catalyst, generally an excess quantity of the catalyst may be used. As to the solvent used in this reaction, an ether such as dioxane, tetrahydrofuran, methoxymethanol, dimethoxyethane and the like, an aromatic hydrocarbon such as benzene, toluene, xylene, cumene and the like, a halogenated hydrocarbon such as dichloromethane, dichloroethane, chloroform, carbon tetrachloride and the like, an alcohol such as butanol, amyl alcohol, hexanol and the like, a polar solvent such as acetic acid, and aprotic polar solvent such as dimethylformamide, dimethyl sulfoxide, hexamethylphosphoric triamide and the like can be exemplified.

The reaction is generally carried out at room temperature to 300° C., preferably at room temperature to 200° C., and is completed in about 1 to 40 hours.

The reduction of a compound of the general formula (1B) is carried out under conditions similar to those employed in usual catalytic reduction. As to the catalyst used in this reduction, palladium, palladium-carbon, platinum, Raney-nickel and the like can be exemplified. The catalyst may be used in an usual catalytic quantity. As to the solvent used in this reduction, water, methanol, ethanol, isopropanol, dioxane, tetrahydrofuran, hexane, cyclohexane, ethyl acetate and a mixed solvent of two or more of these solvents can be exemplified.

The reaction can be carried out either in an atmospheric pressure or under pressure, generally carried out in an atmospheric pressure to 20 kg/cm², preferably in an atmospheric pressure to 10 kg/cm². The reaction temperature may be generally at 0° C. to 150° C., preferably at room temperature to 100° C.

The compound of the general formula (10) which is used as the starting material in the above-mentioned Reaction process formula-4 can be prepared, for example by the method as shown in the following Reaction process formula-15.

Reaction process formula-15

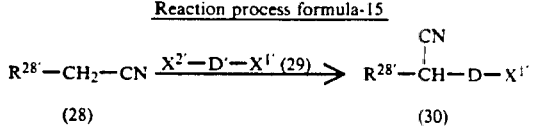

wherein $X^{1'}$ is the same as defined above; $X^{2'}$ is a halogen atom; $D'$ is a lower alkylene group; and $R^{28'}$ is a phenyl group which may have 1 to 3 substituents selected from the group consisting of a lower alkoxy group, a halogen atom and a nitro group on the phenyl ring.

The reaction of a compound of the general formula (28) with a compound of the general formula (29) can be carried out in a suitable solvent, in the presence of a basic compound. The ratio of the amount of a compound of the general formula (29) to the amount of a compound of the general formula (28) may be generally at least an equimolar quantity, preferably an equimolar to 1.5 times the molar quantity of the former to the latter. The reaction is proceeded generally at 0° C. to 150° C., preferably at room temperature to about 100° C., and is completed in 1 to 24 hours. As to the solvent used in this reaction, water, an alcohol such as methanol, ethanol, propanol, butanol, 3-methoxy-1-butanol, ethyl cellosolve, methyl cellosolve and the like, a halogenated hydrocarbon such as dichloromethane, dichloroethane, chloroform and the like, an aromatic hydrocarbon such as benzene, toluene, xylene and the like an ether such as tetrahydrofuran, diethyl ether, dimethoxyethane and the like, a ketone such as acetone, methyl ethyl ketone and the like, pyridine, acetonitrile and the like, and a mixed solvent of two or more of these solvent can be exemplified.

As to the basic compound, used in the reaction, for example an organic basic compound such as triethylamine, trimethylamine, pyridine, piperidine, dimethylaniline, N-methylmorpholine, 4-dimethylaminopyridine, DBN, DBU, DABCO, potassium acetate, sodium acetate and the like, an inorganic basic compound such as potassium carbonate, sodium carbonate, potassium hydrogen carbonate, sodium hydrogen carbonate, sodium hydroxide, sodium hydride, potassium hydride and the like, silver carbonate, an alcoholate such as sodium methylate, sodium ethylate and the like can be exemplified.

The reaction can advantageously be proceeded by adding in the reaction system a phase transfer catalyst for example, an alkyl ammonium halide such as tetra-n-butyl ammonium iodide, tetrabutyl ammonium bromide or the like, or a crown ether such as 1,4,7,10-tetraoxacyclododecane, 1,4,7,10,13-pentaoxacyclopentadecane, 1,4,7,10, 13, 16-hexaoxacyclooctadecane or the like.

Among novel carbostyril derivatives represented by the general formula (1), those having double carbon-carbon bond between 3- and 4-positions in the carbostyril skeleton capable of existing in tautomeric system in the form of lactim-lactam as shown in the following Reaction process formula-16.

Reaction process formula-16

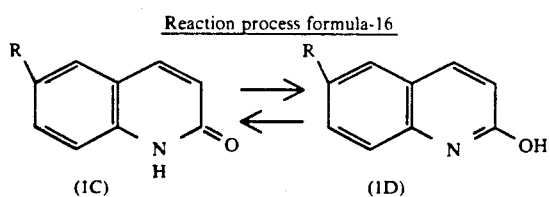

wherein R is the same as defined above.

Reaction process formula-17

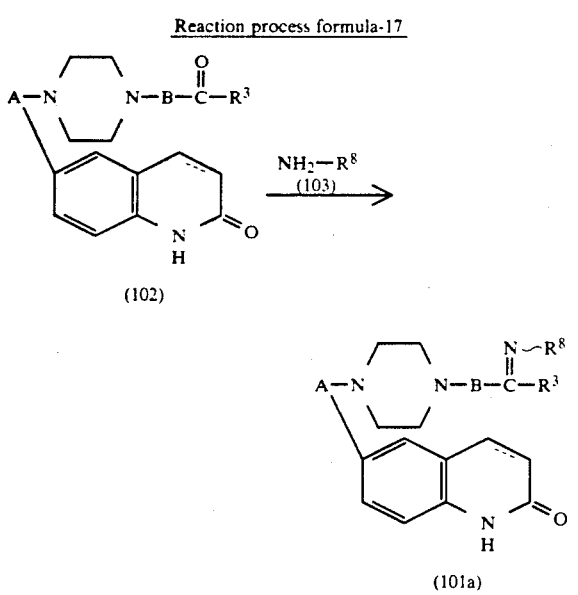

wherein A, B, $R^3$ and the carbon-carbon bond between 3- and 4-positions in the carbonstyril skeleton are the same as defined above; $R^8$ is a hydroxyl group or a lower alkoxy group.

The reaction of a compound of the general formula (102) with a compound of the general formula (103) is carried out in a suitable solvent in the presence of a basic compound. As to the solvent used in the reaction, an alcohol such as methanol, ethanol, propanol, butanol, 3-methoxy-1-butanol, ethyl cellosolve and methyl cellosolve and the like; a halogenated hydrocarbon such as methylene chloride, chloroform, dichloroethane and the like; an aromatic hydrocarbon such as benzene, toluene, xylene and the like; an ether such as diethyl ether, tetrahydrofuran, dimethoxyethane and the like; a ketone such as acetone and methyl ethyl ketone and the like; pyridine, and acetonitrile and the like; a mixed solvent of two or more of these solvents can be exemplified. As to the basic compound, an organic basic compound such as triethylamine, trimethylamine, pyridine, piperidine, dimethylaniline, N-methylmorpholine, 4-dimethylaminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO), potassium acetate and sodium acetate and the like; an inorganic basic compound such as potassium carbonate, sodium carbonate, potassium hydrogen carbonate, sodium hydrogen carbonate, sodium hydroxide, potassium hydroxide, sodium hydride and potassium hydride and the like; solver carbonate; an alcoholate such as sodium methylate and sodium ethylate and the like can be exemplified.

There in not any specific restriction to the ratio of the amount of a compound of the general formula (102) to the amount of a compound of the general formula (103), and the ratio can be selected from a wide range, generally an equimolar quantity, preferably 1 to 5 times the molar quantity of the latter may be used to the former. The reaction is generally proceeded at 0° to 150° C., preferably at about room temperature to 120° C., and is completed in 1 to 24 hours.

Reaction process formula-18

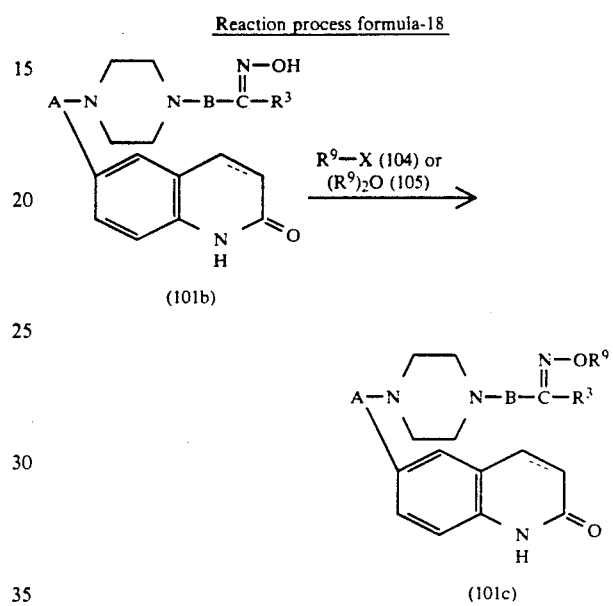

wherein A, B, $R^3$ and the carbon-carbon bond between 3- and 4-positions in the carbostyril skeleton are the same as defined above; and $R^9$ is a lower alkanoyl group; and X is a halogen atom.

The reaction of a compound of the general formula (101b) with a compound of the general formula (104) or (105) is carried out in the presence of a basic compound, and in a suitable solvent or without solvent, generally the reaction is carried out in a suitable solvent. As to the basic compound, any basic compound used in the reaction of a compound of the general formula (102) with a compound of the general formula (103) in the above-mentioned Reaction process formula-17 can also be used. As to the solvent, any solvent used in the reaction of a compound of the general formula (102) with a compound of the general formula (103) in the above-mentioned Reaction process formula-17 can also be used.

As to the ratio of the amount of a compound of the general formula (101b) to the amount of a compound of the general formula (104) or (105), at least an equimolar quantity, generally an equimolar to a large excess quantity of the latter may be used to the former. The reaction is carried out generally at 0° C. to 150° C., preferably the reaction is advantageously carried out at about 0° C. to 80° C., and is generally completed in about 0.5 to 24 hours.

Reaction process formula-19

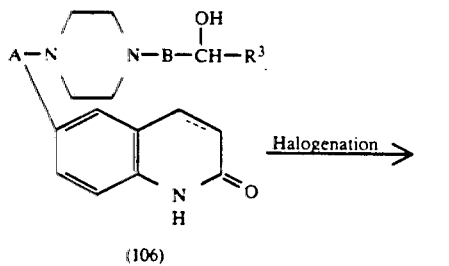

(106)

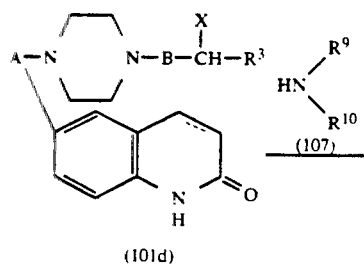

(101d)

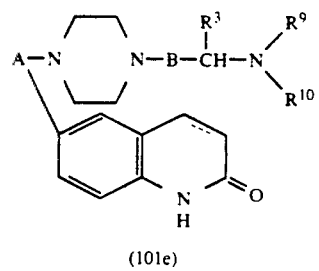

(101e)

wherein A, B, R³, X and the carbon-carbon bond between 3- and 4-positions in the carbostyril skeleton are the same as defined above; R⁹ and R¹⁰ are each the same or different and are each a hydrogen atom or a lower alkyl group; further R⁹ and R¹⁰ form together with the adjacent nitrogen atom, further with or without the additional oxygen atoms or nitrogen atom, a saturated or unsaturated 5- or 6-membered heterocyclic group.

The halogenation of a compound of the general formula (106) is carried out in a suitable solvent or without solvent, by reacting a compound of the general formula (106) with a halogenating agent. As to the solvent used in this halogenation, an aromatic hydrocarbon such as benzene, toluene, xylene and the like; a halogenated hydrocarbon such as dichloromethane, chloroform and carbon tetrachloride and the like; an ether such as dioxane, tetrahydrofuran and diethyl ether and the like; dimethylformamide (DMF), dimethyl sulfoxide (DMSO) can be exemplified. As to the halogenating agent, an usual halogenating agent which can be able to convert the hydroxyl group of the carboxyl group into a halogen atom can also be used, and thionyl chloride, phosphorus oxychloride, phosphorus oxybromide, phosphorus pentachloride and phosphorus pentabromide and the like can be exemplified.

There is not any restriction to the ratio of the amount of a compound of the general formula (106) to the amount of a halogenating agent, and it can suitably be selected from a wide range, and in the case of carrying out the halogenation in the absence of a solvent, a large excess amount of the latter is used to the former, and in the case of carrying out the halogenation in a solvent, at least an equimolar quantity, preferably 2 to 4 times the molar quantity of the latter may be used to the former. The reaction temperature and reaction time are not specifically restricted, and generally the reaction is carried out at about room temperature to 100° C., and for about in 30 minutes to 10 hours.

The reaction of a compound of the general formula (101d) with a compound of the general formula (107) is carried out in the presence or absence of a basic compound in a suitable solvent. As to the basic compound used in this reaction, any basic compound used in the reaction of a compound of the general formula (102) with a compound of the general formula (103) in the above-mentioned Reaction process formula-17 can also be used. Furthermore, as to the solvent, any solvent used in the reaction of a compound of the general formula (102) with a compound of the general formula (103) in the above-mentioned Reaction process formula can also be used.

As to the ratio of the amount of a compound of the general formula (101d) to the amount of a compound of the general formula (107), generally at least an equimolar quantity, preferably an equimolar to 10 times the molar quantity of the latter may be used to the former. The reaction is generally carried out at 0° C. to 150° C., preferably the reaction is advantageously proceeded at about room temperature to 100° C., and is generally completed in 1 to 10 hours.

Reaction process formula-20

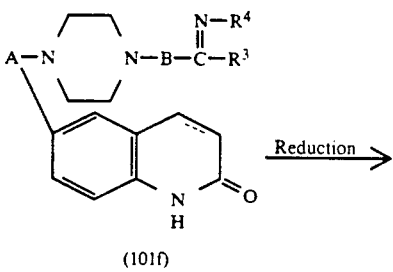

(101f)

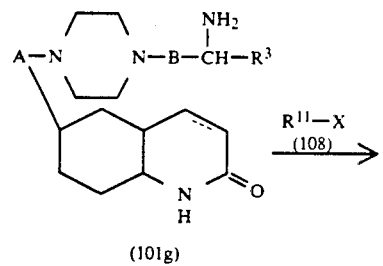

(101g)

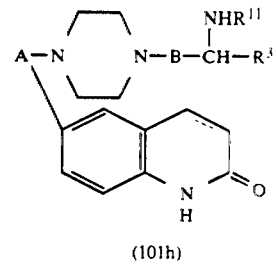

(101h)

wherein A, B, R³, X and the carbon-carbon bond between 3- and 4-positions in the carbostyril skeleton are the same as defined above; and R¹¹ is a lower alkoxycarbonyl group, a benzoyl group or a lower alkanoyl group.

The reduction of a compound of the general formula (101f) may be carried out by using a hydrogenating agent, for example a hydrogenating reducing agent such as lithium aluminum hydride, sodium borohydride or diborane or the like, and generally at least an equimolar quantity, preferably an equimolar to 10 times the molar quantity of the reducing agent to a compound of the general formula (101f) may be used. The reduction may be carried out in a suitable solvent for example, water; a lower alcohol such as methanol, ethanol or isopropanol or the like; an ether such as diethyl ether, tetrahydrofuran or diethylene glycol dimethyl ether or the like; or acetic acid, and generally at 0° C. to 200° C., preferably at 0° C. to 170° C., for 10 minutes to 10 hours. Furthermore, in the case of using lithium aluminum hydride or diborane as the reducing agent, an anhydrous solvent of diethyl ether, tetrahydrofuran or diethylene glycol dimethyl ether or the like may be used as the solvent. The reduction can be carried out under conditions as mentioned above, and preferably, the reduction may be carried out in a suitable solvent under conditions of catalytic hydrogenation. As to solvent used in this catalytic hydrogenation, water, acetic acid, an alcohol such as methanol, ethanol, isopropanol or the like; a hydrocarbon such as hexame, cyclohexane or the like, an ether such as diethylene glycol dimethyl ether, dioxane, tetrahydrofuran, diethyl ether or the like; an ester such as ethyl acetate, methyl acetate or the like; an aprotic polar solvent such as dimethyl sulfoxide or the like, and a mixed solvent of two or more of these solvent can be exemplified. As to the catalyst used in this catalytic hydrogenation, palladium, palladium-black, palladium-carbon, platinum, platinum oxide, copper chromite and Raney-nickel and the like can be exemplified. As to the amount of the catalyst, generally 0.02 to an equal amount of the catalyst to a compound of the general formula may be used. The reaction temperature is generally at about −20° C. to 100° C., preferably at about 0° C. to 70° C., and hydrogen pressure is generally under 1 to 10 atmospheric pressure, and the reaction is generally completed in 0.5 to 20 hours.

The reaction of a compound of the general formula (101g) with a compound of the general formula (108) is carried out in the presence or absence of a basic compound, and in a suitable solvent. As to the basic compound and solvent used in the reaction, any one of the basic compound and the solvent used in the reaction of a compound of the general formula (102) with a compound of the general formula (103) used in the above-mentioned Reaction process formula-17 can also be used. As to the amount of a compound of the general formula (108), at least an equimolar quantity, preferably an equimolar to 1.5 times the molar quantity thereof may be used to a compound of the general formula (101g). The reaction is generally carried out at about 0° C. to 150° C., preferably at 0° C. to 80° C., and generally is completed in 0.5 to 10 hours.

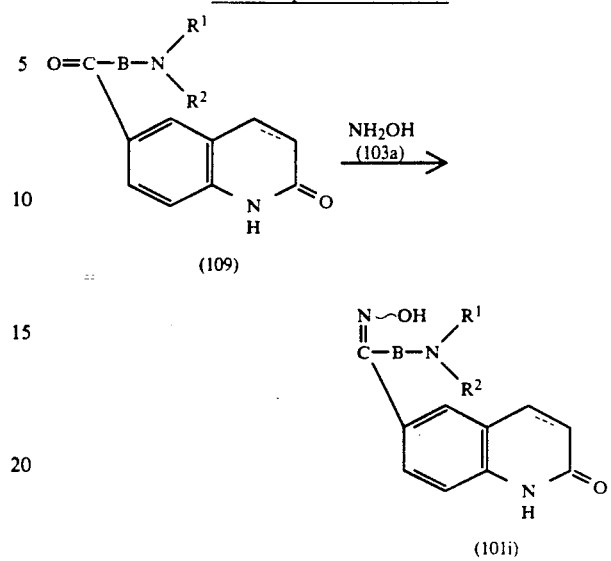

wherein $R^1$, $R^2$, B and the carbon-carbon bond between 3- and 4-positions in the carbostyril skeleton are the same as defined above.

The reaction of a compound of the general formula (109) with hydroxylamine (103a) can be carried out under conditions similar to those employed in the reaction of a compound of the general formula (102) with a compound of the general formula (103) in the above-mentioned reaction process formula-17.

Reaction process formula-22 wherein $R^1$, $R^2$ and the carbon-carbon bond between 3- and 4-positions in the carbostyril skeleton are the same as defined above.

Reaction process formula-22 as mentioned above is carried out by reacting a known carbostyril derivative of the general formula (110) or its carboxyl group-activated derivative with amine or its amino group-activated compound under a conventional amide-bond forming reaction condition.

As to the amide-bond forming reaction, the following methods can be exemplified, for example, (a) mixed acid anhydride method: e.g., a method by reacting a carbostyril derivative (110) with an alkyl halocarboxylic acid to form a mixed acid anhydride, then said mixed acid anhydride is reacted with an amine (111);

(b) activated ester method: e.g., a method by reacting an activated ester of a carbostyril derivative (110), for example p-nitrophenyl ester, N-hydroxysuccinimide ester, 1-hydroxybenztriazol ester or the like, with an amine (111);

(c) carbodiimide method: e.g., a method by condensing a carbostyril derivative (110) with an amine (111) in the presence of an activating agent, for example dicyclohexylcarbondiimide, carbonyldiimidazol or the like;

(d) other method: e.g., a method by reacting a carbostyril derivative (110) with a dehydrating agent, for example, acetic anhydride, to obtain a carboxylic acid anhydride, then the carboxylic acid anhydride is reacted with an amine (111);

(e) a method by reacting an ester being prepared from a carbostyril derivative (110) with a lower alcohol, with an amine (111) under a high pressure and at a high temperature;

(f) carboxylic acid halide method: e.g., a method by changing a carbostyril derivative (110) into an acid halide form, then said halide of carboxylic acid (110) is reacted with an amine (111);

(g) a method by activating a carbostyril derivative (110) with a phosphorus compound, for example, triphenylphosphine, diethyl cyanophosphate or diethyl chlorophosphate or the like, then said activated carbostyril derivative (110) is reacted with an amine (111).

In the mixed acid anhydride method (a), the mixed acid anhydride used in this method is obtained by a method of a conventional Schotten-Baumann reaction and generally the mixed acid anhydride is reacted with an amine (111) without being separated from the reaction mixture, to obtain a compound of the general formula (101j). The Schotten-Baumann reaction is carried out in the presence of a conventional basic compound used in this reaction, as to the basic compound, for example an organic basic compound such as triethylamine, trimethylamine, pyridine, dimethylaniline, N-methylmorpholine, 4-dimethylaminopyridine, DBN, DBU or DABCO or the like; or an inorganic basic compound such as potassium carbonate, sodium carbonate, potassium hydrogen carbonate, sodium hydrogen carbonate or the like, at a temperature of $-20°$ C. to $100°$ C., preferably at $0°$ C. to $50°$ C., in about 5 minutes to 10 hours, preferably in about 5 minutes to 2 hours. The reaction of thus obtained mixed acid anhydride with an amine (111) is carried out at about $-20°$ C. to $150°$ C., preferably at about $10°$ C. to $50°$ C., in about 5 minutes to 10 hours, preferably in about 5 minutes to 5 hours.

The above-mentioned mixed acid anhydride method is generally carried out in the absence or presence of a suitable solvent usually used in this type of mixed acid anhydride method, concretely a halogenated hydrocarbon such as methylene chloride, chloroform, dichloroethane, or the like, an aromatic hydrocarbon such as benzene, toluene, xylene or the like, an ether such as diethyl ether, tetrahydrofuran, dimethoxyethane or the like, an ester such as methyl acetate, ethyl acetate or the like, an aprotic polar solvent such as DMF, DMSO, hexamethylphosphoric triamide (HMPA) or the like. As to the alkylhalocarboxylic acid used for preparing the above-mentioned mixed acid anhydride can be exemplified such as methyl chloroformate, ethyl bromoformate, isobutyl chloroformate or the like. Generally said alkylhalocarboxylic acid is used in at least an equimolar quantity, preferably, 1 to 2 times the molar quantity thereof to the carbostyril derivative (110). The amine (111) may be generally used in at least an equimolar quantity, preferably 1 to 2 times the molar quantity of a carbostyril derivative (110).

The above-mentioned activated ester method (b), for example, in the case of using N-hydroxysuccinimide ester, the reaction is generally carried out in a suitable solvent which does not give any adverse effect to the reaction. As to the solvent, concretely, a halogenated hydrocarbon such as methylene chloride, chloroform, dichloro ethane or the like; an aromatic hydrocarbon such as benzene, toluene, xylene or the like; an ether such as diethyl ether, tetrahydrofuran, dimethoxyethane or the like or the like; an ester such as methyl acetate, ethyl acetate or the like; an aprotic polar solvent such as DMF, DMSO, HMPA or the like can be exemplified.

The reaction is carried out at temperature of $0°$ C. to $150°$ C., preferably at $10°$ C. to $100°$ C., for 5 to 30 hours. The ratio of the amount of an amine (111) to the amount of N-hydroxysuccinimide is generally at least an equimolar quantity, preferably 1 to 2 times the molar quantity of the former may be used to the latter.

In the case of conducting the carboxylic acid halide method (d) as above, that i by reacting a carboxylic acid halide with an amine (111), the reaction can be carried out in the presence of a dehydrogenating agent, and in a suitable solvent. As to the dehydrohalogenating agent, a common basic compound which is known widely can be used, for example, other than those used in conventional Schotten-Baumann reaction, sodium hydroxide, potassium hydroxide, sodium hydride, potassium hydride, silver carbonate an alcoholate such as sodium methylate, sodium ethylate and the like can be exemplified. Furthermore, an amine (111) can be used in a large excess quantity as the dehydrohalogenating agent. As to the solvent, other than those used in the above-mentioned mixed acid anhydride method (a), an alcohol such as methanol, ethanol, propanol, butanol, 3-methoxy-1-butanol, ethyl cellosolve, methyl cellosolve and the like; pyridine, acetone, acetonitrile and the like; a mixed solvent of two or more of these solvents can also be used.

There is not any specific restriction to the ratio of the amount of amine (111) to the amount of carboxylic acid halide, and it can be selected suitable from a wide range, generally at least an equimolar quantity, preferably 1 to 2 times the molar quantity of the latter may be used to the former. The reaction is generally carried out at $-30°$ C. to $180°$ C., preferably at about $0°$ C. to $150°$ C., and is completed in 5 minutes to 30 hours.

The carboxylic acid halide used in the above-mentioned reaction is prepared, for example, by reacting a carbostyril derivative (110) with a halogenating agent in the absence or presence of a solvent. As to the solvent, any solvent which does not give any adverse effect to the reaction can be used, for example, an aromatic hydrocarbon such as benzene, toluene, xylene or the like; a halogenated hydrocarbon such as chloroform, methylene chloride, carbon tetrachloride or the like; an ether such as dioxane, tetrahydrofuran, diethyl ether or the like; DMF, DMSO or the like can be exemplified.

As to the halogenating agent, any conventional halogenating agent which can be able to convert the hydroxyl group in carboxy group into halogen atom can be used, for example, thionyl chloride, phosphorus oxychloride, phosphorus oxybromide, phosphorus pentachloride, phosphorus pentabromide or the like can be exemplified.

There is not any specific restriction to the ratio of the amount of carbostyril derivative (110) to the amount of the halogenating agent, and in the case of carrying out the reaction in the absence of a solvent, generally a large excess amount of the halogenating agent may be used to the carbostyril derivative (110), on the other hand, when the reaction is carried out in the presence of a solvent, generally at least an equimolar quantity, preferably 2 to 4 times the molar quantity of the halogenating agent may be used to the carbostyril derivative (110).

The reaction temperature and reaction time are not specifically restricted, and generally the reaction is carried out at about room temperature to 100° C., preferably at 50° C. to 80° C., for about 30 minutes to 6 hours.

In the case of conducting method (g) by activating carbostyril derivative (110) with a phosphorus compound for example, triphenylphosphine or diethyl chlorophosphate or the like, then said activated carbostyril derivative (110) is reacted with an amine (111), the reaction can be carried out in a suitable solvent. As to the solvent, any solvent which does not give any adverse effect to the reaction can be used, and concretely, a halogenated hydrocarbon such as methylene chloride, chloroform, dichloroethane or the like; an aromatic hydrocarbon such as benzene, toluene, xylene or the like; an ether such as diethyl ether, tetrahydrofuran, dimethoxyethane or the like; an ester such as methyl acetate, ethyl acetate; aprotic polar solvent such as DMF, DMSO, HMPA or the like can be exemplified.

In the above-mentioned reaction, the reaction can be proceeded advantageously when an excess amount over the theoretical quantity of an amine (111) is used, since the amine (111) per se acts as the basic compound, and if necessary, other basic compound for example, an organic basic compound such as triethylamine, trimethylamine, pyridine, dimethylaniline, N-methylmorpholine, DBU, DBU, DABCO or the like; and an inorganic basic compound such as potassium carbonate, sodium carbonate, potassium hydrogen carbonate, sodium hydrogen carbonate or the like can be used.

The reaction is carried out at about 0° C. to 150° C., preferably at about 0° C. to 100° C., for about 1 to 30 hours. The ratio of the amount of carbostyril derivative (110) to the amounts of the phosphorus compound and an amine (111) may be at least an equimolar quantity, preferably 1 to 3 times the molar quantity of the latters to the former.

Reaction process formula-23

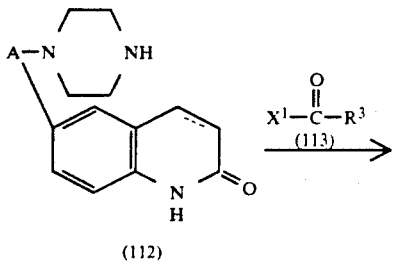

(112)

-continued
Reaction process formula-23

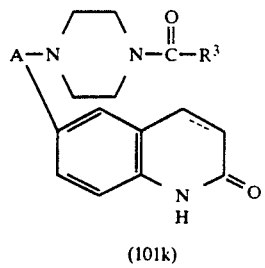

(101k)

wherein $R^3$, A and the carbon-carbon bond between 3- and 4-positions in the carbostyril skeleton are the same as defined above; and $X^1$ is a halogen atom, a lower alkanesulfonyloxy group, an arylsulfonyloxy group or an aralkylsulfonyloxy group.

The compound of the general formula (101k) is prepared by reacting a compound of the general formula (112) with a compound of the general formula (113). The reaction can be carried out under conditions and procedures similar to those employed in the reaction of a carboxylic acid halide with an amine (111) in the above-mentioned Reaction process formula-22.

In the compound represented by the general formula (113), the halogen atom being defined in symbol $X^1$ is concretely as chlorine, fluorine, bromine or iodine atom; the lower alkanesulfonyloxy group being defined in symbol $X^1$ is concretely as methanesulfonyloxy, ethanesulfonyloxy, propanesulfonyloxy, isopropanesulfonyloxy, butanesulfonyloxy, tert-butahesulfonyloxy, pentanesulfonyloxy, hexanesulfonyloxy groups or the like; the arylsulfonyloxy group being defined in symbol $X^1$ is a substituted or unsubstituted arylsulfonyloxy group, concretely phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, -naphthylsulfonyloxy groups or the like can be exemplified; further the aralkylsulfonyloxy group being defined in symbol $X^1$ is a substituted or unsubstituted aralkylsulfonyloxy group, concretely benzylsulfonyloxy, 2-phenylethylsulfonyloxy, 4-phenylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy groups or the like can be exemplified.

In the Reaction process formula-17, -19 and -21, compounds (102), (106), (109) and (112) which are used as the starting materials, respectively in these processes can be prepared by methods according to the following Reaction process formulas. Furthermore, compounds (102), (106), (109) and (112) are not only useful as the intermediates for synthesizing a compound (101), but also they possess useful pharmacological activities similar to those having by compound (101), for example, they are useful as cardiotonic agents.

Reaction process formula-24

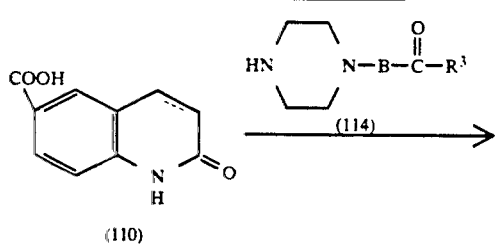

wherein $R^3$, B and the carbon-carbon bond between 3- and 4- positions in the carbostyril skeleton are the same as defined above.

The reaction of a compound of the general formula (110) the a compound of the general formula (114) can be carried out under conditions similar to those employed in the reaction of a compound (110) with a compound (111) in the above-mentioned Reaction process formula-22.

Reaction process formula-25

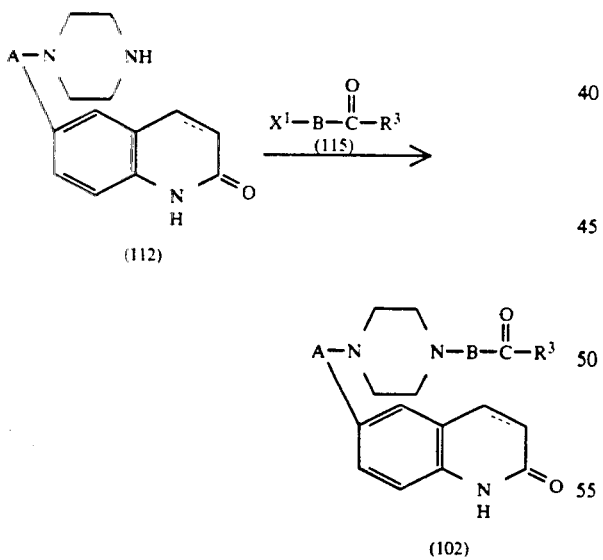

wherein $R^3$, A, B, $X^1$ and the carbon-carbon bond between 3- and 4-positions in the carbostyril skeleton are the same as defined above.

The reaction of a compound of the general formula (112) with a compound of the general formula (115) can be carried out under conditions similar to those employed in the reaction of a compound (112) with a compound (113) in the above-mentioned Reaction process formula-23.

Reaction process formula-26

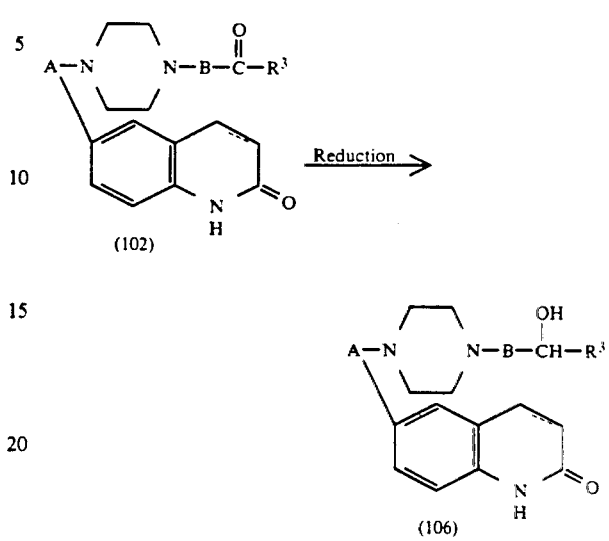

wherein $R^3$, A, B and the carbon-carbon bond between 3- and 4-positions in the carbostyril skeleton are the same as defined above.

The reduction of a compound of the general formula (102) can be carried out by various methods, and a method by using a hydrogenation reducing agent is preferably employed. As to the hydrogenation reducing agent, lithium aluminum hydride, sodium borohydride, diborane and the like can be exemplified. The amount of the hydrogenation reducing agent to the amount of compound (102) is generally at least an equimolar quantity, preferably 1 to 10 times the molar quantity of the former to the latter. The reduction is generally carried out in a suitable solvent, for example water, a lower alcohol such as methanol, ethanol, isopropanol or the like; an ether such as tetrahydrofuran, diethyl ether, diethylene glycol dimethyl ether or the like; a polar solvent such as DMF, acetic acid or the like, and generally at about $-60°$ C. to $50°$ C., preferably at about $-30°$ C. to room temperature, for about 10 minutes to 3 hours. Furthermore, when lithium aluminum hydride or diborane is used as the reducing agent, an anhydrous solvent of diethyl ether, tetrahydrofuran or diethylene glycol dimethyl ether or the like may preferably be used.

Reaction process formula-27

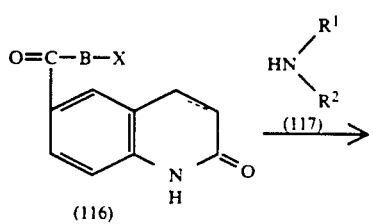

-continued
Reaction process formula-27

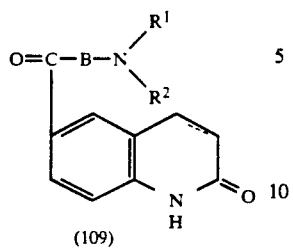

(109)

wherein $R^1$, $R^2$, B, X and the carbon-carbon bond between 3- and 4-positions in the carbostyril skeleton are the same as defined above.

The reaction of a compound of the general formula (116) with an amine derivative (117) is carried out in the absence of a solvent or generally in the presence of an inert solvent, and at about room temperature to 200° C., preferably under at room temperature to 120° C. temperature condition, and is completed in about 1 to 24 hours.

As to the inert solvent, an ether such as dioxane, tetrahydrofuran, ethyleglycol dimethyl ether, diethyl ether or the like; an aromatic hydrocarbon such as benzene, toluene, xylene or the like; a lower alcohol such as methanol, ethanol, isopropanol or the like; a polar solvent such as DMF, DMSO, HMPA, acetone, acetonitrile or the like can be used. The above-mentioned reaction is advantageously carried out by using a basic compound as the deacidifying agent. As to the basic compound, an amine derivative (117) per se being used as one of the starting materials is also included, and when said amine derivative (117) is used in an excess amount, other basic compound may not necessarily be used, and generally as to the basic compound, an inorganic basic compound such as potassium carbonate, sodium carbonate, sodium hydroxide, sodium hydrogen carbonate, sodium amide, sodium hydride or the like; an organic basic compound such as triethylamine, tripropylamine, pyridine, quinoline or the like can be used. The above-mentioned reaction can be carried out by adding an alkali metal iodide such as potassium iodide, sodium iodide or the like, or HMPA as the reaction accelerator. There is not any specific restriction to the ratio of the amount of a compound (116) to an amine derivative (117), and it can be selected suitable from a wide range, and generally an equimolar quantity to an excess quantity, preferably an equimolar quantity to 5 times the molar quantity of the latter may be used to the former.

Reaction process formula-28

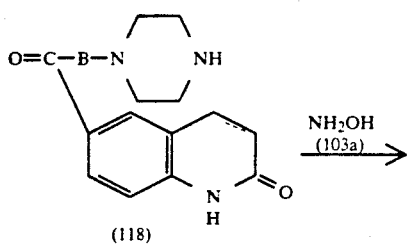

(118)

-continued
Reaction process formula-28

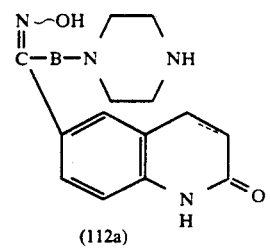

(112a)

wherein B and the carbon-carbon bond between 3- and 4-positions in the carbostyril skeleton are the same as defined above.

The reaction of a compound of the general formula (18) with hydroxylamine (103a) can be carried out under conditions similar to those employed in the reaction of a compound (102) with a compound (103) in the above-mentioned Reaction process formula-17.

Reaction process formula-29

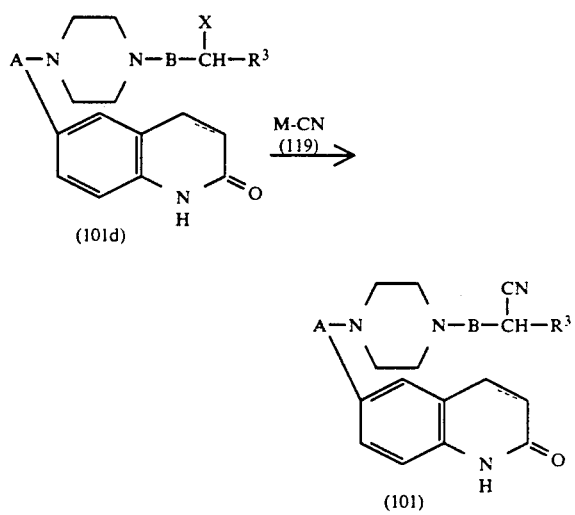

wherein $R^3$, A, B, X and the carbon-carbon bond between 3- and 4-positions in the carbostyril skeleton are the same as defined above.

The reaction of a compound of the general formula (101d) with M—CN (119) can be carried out in a suitable solvent. As to the M—CN used in this reaction, a cyanide such as potassium cyanide, sodium cyanide, silver cyanide, copper cyanide or calcium cyanide or the like can be exemplified. As to the solvent used in this reaction, water, an alcohol such as methanol, ethanol, isopropanol or the like; a halogenated hydrocarbon such as chloroform, dichloromethane, carbon tetrachloride or the like; and a polar solvent such as acetonitrile, DMF, DMSO or the like can be exemplified. The amount of M—CN (119) may be generally at least an equimolar quantity, preferably 1 to 1.5 times the molar quantity to the amount of a compound (101d).

The reaction is carried out generally at room temperature to 150° C., preferably at about 50° C. to 120° C., and is completed in about 30 minuted to 10 hours.

Furthermore, this reaction can advantageously be carried out by adding in the reaction system, a phase-transfer catalyst for example, an alkyl ammonium halide such as tri-n-butylammonium iodide, tetrabutyl ammonium bromide or the like; or a crown ether such as 1,4,7,10-tetraoxacyclododecane, 1,4,7,10, 13-pentaoxacyclopentadecane, 1,4,7,10, 13, 16-hexaoxacyclooctadecane or the like Reaction process formula-30

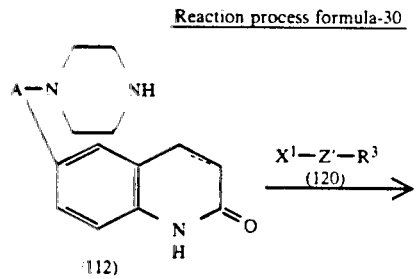

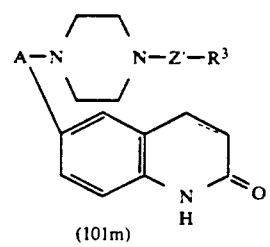

wherein $R^3$, A, B, $X^1$ and the carbon-carbon bond between 3- and 4-positions in the carbostyril skeleton are the same as defined above; and Z' is a group of the formula

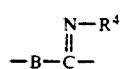

or a group of the formula

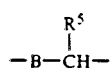

(wherein $R^4$, $R^5$ and B are the same as defined above.

The reaction of a compound of the general formula (112) with a compound of the general formula (120) can be carried out under conditions similar to those employed in the reaction of compound (116) with compound (117) in the above-mentioned Reaction process formula-27.

The compound (120) being used as one of the starting materials in the above-mentioned Reaction process formula-30 can be prepared by a method as mentioned in Reaction process formula-31 as follows.

Reaction process formula-31

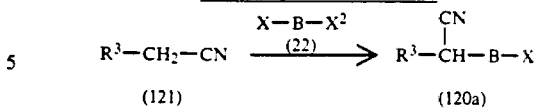

wherein $R^3$, B and X are the same as defined above; and X is a halogen atom.

The reaction of a compound of the general formula (121) with a compound of the general formula (122) can be carried out in a suitable solvent in the presence of a basic compound. As to the solvent and basic compound used in this reaction, any solvent and any basic compound which can be used in the reaction of compound (102) with compound (103) in the above-mentioned Reaction process formula-17 can also be used. The ratio of the amount of compound (122) to the amount of compound (121) may be generally at least an equimolar quantity, preferably an equimolar to 1.5 times the molar quantity of the former to the latter.

The reaction is carried out at generally at 0° C. to 150° C., preferably the reaction is advantageously proceeded at about room temperature to 100° C., and generally is completed in about 1 to 24 hours.

Further, this reaction can be proceeded advantageously by adding in the reaction system a phase transfer catalyst as mentioned in the reaction of compounded (101d) with M—CN (119) in the above-mentioned Reaction process formula-29.

Reaction process formula-32

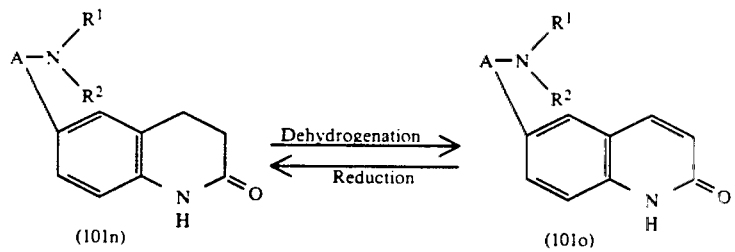

wherein $R^1$, $R^2$ and A are the same as defined above.

The reduction of a compound of (101c) can be carried out under conditions similar to those employed in common catalytic reduction. As to the catalyst used in this reduction, a metallic catalyst such as palladium, palladium-carbon, platinum, Raney-nickel or the like can be exemplified. The catalyst can be used in a usual catalytic amount. As to the solvent used in this reduction, water, methanol, ethanol, isopropanol, dioxane, tetrahydrofuran, hexane, cyclohexane, ethyl acetate, or a mixed solvent of two or more of these solvents can be exemplified.

The catalytic reduction can be carried out at either an atmospheric or under pressure, and generally at an atmospheric pressure to 20 kg/cm², preferably at an atmospheric pressure to 10 kg/cm² can be applied. Furthermore, as to the reaction temperature, generally 0° C. to 150° C., preferably at room temperature to 100° C. may be applied.

The dehydrogenation of a compound of the general formula (101n) is carried out in a suitable solvent by using an oxidizing agent. As to the oxidizing agent, a benzoquinone such as 2,3-dichloro-5,6-dicyanobenzoquinone, chloranil, (2,3,5,6-tetrachlorobenzoquinone) or the like; a halogenating agent such as N-bromosuccinimide, N-chlorosuccinimide, bromine or the like; a dehydrogenating catalyst such as selenium dioxide, palladium-carbon, palladium black, palladium oxide, Raney-nickel or the like can be exemplified. The amount of the oxidizing agent is not specifically restricted, and can be suitably selected from a wide range, and when a halogenating agent is used , generally an equimolar to 5 times the molar quantity, preferably an equimolar to 2 times the molar quantity may used to a compound (101n). Furthermore, when a dehydrogenating catalyst is used, generally an excess amount of the catalyst may be used to a compound (101n).

As to the solvent, an ether such as dioxane, tetrahydrofuran, methoxyethanol, dimethoxyethane or the like; an aromatic hydrocarbon such as benzene, toluene, xylene or the like; a halogenated hydrocarbon such as dichloromethane, dichloroethane, chloroform, carbon tetrachloride or the like; an alcohol such as butanol, amyl alcohol, hexanol or the like; a protic polar solvent such as acetic acid or the like; an aprotic polar solvent such as DMF, DMSO, HMPA or the like can be exemplified.

The reaction is carried out generally at room temperature to 300° C., preferably at room temperature to 200° C., and is completed in about 1 to 40 hours.

Among compounds represented by the general formula (101), those having double carbon-carbon bond between 3- and 4-positions in the carbostyril skeleton capable of existing in tautomeric system in the form of lactim-lactam as shown in the following Reaction process formula-33.

including diluents or excipients such as fillers, diluents, binders, wetting agents, disintegrators, surface active agents and lubricants.

No particular restriction is made to the administration unit forms and the compositions can be selected in any desired unit form, including tablets, pills, powders, liquors, suspensions, emulsions, granules, capsules, suppositories and injections (solutions and suspensions).

For the purpose to shape in the form of tablets, carriers which are known in this field can also be used, for example excipients such as lactose, sucrose, sodium chloride, glucose, urea, starch, calcium carbonate, kaolin, crystalline celluose and silicic acid; binding agents such as water, ethanol, simple syrup, solution of glucose, starch solution, gelatin solution, carboxymethyl cellulose, shelac, methyl cellulose, potassium phosphate and polyvinylpyrrolidone; disintegrators such as dried starch, sodium alginate, agar-agar powder, laminalia powder, sodium hydrogen carbonate, calcium carbonate, fatty acid easters of polyoxyethylene sorbitan, sodium laurylsulfate, monoglyceride of stearic acid, starch and lactose; disintegration inhibitors such as sucrose, stearin, coconut butter and hydrogenated oil; absorption accelerators such as quarternary ammonium base, and sodium laurylsulfate; wetting agents such as glycerin and starch; adsorbing agents such as starch, lactose, kaolin, bentonite and colloidal silicic acid; lubricants such as purified talc, stearic acid salts, boric acid powder and polyethylene glycol. In the case of preparing tablets, they can be further coated with usual coating materials to make them as sugar coated tablets, Reaction process formula-33

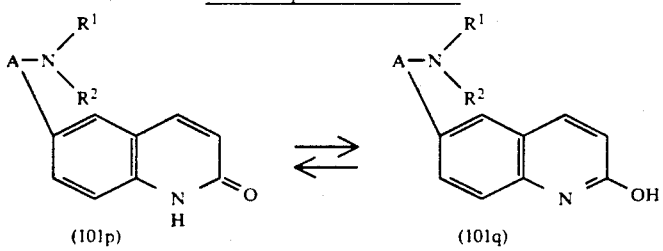

(101p)  (101q)

wherein A, $R^1$ and $R^2$ are the same as defined above.

Among the carbostyril derivatives represented by the general formula (1) according to the present invention, those having basic group can easily be converted into their acid addition salts by reacting with pharmaceutically acceptable acids. The examples of such acids including inorganic acids such as hydrochloric acid, hydrobromic acid, sulfuric acid, phosphoric acid or the like; organic acids such as oxalic acid, maleic acid, fumaric acid, malic acid, tartaric acid, citric acid, benzoic acid or the like.

The desired carbostyril derivatives as prepared by procedures in the above-mentioned various Reaction process formulas as easily be isolated and purified by usual separation means such as solvent extraction, dilution, recrystallization, column chromatography, preparative thin-layer chromatography or the like.

Carbostyril derivatives of the present invention also including their optical isomers.

Carbostyril derivatives represented by the general formula (1) according to the present invention can be used in the form of pharmaceutical composition together with usual pharmaceutically acceptable carriers. The examples of the carriers which are used depending on the desired form of pharmaceutical composition, gelatin film coated tablets, tablets coated with enteric coatings, tablets coated with films or double layered tablets, and multilayered tablets.

For the purpose to shape in the form of pills, carriers which are known and widely used in this field can also be used, for example, excipients such as glucose, lactose, starch, coconut butter, hydrogenated vegetable oils, kaolin and talc; binders such as powdered gumi arabicum, powdered tragacanth gum, gelatin and ethanol; disintegrators such as laminaria and agar-agar are included.

For the purpose to shape in the form of suppositories, carriers which are known and widely used in this field can also be used, for example, polyethylene glycols, coconut butter, higher alcohols, esters of higher alcohols, gelatin and semi-synthesized glycerides are included.

For the purpose to make in the form of injection preparations, solutions and suspensions are sterilized and are preferably isotonic to the blood. In making injection preparations, every carriers which are commonly used in this field can also be used, for example, water, ethyl alcohol, prolylene glycol, ethoxylated isostearyl alcohol, polyoxylated isostearyl alcohol and fatty acid esters of polyoxyethylene sorbitan are included. In these instances, adequate amounts of sodium chloride, glucose or glycerin can be added to contain in the desired preparations for the purpose of having them isotonic. Furthermore, usual dissolving agents, buffers, analgesic agents, preservatives can be added, as well as coloring agents, perfumes, seasoning agents, sweetening agents and other medicines can also be added into the desired injection preparations, if necessary.

The amount of a carbostyril derivative of the general formula (1) or (101) to be contained in the pharmaceutical preparation is not specifically restricted and it can suitably be selected from a wide range, and usually 1% to 70% by weight, preferably 1% to 30% by weight of the carbostyril derivative is contained in the whole composition.

The above-mentioned pharmaceutical preparation can be used in various forms depending on the purpose without any restriction, thus the pharmaceutical preparation is administered in a suitable method according to the forms of the preparation, the age of the patient, the distinction of sex, the condition of the symptoms and other factors. For example, tablets, pills, solutions, suspensions emulsions, granules and capsules are administered orally, and injection preparations are administered intravenously singly or mixed with injection transfusions such as glucose solutions and amino acids solutions; if necessary the injection preparations are administered singly intramuscularly, intracutaneously, subcutaneously or intraperitoneally; suppositories are administered into rectum.

The dosage of the pharmaceutical preparation is suitably selected according to the usage, the age of the patient, the distinction of sex, the condition of the symptoms and other factors, generally 0.01 to 10 mg/kg of body weight per day of a carbostyril derivative of the general formula (1) or (101), as the active ingredient, may be administered, and 0.1 to 200 mg of the active ingredient may be contained in the administration unit form.

The present invention will be explained more in detail by illustrating with reference to Reference Examples relating to examples of preparation of the staring materials of the objective products, Examples relating to examples of preparation of the objective products, Examples of Pharmaceutical Preparations and Pharmacological Test. However, the present in not restricted only to these examples.

REFERENCE EXAMPLE 1

4.12 Grams of 2-(4-chlorobenzoyl)ethyl chloride and 6.08 g of sodium iodide were dispersed in 50 ml of dimethylformamide, and heated at 50° C. for 1.5 hours. Then, to this dispersion was added 50 ml of dimethylformamide solution containing 3 g of 6-(1-piperazinylcarbonyl)-3,4-dihydrocarbostyril, and further 9.8 g of potassium carbonate was added thereto and reacted by heating at 70° C. for 3 to 4 hours. After the reaction was completed, the insoluble matters were removed by filtration, and the solvent in the filtrate was removed by evaporation under reduced pressure. The residue thus obtained was extracted with chloroform, and the extract was dried with anhydrous calcium sulfate, then concentrated. The thus obtained residue was purified by means of a silica gel column chromatography (eluent: dichloromethane:methanol =50:1), then recrystallized from ethanol-diethyl ether to yield 2.29 g of 6-{4-[2-(4-chlorobenzoyl)ethyl]-1-piperazinylcarbonyl}-3,4-dihydrocarbostyril. White powdery substance. Melting point: 198° C.-200° C. (decomp.)

By using suitable starting materials, and by using methods similar to those described in Reference Example 1, there were prepared compounds of Reference Example No. 2-4 as shown in the following Table 1.

TABLE 1

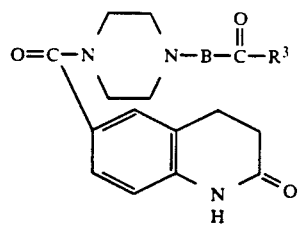

| Reference Example No. | B | $R^3$ | Crystal form (Recrystallization solvent) | Melting point (°C.) |
|---|---|---|---|---|
| 2 | —(CH$_2$)$_2$— | | White powdery substance (Ethanol-diethyl ether) | 214–215 (decomp.) |
| 3 | —(CH$_2$)$_2$— | ![](dimethoxyphenyl OCH$_3$, OCH$_3$) | White powdery substance (Methanol-diethyl ether) | 155–157 (decomp.) |

TABLE 1-continued

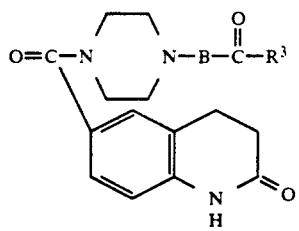

| Reference Example No. | B | R³ | Crystal form (Recrystallization solvent) | Melting point (°C.) |
|---|---|---|---|---|
| 4 | —(CH₂)₂ | 3,4-dimethoxyphenyl | Light yellow powdery substance (Methanol-diethyl ether) | 139–144 (decomp.) |

REFERENCE EXAMPLE 5

3.45 Grams of 6-carbostyril-3,4-dihydrocarbostyril and 3.1 ml of triethylamine were dissolved in 35 ml of dimethylformamide, then under stirring condition at room temperature, 5 ml of dimethylformamide solution containing 2.8 ml of isobutyl chloroformate was added dropwise to the above-mentioned solution. The whole mixture was stirred at room temperature for 1 hour, then 10 ml of dimethylformamide solution containing 5.31 g of 1-[2-(4-chlorobenzoyl)ethyl]piperazine was added dropwise to the mixture and stirred at room temperature for 10 hours. The reaction mixture was poured into an aqueous solution saturated with sodium hydrogen carbonate, then extracted with chloroform. The chloroform layer was washed with water, an aqueous solution saturated with sodium chloride in this order, then dried with anhydrous calcium sulfate. The solvent was removed by evaporation under reduced pressure, and the residue thus obtained was recrystallized from ethanol-diethyl ether to yield 3.1 g of 6-{4-[2-(4-chlorobenzoyl)ethyl]-1-piperazinylcarbonyl}-3,4-dihydrocarbostyril monohydrochloride monohydrate. White powdery substance. Melting point: 198° C.–200° C. (decomp.).

By using suitable starting materials, and by using procedures similar to those described in Reference Example 5, there were prepared compounds of the above-mentioned Reference Examples No. 2–4.

REFERENCE EXAMPLE 6

2.6 Grams of 6-4[-(2-benzoylethyl)-1-piperazinylcarbonyl]-3,4-dihydrocarbostyril was suspended in 150 ml of methanol-dimethylformamide (1:1), then to this suspension was added 0.26 g of sodium borohydride at room temperature and stirred for 1 hour. An excess amount of sodium borohydride in the reaction mixture was decomposed by adding 2M-hydrochloric acid, then the solvent was removed by evaporation. The residue thus obtained was extracted with water-ethyl acetate by means of partition extraction, the organic layer was washed with water, then dried and the solvent was removed by evaporation. The residue thus obtained was converted into a hydrochlide by adding ethanol-concentrated hydrochloric acid, and the hydrochloride was recrystallized from ethanol-water to yield 0.8 g of 6-[4-(3-phenyl)-3-hydroxypropyl)-1-piperazinylcarbonyl]-3,4-dihydrocarbosytirl monohydrochloride. Colorless powdery substance. Melting point: 236° C.–238° C.

REFERENCE EXAMPLE 7

By using a suitable starting material, and by using procedures similar to those described in Reference Example 6, there was prepared the following compound.

6-[4-(2-Phenyl-2-hydroxyethyl)-1-piperazinylcarbonyl]-3,4-dihydrocarbostyril monohydrochloride 1/2-hydrate Colorless powdery substance (from ethanol-water)
Melting point: 214° C.–223° C. (decomp.)

REFERENCE EXAMPLE 8

To 60 ml of anhydrous dimethylformamide solution containing 6.7 g of 6-(α-chloroacetyl)-3,4-dihydrocarbostyril was added 11.5 g of 4-(3-chlorobenzoyl)piperazine and 5 ml of triethylamine and the whole mixture was stirred at 50 to 60° C. for 1 hour. The reaction mixture was poured into a large amount of water, and the organic layer was extracted with chloroform. The chloroform layer was washed with water, dried, then chloroform was removed by evaporation. The residue thus obtained was recrystallized from methanol-chloroform to yield 5.5 g of 6-[4-(3-chlorobenzoyl)-1-piperazinylacetyl]-3,4-dihydrocarbostyril 1/2-hydrate in the form of colorless powdery substance. Melting point: 231° C.–234° C.

REFERENCE EXAMPLE 9

By using a suitable starting material, and by using procedures similar to those described in Reference Example 8, there was prepared compound as follows:

6-[4-(3,4-Methylenedioxybenzoyl)-1-piperazinylacetyl]-3,4-dihydrocarbostyril monohydrochloride monohydrate. Melting point: 207° C.–210° C. (recrystallized from methanol). Colorless powdery substance.

REFERENCE EXAMPLE 10

3.12 Grams of 6-[4-(1-piperazinyl)acetyl]-3,4-dihydrocarbostyril monohydrochloride trihydrate was dispersed in 30 ml of ethanol and 15 ml of water, then 2.5 g of sodium acetate and 1.2 g of hydroxylamine hydrochloride were added to the dispersion and the whole mixture was refluxed by heating for 1 hour. After the reaction was completed, the solvent was removed by evaporation under reduced pressure, then the residue thus obtained was added with an aqueous solution of potassium carbonate and then extracted with chloroform. The chloroform extract was washed with an aqueous solution saturated with sodium chloride, dried with anhydrous magnesium sulfate, then the solvent was removed by evaporation. The residue thus obtained was purified by means of a silica gel column chromatography (eluent: dichloromethane:methanol =100:1) to yield 1.5 g of 6-[2-hydroxylimino-2-(1-piperazinyl)ethyl]-3,4-dihydrocarbostyril.

REFERENCE EXAMPLE 11

Into 4 ml of benzene and 10 ml of 50% sodium hydroxide aqueous solution were added 1.2 ml of α-phenylacetonitrile, 1 ml of bromochloropropane and a catalytic amount of tri-n-butylammonium iodide, and the whole mixture was stirred at room temperature overnight under nitrogen gas stream. Then 0.5 ml of bromochloropropane was further added to the reaction mixture and reacted at 40° C. for 3 hours. After the reaction was completed, the reaction mixture was extracted with diethyl ether, and the extract was washed with an aqueous solution saturated with sodium chloride, and dried with anhydrous magnesium sulfate. The solvent was removed by evaporation under reduced pressure, and the thus obtained residue was purified by means of a silica gel column chromatography (eluent: n-hexane:ethyl acetate =5:1) to yield 1.7 g of 4-chloro-1-cyanobutylbenzene.

NMR (CDCl$_3$) δ: 1.70–2.20 (m, 4H)–3.30–3.60 (m, 3H), 3.75 (t, 1H, J=6Hz), 7.30 (s, 5H).

REFERENCE EXAMPLE 12

12 Grams of 2-nitro-5-chlorobenzaldehyde dimethyl acetal, 16.3 g of 4-acetylaminopiperidine hydrochloride, 13.7 g of sodium carbonate and 13 ml of triethylamine in 150 ml of N-methylpyrrolidone solution were mixed together and reacted by heating at 120° C. for 12 hours with stirring under nitrogen gas stream. After the reaction was completed, the solvent was removed by evaporation and thus obtained residue was added with water and extracted with dichloromethane, then the extract was washed with water and with an aqueous solution saturated with sodium chloride, then dried with anhydrous sodium sulfate. The solvent was removed by evaporation and the residue thus obtained was added with diethyl ether, then the crystals formed were collected by filtration to yield 11.2 g of 2-nitro-5-(4-acetylamino-1-piperidyl)benzaldehyde dimethylacetal.

NMR (CDCl$_3$) δ: 1.22–1.70 (2H, m), 1.86–2.17 (5H, m), 1.99 (3H, s), 2.92–3.22 (2H, m), 3.47 (6H, s), 3.76–4.20 (3H, m), 5.39 (1H, d, J=7Hz), 6.6 (1H, s), 6.78 (1H, dd, J=9Hz, J=3Hz), 7.19 (1H, d, J=3Hz), 8.02 (1H, d, J=9Hz).

REFERENCE EXAMPLE 13

0.3 Gram of 2-nitro-5-(4-acetylamino-1-piperidyl)benzaldehyde dimethylacetal, 5 ml of formalin, 1 ml of ethanol and 2 drops of concentrated hydrochloric acid were refluxed by heating. After the reaction was completed, the solvent was removed by evaporation to obtain the residue, then water was added to the residue. The crystals formed were collected by filtration to yield 0.22 g of 2-nitro-5-(4-acetylamino-1-piperidyl)benzaldehyde.

NMR (CDCl$_3$) δ1.21–1.75 (2H, m), 1.92–2.22 (2H, m), 1.99 (3H, s), 2.97–3.28 (2H, m), 3.85–4.31 (3H, m), 5.39 (1H, d, J=7Hz), 6.95 (1H, dd, J=9Hz, J=3Hz), 7.14 (1H, d, J=3Hz), 8.11 (1H, d, J=9Hz), 10.52 (1H, s).

REFERENCE EXAMPLE 14

0.22 Gram of 2-nitro-5-(4-acetylamino-1-piperidyl)benzaldehyde, 0.16 g of malonic acid, 2 ml of pyridine and 2 drops of piperidine were heated at 80° C. for 4 hours, then at 90° C. for 1 hour, under stirring. After the reaction was completed, the solvent was removed by evaporation to obtain the residue. Then, 10 ml of 0.5 N-hydrochloric acid was added to the residue and the mixture was extracted with dichloromethane, the extract was washed with water, an aqueous solution saturated with sodium chloride in this order, then dried with anhydrous sodium sulfate, and the solvent was removed by evaporation. The residue thus obtained was recrystallized from methanol-chloroform to yield 0.19 g of 2-nitro-5-(4-acetylamino-1-piperidyl)succinic acid. Yellow powdery substance. Melting point: 265° C.-268° C. (decomp.).

EXAMPLE 1

20 Grams of 6-[4-(2-benzoylethyl)-1-piperazinylcarbonyl]-3,4-dihydrocarbostyril and 5.33 g of hydroxylamine hydrochloride were dispersed in 40 ml of pyridine and the suspension was stirred at 100° C. for 4 hours. After the reaction was completed, the reaction mixture was poured into water and then extracted with chloroform, the extract was dried with anhydrous potassium carbonate, then the solvent was removed by evaporation. The thus obtained residue was purified by means of a silica gel column chromatography (eluent: dichloromethane:methanol =50:1), then recrystallized from ethanol to yield 8.79 g of 6[-4-(3-hydroxyimino-3-phenylpropyl)-1-piperazinylcarbonyl]-3,4-dihydrocarbostyril ½-hydrate. White powdery substance. Melting point: 167° C.-169° C. (decomp.)

EXAMPLE 2

1.7 Grams of 6-{4-[2-(4-chlorobenzoyl)ethyl[-1-piperazinylcarbonyl}-3,4-dihydrocarbostyril, 0.83 g of hydroxylamine hydrochloride and 2.29 g of sodium acetate were dissolved in 40 ml of ethanol and 20 ml of water, and the solution was stirred overnight at room temperature. Then the reaction mixture was concentrated under reduced pressure, then the residue thus obtained was extracted with chloroform, the extract was dried with anhydrous sodium carbonate, then the solvent was removed by evaporation. The residue thus obtained was purified by means of a silica gel column chromatography (eluent: dichloromethane:methanol =50:1), then recrystallized from ethanol to yield 1.2 g of 6-{4[-3-(4-chlorobenzoyl)-3-hydroxyiminopropyl]-1-piperazinylcarbonyl}-3,4-dihydrocarbostyril. White powdery substance. Melting point: 207° C.-209° C. (decomp.).

EXAMPLE 3

2 Grams of 6-[4-(benzoylmethyl)-1-piperazinylcarbonyl]-3,4-dihydrocarbostyril, 0.53 g of methoxylamine and 0.78 g of sodium acetate were dissolved in 10 ml of ethanol and 5 ml of water, then the solution was refluxed for 4 hours with stirring. Further, 0.53 g of methoxylamine hydrochloride and 0.78 g of sodium acetate were added to the reaction mixture, and refluxed for 2 hours with stirring. After the reaction was completed, the solvent was removed by evaporation under reduced pressure. Thus obtained residue was extracted with chloroform, and the extract was dried with anhydrous sodium carbonate, then the solvent was removed by evaporation. The residue thus obtained was purified by means of a silica gel column chromatography (eluent: dichloromethane:methanol =50:1) then the desired compound was converted into an oxalate by adding with oxalic acid in acetone, and recrystallized from ethanol-water to yield 2.6 g of 6-[4-(2-phenyl-2-methoxyiminoethyl)-1-piperazinylcarbonyl]-3,4-dihydrocarbostyril oxalate. White powdery substance. Melting point: 203° C.-205° C. (decomp.).

By using suitable starting materials and by using procedures similar to those described in Examples 1 to 3, there were prepared compounds of Examples 4-13 as shown in Table 2 as follows.

TABLE 2

General structure: A—N(R¹)(R²) substituent at 6-position of 3,4-dihydrocarbostyril

| Example No. | A | —N(R¹)(R²) | Carbon-carbon bond between 3- and 4-positions | Crystal form (Recrystallization solvent) | Melting point (°C.) | Salt form |
|---|---|---|---|---|---|---|
| 4 | —C(=O)— | —N(piperazine)N—CH₂—C(=N—OH)—C₆H₅ | Single bond | Light yellow powdery substance (Ethanol-diethyl ether) | 140-142 | — |
| 5 | —C(=O)— | —N(piperazine)N—(CH₂)₂—C(=N—OCH₃)—C₆H₅ | Single bond | White powdery substance (Ethanol-water) | 224-225 (decomp.) | Oxalate |
| 6 | —C(=O)— | —N(piperazine)N—(CH₂)₂—C(=N—OH)—C₆H₄—F | Single bond | White powdery substance (Ethanol) | 203-205 (decomp.) | — |
| 7 | —C(=O)— | —N(piperazine)N—(CH₂)₂—C(=N—OH)—C₆H₄—CH₃ | Single bond | White powdery (Ethanol) | 185-188 | — |
| 8 | —C(=O)— | —N(piperazine)N—(CH₂)₂—C(=N—OH)—C₆H₄—OCH₃ | Single bond | White powdery substance (Methanol) | 204-205 | — |
| 9 | —C(=O)— | —N(piperazine)N—(CH₂)₂—C(=N—OH)—C₆H₄—SCH₃ | Single bond | White powdery substance (Ethanol) | 125-135 (decomp.) | — |
| 10 | —C(=O)— | —N(piperazine)N—(CH₂)₂—C(=N—OH)—C₆H₃(OCH₃)₂ | Single bond | White powdery substance (Ethanol-diethyl ether) | 169-172 | — |

TABLE 2-continued

[Structure: A—N(R¹)(R²) substituent at 6-position of 3,4-dihydrocarbostyril (2-oxo) ring system]

| Example No. | A | —N(R¹)(R²) | Carbon-carbon bond between 3- and 4- positions | Crystal form (Recrystallization solvent) | Melting point (°C.) | Salt form |
|---|---|---|---|---|---|---|
| 11 | —C(O)— | —N(piperazine)N—(CH₂)₂—C(=N—OH)—(3,4-dimethoxyphenyl) | Single bond | White powdery substance (Ethanol) | 96–100 | — |
| 12 | —C(O)— | —N(piperazine)N—(CH₂)₃—C(=N—OH)—phenyl | Single bond | White powdery substance (Ethanol-dichloromethane-diethyl ether) | 192–196 (decomp.) | — |
| 13 | —C(O)— | —N(piperazine)N—(CH₂)₃—C(=N—OCH₃)—phenyl | Single bond | White powdery substance (Ethanol-water) | 210–211 (decomp.) | Oxalate |

EXAMPLE 14

5.3 Grams of 6-[4-(2-phenyl-2-hydroxyiminoethyl)-1-piperazinylcarbonyl]-3,4-dihydrocarbbstyril, 1.91 ml of acetic anhydride and 5.64 ml of triethylamine were dissolved in 60 ml of methylene chloride, and the resulting solution was stirred overnight at room temperature. After the reaction was completed, the reaction mixture was poured into water, and was made alkaline by adding sodium carbonate, then this mixture was extracted with methylene chloride. The methylene chloride extract was dried, then the solvent was removed by evaporation, and the residue was converted into an oxalate by stirring with oxalic acid in acetone. The oxalate was recrystallized from ethanol-water to yield 5.28 g of 6-[4-(2-phenyl-2-acetoxyiminoethyl)-1-piperazinyl-carbonyl-]-3,4-dihydrocarbostyril.oxalate.monohydrate. Yellow powdery substance. Melting point: 110° C.–130° C. (decomp.).

EXAMPLE 15

By using suitable starting materials and by using procedures similar to those described in Example 14, there were obtained compounds as follows:

o  6-[4-(3-Phenyl-3-acetoxyiminopropyl)-1-piperazinyl-carbonyl]-3,4-dihydrocarbostyril.oxalate White powdery substance (recrystallized from ethanol-water)

Melting point: 193° C.–194° C. (decomp.).

o 6-[4-(4-Phenyl-4-acetoxyiminobutyl)-1-piperazinylcarbonyl]-3,4-dihydrocarbostyril.oxalate.½-hydrate White powdery substance (recrystallized from ethanol-water)

Melting point: 175° C.–180° C. (decomp.).

EXAMPLE 16

5.2 Grams of 6-[4-(2-hydroxy-2-phenylethyl)-1-piperazinylcabronyl]-3,4-dihydrocarbostyril was dissolved in 100 ml of chloroform, to this solution was added dropwise 3.16 ml of thionyl chloride. The mixture was heated at 70° C. for 8 hours, then the crystals formed in the reaction mixture were collected by filtration, and recrystallized from water-ethanol to yield 3.5 g of 6-[4-(2-chloro-2-phenylethyl)-1-piperazinylcarbonyl]-3,4-dihydrocarbostyril hydrochloride. Light yellow powdery substance. Melting point: 229° C.–231° C. (decomp.).

EXAMPLE 17

By using a suitable starting material, and by using procedures similar to those described in Example 16, there was obtained compound as follows:

6-[4-(3-Chloro-3-phenylpropyl)-1-piperazinyl-carbonyl]-3,4-dihydrocarbostyril.hydrochloride Light yellow powdery substance (recrystallized from ethanol-water)

Melting point: 239° C.–241° C. (decomp.).

EXAMPLE 18

One gram of 6-[4-(3-chloro-3-phenylpropyl)-1-piperazinylcarbonyl]-3,4-dihydrocarbostyril.hydrochloride, 0.17 g of methylamine.hydrochloride and 1.2 g of potassium carbonate were dispersed in 20 ml of acetonitrile and the dispersion was stirred at 60° C. for 4 hours. After the reaction was completed, the reaction mixture was poured into water then extracted with methylene chloride. The extract was dried with anhydrous sodium carbonate, then the solvent was removed by evaporation. Thus obtained residue was purified by means of a silica gel column chromatography (eluent: dichloromethane:methanol =20:1), then the desired product was converted into a citrate, and recrystallized from ethanol-water to yield 0.5 g of 6-[4-(3-methylamino-3-phenylpropyl)-1-piperazinylcarbonyl]-3,4-dihydrocarbostyril. dicitrate. White powdery substance. Melting point: 150° C.-156° C. (decomp.).

EXAMPLE 19

3 Grams of 6-[4-(3-phenyl-3-chloropropyl)-1-piperazinylcarbonyl]-3,4-dihydrocarbostyril and 2.8 ml of pyrrolidine were dispersed in 50 ml of acetonitrile, then the dispersion was stirred at 60° C. for 4 hours. After the reaction was completed, the reaction mixture was extracted with chloroform, then the extract was dried with anhydrous sodium carbonate, and the solvent was removed by evaporation. Thus obtained residue was purified by means of a silica gel column chromatography (eluent: dichloromethane:methanol =20:1), then converted into a citrate by adding citric acid in acetone, and recrystallized from ethanol-water to yield 2.8 g of 6-{4-[3-phenyl-3-(1-pyrrolidinyl)propyl]-1-piperazinylcarbonyl}-3,4-dihydrocarbostyril dicitrate. Light yellow powdery substance. Melting point: 111° C.-119° C. (decomp.).

By using suitable starting materials, and by using procedures similar to those described in Examples 18 and 19, there were prepared compounds of Examples 20-24 as shown in Table 3 as follows.

TABLE 3

| Example No. | A | $-N\begin{matrix}R^1\\R^2\end{matrix}$ | Carbon-carbon bond between 3- and 4- positions | Crystal form (Recrystallization solvent) | Melting point (°C.) | Salt form |
|---|---|---|---|---|---|---|
| 20 | $-\overset{O}{\underset{\|}{C}}-$ | $-N\diagdown N-CH_2-CH(-C_6H_5)-N(morpholinyl)$ | Single bond | White powdery substance (Ethanol-water) | 197-198 (decomp.) | Dicitrate ½-hydrate |
| 21 | $-\overset{O}{\underset{\|}{C}}-$ | $-N\diagdown N-(CH_2)_2-CH(-C_6H_5)-N(C_2H_5)_2$ | Single bond | White powdery substance (Ethanol-water) | 165-170 (decomp.) | Dicitrate |
| 22 | $-\overset{O}{\underset{\|}{C}}-$ | $-N\diagdown N-(CH_2)_2-CH(-C_6H_5)-(imidazolyl)$ | Single bond | White powdery substance | 119-125 (decomp.) | — |
| 23 | $-\overset{O}{\underset{\|}{C}}-$ | $-N\diagdown N-(CH_2)_2-CH(-C_6H_5)-N(morpholinyl)$ | Single bond | White powdery substance (Ethanol) | 132-138 (decomp.) | Dicitrate |
| 24 | $-\overset{O}{\underset{\|}{C}}-$ | $-N\diagdown N-(CH_2)_3-CH(-C_6H_5)-NH_2$ | Single bond | White powdery substance (Ethanol-water) | 258-259 (decomp.) | Dihydrochloride ½-hydrate |

EXAMPLE 25

21. 7 Grams of 6-[-4-(4-phenyl-4-acetoxyiminobutyl)-1-piperazinylcarbonyl]-3,4-dihydrocarbostyril and 1 g of platinum oxide were dispersed in 300 ml of acetic acid, then the dispersion was hydrogenated at room temperature at an atmospheric pressure. After the hydrogenation was completed, platinum oxide was removed by filtration, then the filtrate was concentrated. The residue thus obtained was purified by means of a silica gel column chromatography (eluent: dichloromethane:methanol =20:1), then converted into hydrochloride by reacting with hydrogen chloride in ethanol, and recrystallized from ethanol-water to yield 8.5 g of 6-[4-(4-phenyl-4-aminobutyl)-1-piperazinylcarbonyl]-3,4-dihydrocarbostyril.dihydrochloride.½-hydrate. White powdery substance. Melting point: 258° C.-259° C.

EXAMPLE 26

2 Grams of 6-[4-(4-phenyl-4-aminobutyl)-1-piperazinylcarbonyl]-3,4-dihydrocarbostyril was dissolved in 30 ml of chloroform, then to this solution was added 0.76 ml of isobutyl chloroformate at 0° C.-5° C. The reaction mixture was stirred at the same temperature for 3 hours, then concentrated. The residue thus obtained was purified by means of a silica gel column chromatography (eluent: dichloromethane:methanol =40:1), then converted into an oxalate by stirring with oxalic acid in acetone, and the oxalate was recrystallized from ethanol-water to yield 1.9 g of 6-[4-(4-phenyl-4-isobutoxycarbonylaminobutyl)-1-piperazinylcarbonyl]-3,4-dihydrocarbostyril.oxalate. White powdery substance. Melting point: 221° C.-222° C.

EXAMPLES 27-28

By using suitable staring materials and by using procedures similar to those described in Example 26, there were prepared compounds of Examples 27-28 as shown in Table 4 as follows.

TABLE 4

| Example No. | A | −N(R¹)(R²) | Carbon-carbon bond between 3- and 4- positions | Crystal form (Recrystallization solvent) | Melting point (°C.) | Salt form |
|---|---|---|---|---|---|---|
| 27 | −C(=O)− | −N(piperazine)N−(CH₂)₃−CH(Ph)(NHCO-Ph) | Single bond | White powdery substance (Ethanol) | 229-230 | Oxalate. ¼-hydrate |
| 28 | −C(=O)− | −N(piperazine)N−(CH₂)₃−CH(Ph)(NHCOCH₃) | Single bond | White powdery substance (Ethanol-water) | 227-228 | Oxalate. ¼-hydrate |

EXAMPLE 29

4 Grams of 6-[4-(3-chlorobenzoyl)-1-piperazinylacetyl]-3,4-dihydrocarbostyril.hydrochloride.monohydrate acetyl]-3,4-dihydrocarbostyril.hydrochloride.monohydrate was dispersed in 390 ml of ethanol and 15 ml of water, then to this dispersion was added 2.5 g of sodium acetate and 1.2 g of hydroxylamine hydrochloride, the reaction mixture was refluxed by heating for 1 hour. After the reaction was completed, the solvent was removed by evaporation, under reduced pressure, to the residue thus obtained was added an aqueous solution of potassium carbonate, and this mixture was extracted with chloroform. The extract was washed with an aqueous solution saturated with sodium chloride, then dried with anhydrous magnesium sulfate, then the solvent was removed by evaporation. The residue thus obtained was purified by means of a silica gel column chromatography (eluent: dichloromethane →dichloromethane:methanol =10:5), then recrystallized from methanol-chloroform to yield 2.0 g of 6-{2-hydroxyimino-2-[4-(3-chlorobenzoyl)-1-piperazinyl]-ethyl}-3,4-dihydrocarbostyril. Colorless prism-like crystals. Melting point: 205° C.-207° C. (decomp.).

EXAMPLES 30-31

By using suitable starting materials and by using procedures similar to those described in Example 29, there were prepared compounds of Examples 30 and 31 as shown in Table 5 as follows.

TABLE 5

[Structure: A-N(R¹)(R²) substituted on benzene ring fused with dihydrocarbostyril ring system with N-H and C=O]

| Example No. | A | -N(R¹)(R²) | Carbon-carbon bond between 3- and 4- positions | Crystal form (Recrystallization solvent) | Melting point (°C.) | Salt form |
|---|---|---|---|---|---|---|
| 30 | -C(=N-OH)-CH₂- | -N(piperazine)N-C(=O)-[benzene]-O-CH₂-O (methylenedioxybenzoyl piperazine) | Single bond | Colorless prism-like crystals (Ethanol-chloroform) | 203–205 (decomp.) | — |
| 31 | -CCH(-C₂H₅)- with =N-OH | -N(CH₃)(CH₂-[benzene]-OCH₃) | Double bond | Colorless powdery substance (Chloroform-ethanol) | 215–216 | — |

EXAMPLE 32

127 Milligrams of succinimide 3,4-dihydrocarbostyril-6-carbostyril-6-carboxylate and 123 mg of (3-hydroxyimino-3-phenylpropyl)piperazine were dissolved in 2 ml of dimethylformamide, then this mixture was stirred for 24 hours. To the reaction mixture was added water, then extracted with chloroform and this extracted was washed with water and with an aqueous solution saturated with sodium chloride. Next, the washed extract was dried with anhydrous potassium carbonate, then the solvent was removed by evaporation under reduced pressure. The residue thus obtained was recrystallized from ethanol to yield 102 mg of 6-[4-(3-hydroxyimino-3-phenylpropyl)-1-piperazinylcarbonyl]-3,4-dihydrocarbostyril semihydrate. White powdery substance. Melting point: 167° C.-169° C. (decomp.).

By using suitable starting materials and by using procedures similar to those described in Example 32, there were prepared compounds of the above-mentioned Examples 2 to 28 and later-mentioned Examples 39–41.

EXAMPLE 33

One gram of 6-carboxy-3,4-dihydrocarbostyril, 1.3 g of dicyclohexylcarbodiimide and 1.47 g of (3-hydroxyimino-3-phneylpropyl)piperazine were suspended in 10 ml of dioxane, then the suspension was stirred at 60° C. to 70° C. for 5 hours. After the reaction was completed, the solvent was removed by evaporation, to the residue thus obtained was added ether so as to form crystals, then the crystals were removed by filtration. The mother liquor was concentrated, then the residue thus obtained was dissolved by adding chloroform, and the solution was washed with water and an aqueous solution saturated with sodium chloride, then dried with anhydrous potassium carbonate, and the solvent was removed by evaporation. The residue thus obtained was recrystallized from ethanol to yield 320 mg of 6-[4-(3-hydroxyimino-3-phenylpropyl)-1-piperazinylcarbonyl-]-3,4-dihydrocarbostyril semihydrate. White powdery substance.

Melting point: 167° C.-169° C. (decomp.)

By using suitable starting materials and by using procedures similar to those described in Example 33, there were prepared compounds of the above-mentioned Examples 2 to 28 and later-mentioned Examples 39 to 41.

EXAMPLE 34

1.6 Grams of 6-carboxy-3,4-dihydrocarbostyril and 0.8 ml of triethylamine were suspended in 10 ml of tetrahydrofuran, to this suspension was added dropwise 1.0 g of diethyl chlorophosphate in 10 ml of tetrahydrofuran solution under stirring at room temperature, and the whole mixture was further stirred at room temperature for 3 hours. To this mixture was added dropwise 1.47 g of (3-hydroxyphenylpropyl)piperazine in 10 ml of tetrahydrofuran solution, and stirred at room temperature for 10 hours. After the reaction was completed, the crystals formed in the reaction mixture were removed by filtration, then the filtrate was concentrated to obtain the residue. To the residue was poured into an aqueous solution saturated with sodium hydrogen carbonate, then extracted with chloroform. The organic layer was washed with water and an aqueous solution saturated with sodium chloride, then dried with anhydrous potassium carbonate, and the solvent was removed by evaporation. The residue thus obtained was recrystallized from ethanol to yield 1.02 g of 6-[4-(3-hydroxyimino-3-phenylpropyl)-1-piperazinylcarbonyl]-3,4-dihydrocarbostyril. semihydrate. White powdery substance. Melting point: 167° C.-169° C. (decomp.).

By using suitable starting materials and by using procedures similar to those described in Example 34, there were prepared compounds of the above-mentioned Examples 2 to 28 and later-mentioned Examples 39 to 41.

EXAMPLE 35

34.5 Grams of 6-carboxycarbostyril and 31 ml of triethylamine were dissolved in 350 ml of dimethylformamide. Under stirring condition at room temperature, 28 ml of isobutyl chloroformate in 14 ml of dimethylformamide solution was added dropwise. The reaction mixture was stirred at room temperature for 1 hour, then 49 g of geranylpiperazine in 21 ml of dimethylformamide solution was added dropwise, and the whole mixture was stirred at room temperature for 10 hours. The reaction mixture was poured into an aqueous solution saturated with sodium hydrogen carbonate, then extracted with chloroform. The chloroform layer was washed with water and an aqueous solution saturated with sodium chloride in this order, then dried with anhydrous potassium carbonate. The solvent was removed by evaporation under reduced pressure. The residue thus obtained was recrystallized from ethanol to yield 29 g of 6-[4-(3-hydroxyimino-3-phenylpropyl)-1-piperazinylcarbonyl]-3,4-dihydrocarbostyril semihydrate. White powdery substance. Melting point: 167° C.–169° C. (decomp.).

By using suitable starting materials and by using procedures similar to those described in Example 35, there were prepared compounds of the above-mentioned Examples 2 to 28 and later-mentioned Examples 39 to 41.

EXAMPLE 36

In to 100 ml of ethanol, 2.0 g of 6-ethoxycarbonyl-3,4-dihydrocarbostyril, 0.5 g of sodium ethylate and 2.12 g of geranylpiperazine were added and the mixture was reacted in an autoclave at 140° C. to 150° C. for 6 hours. After cooling, the reaction mixture was concentrated under reduced pressure, then the thus obtained residue was dissolved in 200 ml of chloroform and washed with 1%-potassium carbonate aqueous solution, diluted hydrochloric acid and water in this order, the solvent was removed by evaporation, and the residue was recrystallized from ethanol to yield 324 mg of 6-[-4-(3-hydroxyimino-3-phenylpropyl)-1-piperazinylcarbonyl]-3,4-dihydrocarbostyril.semihydrate. White powdery substance. Melting point: 167° C.–169° C. (decomp.).

By using suitable starting materials and by using procedures similar to those described in Example 36, there were prepared compounds of the above-mentioned Examples 2 to 28 and later-mentioned Examples 39 to 41.

EXAMPLE 37

1.9 Grams of 6-carboxy-3,4-dihydrocarbostyril was suspended in 200 ml of methylene chloride, then 2 ml of pyridine was added thereto. Under stirring condition, the temperature of the reaction vessel was kept at 0° C. to 20° C., 1.4 g of thionyl chloride was added dropwise. After completion of the dropwise addition, the reaction mixture was stirred at the same temperature for 1 hour, then 2.30 g of geranylpiperazine in 10 ml of methylene chloride solution was added dropwise to the reaction mixture. After completion of dropwise addition, the reaction mixture was washed sufficiently with an aqueous solution of potassium carbonate, then further washed with water and diluted hydrochloric acid, dried with anhydrous potassium carbonate then the solvent was removed by evaporation. The residue thus obtained was recrystallized from ethanol to yield 340 mg of 6-[4-(3-hydroxylimino-3-phenylpropyl)-1-piperazinyl-carbonyl]-3,4-dihydrocarbostyril.½-hydrate. White powdery substance. Melting point: 167° C.–169° C. (decomp.).

By using suitable starting materials and by using procedures similar to those described in Example 37, there were prepared compounds of the above-mentioned Examples 2 to 28 and later-mentioned Examples 39 to 41.

EXAMPLE 38

3.6 Grams of 6-(1-piperazinylcarbonyl)-3,4-dihydrocarbosytril was dispersed in 40 ml of dimethylformamide, to this dispersion was added 3.38 g of geranyl bromide and 5.1 ml of triethylamine, then the reaction mixture was stirred at room temperature for 3 hours. After the reaction was completed, the reaction mixture was poured into water and the mixture was extracted with chloroform. The extract was washed with water, and dried with anhydrous magnesium sulfate, then chloroform was removed by evaporation under reduced pressure. The residue thus obtained was recrystallized from ethanol to yield 1.8 g of 6-[4-(3-hydroxyimino-3-phenylpropyl)-1-piperazinylcarbony]-3,4-dihydrocarbostyril ½-hydrate. White powdery substance. Melting point: 167° C.–169° C. (decomp.).

By using suitable starting materials and by using procedures similar to those described in Example 38, there were prepared compounds of the above-mentioned Examples 2 to 28 and later-mentioned Examples 39 to 41.

EXAMPLE 39

500 Milligrams of 6-[4-(3-chloro-3-phenylpropyl)-1-piperazinylcabronyl]-3,4-dihydrocarbostyril was dissolved in 20 ml of dimethyl sulfoxide, then 87 g of potassium cyanide was added thereto and the mixture was stirred at 50° C. to 60° C. for 5 hours. The reaction mixture was poured into water and then extracted with chloroform. The extract was washed with water and an aqueous solution saturated with sodium chloride in this order, then dried with anhydrous magnesium sulfate and the solvent was removed by evaporation. The residue thus obtained was purified by means of a silica gel column chromatography (eluent: dichloromethane →dichloromethane:methanol = 100:5), then the desired product was converted into a hydrochloride, and recrystallized from ethanol-water to yield 100 mg of 6-[4-(3-cyano-3-phenylpropyl)-1-piperazinylcarbonyl]3,4-dihydrocarbostyril. Colorless powdery substance. Melting point: 249° C.–251° C. (decomp.).

EXAMPLE 40

3.8 Grams of 3-phenyl-3-cyanopropylmesylate was dissolved in 60 ml of dimethylformamide, then to this solution was added 4.0 g of sodium iodide and stirred at 60° C. to 70° C. for 30 minutes. Next, 5.8 g of 6-(1-piperazinylcarbonyl)-3,4-dihydrocarbostyril hydrochloride and 5.5 ml of triethylamine were added thereto and heated at 70° C. to 80° C. for 5 hours. The solvent was removed by evaporation, to the residue thus obtained was added 5%-potassium carbonate aqueous solution, then the mixture was extracted with chloroforom. The extract was washed with water, and an aqueous solution saturated with sodium chloride, and dried with magnesium sulfate. After removal of the solvent by evaporation, the residue thus obtained was purified by means of a silica gel column chromatography (eluent: dichloromethane →dichloromethane:methanol = 100:5), then the desired product was converted into a hydrochloride, recrystallized from ethanol-water to yield 2.0 g of 6-[4-(3-cyano-3-phenylpropyl)-1-piperazinylcarbonyl]-3,4-dihydrocarbostyril monohydrochloride. Colorless powdery substance. Melting point: 249° C.-251° C. (decomp.).

EXAMPLE 41

By using a suitable starting material and by procedures similar to those described in Examples 39 and 40, there was prepared the following compound.

o  6-[4-(Cyano-4-phenylbutyl)-1-piperazinyl-carbonyl]-3,4-dihydrocarbostyril.monohydrochloride Colorless prism-like crystals (from ethanol-water) Melting point: 261° C.-263° C. (decomp.).

EXAMPLE 42

3 Grams of 6-carboxy-3,4-dihydrocarbostyril and 3.5 g of 4-methylamino-1-benzylpiperidine were dispersed in 40 ml of dimethylformamide, to this dispersion was added dropwise, under ice-cooled condition, 2.61 ml of diethyl cyanophosphate and 2.39 ml of triethylamine in 10 ml of dimethylformamide solution. The reaction mixture was stirred under ice-cooled condition for 1 hour, further stirred at room temperature for 2 hours, then the reaction mixture was poured into ice-water. Said mixture was extracted with chloroform, then extract was dried with anhydrous sodium carbonate, then the solvent was removed by evaporation. The residue thus obtained was purified by means of a silica gel column chromatography, and recrystallized from acetonitrile to yield 3 g of [N-methyl-N-(1-benzyl-4-piperidyl-)amino]carbonyl]-3,4-dihydrocarbostyril.½-hydrate.

White powdery substance. Melting point: 186° C.-188° C. (decomp.)

By using suitable starting materials and by using procedures similar to those described in Example 42, there were prepared compounds of Examples 43 to 93 as shown in Table 6 as follows.

TABLE 6

| Example No. | R | Carbon-carbon bond between 3- and 4- positions | Crystal form (Recrystallization solvent) | Melting point (°C.) | Salt form |
|---|---|---|---|---|---|
| 43 | —C(O)—N(piperidyl)—N(CH₃)₂ | Single bond | White powdery substance (Ethanol-diethyl ether) | 115–120 | Dicitrate |
| 44 | —C(O)—N(piperidyl)—NHCH₂—C₆H₅ | Single bond | — | NMR[1] | ¼-Hydrate |
| 45 | —C(O)—N(piperidyl)—NHCOCH₃ | Single bond | White powdery substance (Methanol-diethyl ether) | 228–229 (decomp.) | ¼-Hydrate |
| 46 | —C(O)—N(piperidyl)—NHCO—C₆H₃(OCH₃)₂ | Single bond | White powdery substance (Ethanol-diethyl ether) | 232–233 | Free form |
| 47 | —C(O)—N(piperidyl)—NHCOOCH₂CH(CH₃)₂ | Single bond | White powdery substance (Ethanol-diethyl ether) | 130–133 | Free form |
| 48 | —C(O)—N(piperidyl)(CH₃)—N—(CH₂)₃—C₆H₅ | Single bond | Light yellow powdery substance (Ethyl acetate-diethyl ether) | 115–120 NMR[2] | Citrate. 3/2-hydrate |
| 49 | —C(O)—N(piperidyl)(CH₃)—N—(CH₂)₂—C₆H₅ | Single bond | Light yellow powdery substance (Ethyl acetate-diethyl ether) | 97–100 | Citrate. ¼-hydrate |

TABLE 6-continued

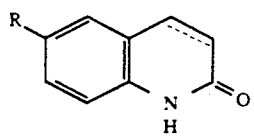

| Example No. | R | Carbon-carbon bond between 3- and 4- positions | Crystal form (Recrystallization solvent) | Melting point (°C.) | Salt form |
|---|---|---|---|---|---|
| 50 | -C(O)-N(piperidine)-N(CH₃)-(CH₂)₂-O-phenyl | Single bond | Light yellow powdery substance (Ethanol-diethyl ether) | 132-135 (decomp.) | Hydrochloride. 3/2-hydrate |
| 51 | -C(O)-N(piperidine)-N(CH₃)-CH₂-phenyl | Double bond | White powdery substance (Ethanol) | 198-200 | Free form |
| 52 | -C(O)-NH-(piperidine)-N-CH₂-phenyl | Single bond | White powdery substance (Ethanol-diethyl ether) | 198-200 | Free form |
| 53 | -C(O)-NH-(piperidine)-N-CHO | Single bond | White powdery substance (Ethanol-diethyl ether) | 246-248 (decomp.) | Free form |
| 54 | -C(O)-NH-(piperidine)-NH | Single bond | White powdery substance (Methanol) | 265-268 (decomp.) | ¼-Hydrate |
| 55 | -C(O)-NH-(piperidine)-N-(CH₂)₂-phenyl | Single bond | White powdery substance (Methanol-diethyl ether) | 258-259 (decomp.) | ¼-Hydrate |
| 56 | -C(O)-NH-(piperidine)-N-(CH₂)₃-phenyl | Single bond | White powdery substance (Methanol-diethyl ether) | 233-236 (decomp.) | ¼-Hydrate |
| 57 | -C(O)-NH-(piperidine)-N-(CH₂)₃-C(O)-phenyl | Single bond | Light yellow substance (Methanol-diethyl ether) | 217-218 (decomp.) | ¼-Hydrate |
| 58 | -C(O)-NH-(piperidine)-N-CH₃ | Single bond | White powdery substance (Methanol) | 273-275 (decomp.) | ¼-Hydrate |
| 59 | -C(O)-NH-(piperidine)-N-(CH₂)₂-O-phenyl | Single bond | Colorless plate-like substance (Methanol) | 234-235 (decomp.) | Free form |
| 60 | -C(O)-NH-(piperidine)-N-(CH₂)₂-S-phenyl | Single bond | White powdery substance (Methanol) | 252-254 (decomp.) | Free form |

TABLE 6-continued

[Structure: 6-R-substituted-3,4-dihydroquinolin-2(1H)-one]

| Example No. | R | Carbon-carbon bond between 3- and 4- positions | Crystal form (Recrystallization solvent) | Melting point (°C.) | Salt form |
|---|---|---|---|---|---|
| 61 | -C(=O)-NH-[piperidine]-N-(CH₂)₂-N(CH₃)-phenyl | Single bond | Light brawn powdery substance (Methanol) | 208-209 (decomp.) | ½-Hydrate |
| 62 | -C(=O)-NH-[piperidine]-N-(CH₂)₂-CH(CN)-phenyl | Single bond | White powdery substance (Methanol-diethyl ether) | 204-205 (decomp.) | Free form |
| 63 | -C(=O)-NH-[piperidine]-N-CH₂-(4-OCH₃-phenyl) | Single bond | White powdery substance (Methanol) | 209-210 (decomp.) | ½-Hydrate |
| 64 | -C(=O)-NH-[piperidine]-N-CH₂-(4-NO₂-phenyl) | Single bond | Light brown powdery substance (Methanol) | 252-253 (decomp.) | ¼-Hydrate |
| 65 | -C(=O)-NH-[piperidine]-N-CH₂-(4-Cl-phenyl) | Single bond | White powdery substance (Methanol) | 252-253 (decomp.) | ¼-Hydrate |
| 66 | -C(=O)-NH-[piperidine]-N-CH₂-(2,6-diCl-phenyl) | Single bond | White powdery substance (Methanol) | 185-186 (decomp.) | ½-Hydrate |
| 67 | -C(=O)-NH-[piperidine]-N-CH₂-(2-Cl-phenyl) | Single bond | White powdery substance (Methanol) | 213-214 (decomp.) | ¼-Hydrate |
| 68 | -C(=O)-NH-[piperidine]-N-CH₂-(3-Cl-phenyl) | Single bond | White powdery substance (Methanol) | 217-218 (decomp.) | ¼-Hydrate |
| 69 | -C(=O)-NH-[piperidine]-N-CH₂-(3,4-diOCH₃-phenyl) | Single bond | White powdery substance (Methanol) | 228-230 (decomp.) | Free form |

TABLE 6-continued

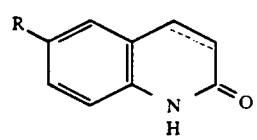

| Example No. | R | Carbon-carbon bond between 3- and 4- positions | Crystal form (Recrystallization solvent) | Melting point (°C.) | Salt form |
|---|---|---|---|---|---|
| 70 | ![structure] -C(=O)-NH-[piperidine]-N-CH(phenyl)(phenyl) | Single bond | White powdery substance (Ethanol-diethyl ether) | 116–120 | ½-Hydrate |
| 71 | -C(=O)-N(CH₃)-[piperidine]-NH | Single bond | Light yellow powdery substance (Ethanol-water) | 285–288 | Hydrochloride |
| 72 | -C(=O)-N(CH₃)-[piperidine]-N-(CH₂)₂-S-phenyl | Single bond | Colorless needle-like crystals (Methanol-water) | 255–259 (decomp.) | Hydrochloride |
| 73 | -C(=O)-N(CH₃)-[piperidine]-N-(CH₂)₂-N(CH₃)-phenyl | Single bond | Colorless needle-like crystals (Methanol-water) | 272–275 (decomp.) | Hydrochloride |
| 74 | -C(=O)-N(CH₃)-[piperidine]-N-(CH₂)₂-C(=O)-phenyl | Single bond | Colorless needle-like crystals (Methanol-water) | 269–271 (decomp.) | Hydrochloride |
| 75 | -C(=O)-N(CH₃)-[piperidine]-N-CH₂-phenyl-OCH₃ | Single bond | Colorless prism-like crystals (Methanol) | 277–280 | Hydrochloride |
| 76 | -C(=O)-N(CH₃)-[piperidine]-N-CH₂-phenyl-Cl | Single bond | Colorless prism-like crystals (Ethanol-water) | 284–288 (decomp.) | Hydrochloride |
| 77 | -C(=O)-N(CH₃)-[piperidine]-N-CH₂-C(=O)-phenyl | Single bond | Colorless needle-like crystals (Methanol-diethyl ether) | 209–214 (decomp.) | Hydrochloride |
| 78 | -C(=O)-N(CH₃)-[piperidine]-N-CH₂-phenyl-NO₂ | Single bond | Light yellow prism-like crystals (Methanol-water) | 254–258 (decomp.) | Hydrochloride |
| 79 | -C(=O)-N(CH₃)-[piperidine]-N-CH₂CH(CH₃)₂ | Single bond | Colorless needle-like crystals (Ethanol-water) | 277–280 (decomp.) | Hydrochloride. ½-hydrate |

TABLE 6-continued

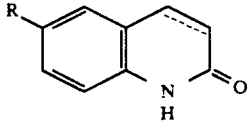

| Example No. | R | Carbon-carbon bond between 3- and 4- positions | Crystal form (Recrystallization solvent) | Melting point (°C.) | Salt form |
|---|---|---|---|---|---|
| 80 | 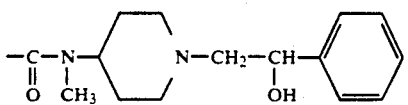 | Single bond | Colorless needle-like crystals (Ethanol-water) | 275–278 (decomp.) | Hydrochloride. ½-hydrate |
| 81 | 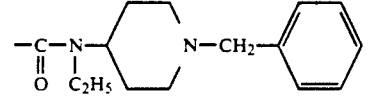 | Single bond | Colorless flake-like crystals (Ethanol-diethyl ether) | 269–273 | Hydrochloride. |
| 82 | 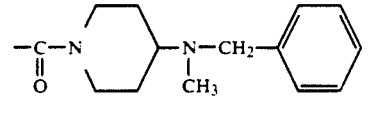 | Single bond | Yellow prism-like crystals (Isopropanol) | 163–164 | Free form |
| 83 | 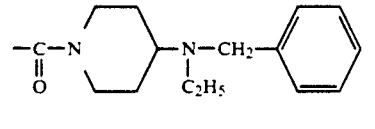 | Single bond | White powdery substance (Ethyl acetate-n-hexane) | 94–99 NMR[3] | Free form |
| 84 | 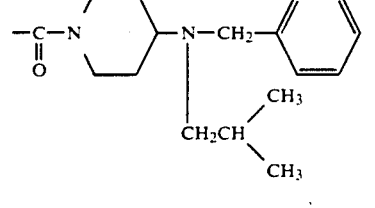 | Single bond | White powdery substance (Ethyl acetate-n-hexane) | 145–147 | Free form |
| 85 | 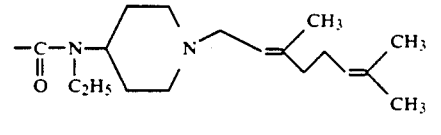 | Single bond | White powdery substance (Ethanol-water) | 265–270 (decomp.) NMR[4] | Hydrochloride. ½-hydrate |
| 86 | 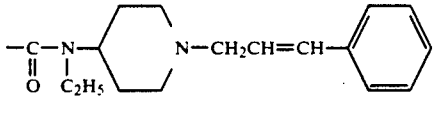 | Single bond | Colorless flake-like crystals (Ethanol-water) | 300–304 (decomp.) | Hydrochloride |
| 87 | 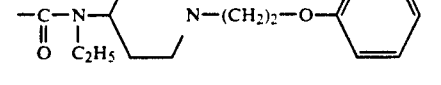 | Single bond | Colorless flake-like crystals (Ethanol-water) | 249–252 | Hydrochloride |
| 88 | 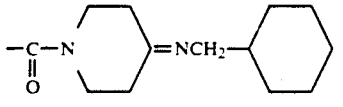 | Single bond | — | NMR[5] | Free form |
| 89 | 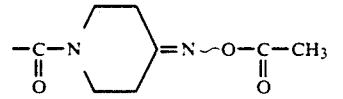 | Single bond | — | NMR[6] | Free form |

TABLE 6-continued

[Structure: 6-R-substituted 3,4-dihydrocarbostyril / carbostyril core with NH and C=O]

| Example No. | R | Carbon-carbon bond between 3- and 4-positions | Crystal form (Recrystallization solvent) | Melting point (°C.) | Salt form |
|---|---|---|---|---|---|
| 90 | —C(=O)—N(piperidyl)=O (4-oxopiperidin-1-ylcarbonyl) | Single bond | — | NMR[7] | Free form |
| 91 | —C(=O)—N(piperidyl)=N—OH | Single bond | — | NMR[8] | Free form |
| 92 | —C(=O)—N(piperidyl)—NH₂ | Single bond | — | NMR[9] | Free form |
| 93 | —C(=O)—N(piperidyl with spiro-dioxolane) | Single bond | — | NMR[10] | Free form |

NMR[1] (200 MHz, CDCl₃)δppm 1.16–2.03(6H, m), 2.50–3.08(7H, m), 3.61(2H, s), 4.17–4.58(1H, brs), 7.14–7.38(7H, m), 8.82(1H, d, J=7.7Hz), 9.32(1H, brs).
NMR[2] (200 MHz, CDCl₃)δppm 1.33–1.62(2H, m), 1.67–1.92(4H, m), 2.27(3H, s), 2.43–2.72(9H, m), 2.72–3.07(4H, m), 6.78(1H, d, J=8.0Hz), 7.13–7.34(7H, m), 8.35(1H, brs). (NMR data were determined on the free form of the product.)
NMR[3] (200 MHz, CDCl₃)δppm 1.02(3H, t, J=7.1Hz), 1.40–1.90(4H, m), 2.60(2H, q, J=7.1Hz), 2.60–3.00(7H, m), 3.64(2H, s), 3.60(1H, brs), 4.70(1H, brs), 6.80(1H, d, J=8Hz), 7.10–7.40(7H, m), 8.50(1H, brs).
NMR[4] (200 MHz, CDCl₃)δppm 1.10(3H, t, J=7Hz), 1.57(3H, s), 1.63(3H, s), 1.66(3H, s), 1.70–3.50(18H, m), 3.60(2H, brs), 3.90(1H, brs), 5.10(1H, brs), 5.30(1H, brs), 6.87(1H, d, J=8Hz), 7.15(1H, d, J=8Hz), 7.18(1H, s), 10.30(1H, s), 10.4(1H, brs).
NMR[5] (200 MHz, CDCl₃)δppm 1.93–2.20(4H, m), 2.44–2.72(6H, m), 2.95–3.06(2H, m), 3.67–3.97(4H, m), 6.83–6.90(1H, m), 7.21–7.36(8H, m), 8.93(1H, brs).
NMR[6] (200 MHz, CDCl₃)δppm 2.18(3H, s), 2.50–2.80(6H, m), 3.01(2H, t, J=8.1Hz), 3.77(4H, m), 6.80(1H, d, J=8.0Hz), 7.25–7.32(2H, m), 8.18(1H, brs).
NMR[7] (200 MHz, CDCl₃)δppm 2.37–2.49(4H, m), 2.55–2.63(2H, m), 2.89–2.98(2H, m), 3.77–3.92(4H, m), 6.87(1H, d, J=8.0Hz), 7.21–7.29(2H, m), 9.87(1H, brs).
NMR[8] (90 MHz, DMSO-d₆)δppm 2.20–2.63(6H, m), 2.79–3.02(2H, m), 3.20–3.68(5H, m), 6.88(1H, d, J=9Hz), 7.13–7.30(2H, m), 10.22(1H, brs).
NMR[9] (250 MHz, DMSO-d₆)δppm 1.26(2H, m), 1.82(2H, m), 2.43–2.53(2H, m), 2.89–3.10(3H, m), 4.37(6H, m), 6.90(1H, d, J=8.0Hz), 7.16–7.22(2H, m), 10.27(1H, brs).
NMR[10] (250 MHz, DMSO-d₆)δppm 1.65(4H, m), 2.46–2.54(2H, m), 2.89–2.95(2H, m), 3.54(4H, m), 3.93(4H, s), 6.88(1H, d, J=8.0Hz), 7.21–7.27(2H, m), 10.26(1H, s).

EXAMPLE 94

1.25 Grams of methyl 3-[4-(N-methylacetylamino)-1-piperidyl]-6-nitrocinnamate was dissolved in 50 ml of ethanol, then 0.4 g of 10%-palladium carbon was added thereto, the reaction mixture was stirred until the absorption of hydrogen gas was stopped under conditions of at room temperature and normal pressure. The catalyst was removed by filtration, the filtrate was concentrated by evaporating the solvent, the residue thus obtained was purified by means of a silica gel column chromatography (eluent: dichloromethane: methanol = 50:1), then recrystallized from methanol-diethyl ether to yield 0.82 g of 6-[4-(N-methylacetylamino)-1-piperidyl]-3,4-dihydrocarbostyril. Light yellow needle-like crystals. Melting point: 195° C.-197° C.

By using suitable starting materials, and by procedures similar to those described in Example 94, there were prepared compounds of Examples 95 to 105 as shown in Table 7 as follows.

TABLE 7

[Structure: 6-R-substituted carbostyril core]

| Example No. | R | Carbon-carbon bond between 3- and 4-positions | Crystal form (Recrystallization solvent) | Melting point (°C.) | Salt form |
|---|---|---|---|---|---|
| 95 | —N(piperidyl)—NH—C(=O)—OC₂H₅ | Single bond | Colorless needle-like crystals (Ethanol) | 219–221 | Free form |

TABLE 7-continued

| Example No. | R | Carbon-carbon bond between 3- and 4- positions | Crystal form (Recrystallization solvent) | Melting point (°C.) | Salt form |
|---|---|---|---|---|---|
| 96 | −N⟩−NH−SO₂CH₃ | Single bond | Light yellow flake-like crystals (Methanol) | 197–200 | Free form |
| 97 | −N⟩−N(CH₃)−C(=O)−C₆H₃(OCH₃)₂ | Single bond | Colorless prism-like crystals (Ethanol) | 206–208 | Free form |
| 98 | −N⟩−N(CH₃)−C(=O)−OC₂H₅ | Single bond | Colorless needle-like crystals (Ethanol-diethyl ether) | 158–160.5 | Free form |
| 99 | −N⟩−NH−C(=O)−O−CH₂CH(CH₃)₂ | Single bond | Light yellow needle-like crystals (Ethanol-diethyl ether) | 204–206 | Free form |
| 100 | −N⟩−NH−C(=O)−C₆H₃(OCH₃)₂ | Single bond | Colorless needle-1 like crystals (Ethanol-chloroform) | 277–279 (decomp.) | Free form |
| 101 | −N⟩−NH−C(=O)−CH=CH−C₆H₃(OCH₃)₂ | Single bond | Light yellow prism-like crystals (Ethanol-chloroform) | 249–252 | ½-Hydrate |
| 102 | −N⟩−NH−C(=O)−C₆H₄−Cl | Single bond | Colorless needle-like crystals (Ethanol-chloroform) | 250–253 | Free form |
| 103 | −N⟩−NH−C(=O)−C₆H₅ | Single bond | Light yellow needle-like crystals (Ethanol-chloroform) | 281–284 (decomp.) | Free form |
| 104 | −N⟩−NH−C(=O)−(CH₂)₂−C₆H₅ | Single bond | Colorless needle-like crystals (Ethanol-chloroform) | 216–219 | Hydrochloride. ½-hydrate |
| 105 | −N⟩−NH−C(=O)−CH₃ | Single bond | Light yellow powdery substance (Methanol-diethyl ether) | 235–238 (decomp.) | ½-Hydrate |

EXAMPLE 106

A mixture of 1 g of 6-(4-amino-1-piperidyl)carbonyl-3,4-dihydrocarbostyril, 1 ml of 98%-formic acid and 0.7 ml of 35%-formalin was stirred at 100° C. for 3 hours, then the solvent was removed by evaporation under reduced pressure. The residue thus obtained was dispersed in water and the dispersion was made alkaline by adding sodium carbonate, then extracted with chloroform and the extract was dried with anhydrous sodium carbonate, then the solvent was removed by evaporation. The residue thus obtained was purified by means of a middle-pressure liquid chromatography (eluent: chloroform:methanol = 100:1), then the desired product was converted into a citrate, and recrystallized from ethanol:diethyl ether to yield 0.8 g of 6-(4-dimethylamino-1-piperidyl)carbonyl-3,4-dihydrocarbostyril.dicitrate. White powdery substance. Melting point: 115° C.-120° C.

EXAMPLE 107

0.8 Gram of 6-(4-oxo-1-piperidyl)carbonyl-3,4-dihydrocarbostyril, 1.6 ml of benzylamine and 1 g of Molecular Sieve 3A (a trademark for synthetic feldspar manufactured by Linde Co., U. S. A.) were dispersed in 15 ml of chloroform and refluxed by heating for 6 hours. Molecular Sieve 3A was removed by filtration, the filtrate was concentrated, then the residue obtained was washed several times with diethyl ether, next, purified by means of a silica gel column chromatography to obtain 6-(4-benzylimino-1-piperidyl)carbonyl-3,4-dihydrocarbostyril.

Thus obtained 6-(4-benzylimino-1-piperidyl)-carbonyl-3,4-dihydrocarbostyril was dissolved in 30 ml of methanol, then 1 g of sodium borohydride was added thereto gradually, and the reaction mixture was stirred at room temperature overnight. The reaction mixture was poured into ice-diluted hydrochloride acid mixture, then the whole mixture was made alkaline by adding sodium carbonate, then extracted with chloroform, the extract was dried with anhydrous sodium carbonate, then the solvent was removed by evaporation. The residue thus obtained was purified by means of a thin-layer chromatography (developing agent: chloroform:methanol = 10:1) to yield 0.2 g of 6-(4-benzyl-amino-1-piperidyl)carbonyl-3,4-dihydrocarbostyril ½-hydrate.

NMR (200 MHz, CDCl$_3$) δppm: 1.16–2.03 (6H, m), 2.50–3.08 (7H, m), 3.61 (2H, s), 4.17–4.58 (1H, brs), 8.82 (1H, d, J=7.7Hz), 7.14–7.38 (7H, m), 9.32 (1H, brs).

EXAMPLE 108

200 Mg of palladium black was dispersed in 10 ml of 4.4%-formic acid, to this dispersion was added 200 mg of 6-(1-benzyl-4-piperidylamido)-3,4-dihydrocarbostyril, then the mixture was stirred at room temperature for 30 minutes under argon gas stream. After the reaction was completed, the catalyst was removed by filtration, then the filtrate was concentrated. The residue thus obtained was purified by means of a silica gel column chromatography (eluent: dichloromethane:methanol = 10:1), then recrystallized from ethanol-diethyl ether to yield 150 mg of 6-(1-formyl-4-piperidylamido)-3,4-dihydrocarbostyril. White powdery substance. Melting point: 246° C.-248° C. (decomp.).

EXAMPLE 109

1.9 Grams of 6-(1-benzyl-4-piperidylamido)-3,4-dihydrocarbostyril and 150 mg of platinum oxide were dispersed in 40 ml of acetic acid, then hydrogenized at 80° C. to 100° C. After the reaction was completed, the catalyst was removed by filtration, the filtrate was concentrated. The residue obtained was purified by means of a silica gel (being treated to neutralize with sodium hydrogen carbonate) chromatography (eluent: dichloromethane:methanol = 5:1), recrystallized from methanol to yield. 0.8 g of 6-(4-piperidylamido)3,4-dihydrocarbostyril ½-hydrate. White powdery substance. Melting point: 265° C.-268° C. (decomp.).

EXAMPLE 110

1.1 Grams of 6-(4-piperidylamido)-3,4-dihydrocarbostyril and 1.12 ml of triethylamine were dissolved in 20 ml of acetonitrile, to this solution was added 0.88 ml of p-methoxybenzyl chloride, and stirred at room temperature overnight. The reaction mixture was poured into water and extracted with chloroform. The chloroform extract was dried with anhydrous sodium carbonate, then the solvent was removed by evaporation. The residue thus obtained was recrystallized from methanol to yield 1.2 g of 6-[1-(4-methoxybenzyl)-4-piperidylamido]-3,4-dihydrocarbostyril. ½-hydrate. White powdery substance. Melting point: 209° C.-210° C. (decomp.).

By using suitable starting materials and by procedures similar to those described in Example 110, there were prepared compounds of the above-mentioned Examples 42–44, 48–52, 55–62, 64–70, 72–87 and 96.

EXAMPLE 111

2 Grams of 6-(4-amino-1-piperidylcarbonyl)-3,4-dihydrocarbostyril and 3.06 ml of triethylamine were dispersed in 40 ml of methylene chloride, then under ice-cooling conditions, 0.78 ml of acetyl chloride was added dropwise thereto, and stirred at room temperature for 4 hours. The reaction mixture was poured into an aqueous solution saturated with sodium chloride, then extracted with chloroform. The extract was dried with anhydrous sodium carbonate, the solvent was removed by evaporation. The residue thus obtained was purified by means of a silica gel column chromatography (eluent: dichloromethane:methanol = 10:1), then recrystallized from methanol-diethyl ether to yield 0.3 g of 6-(4-acetylamino-1-piperidylcarbonyl)-3,4-dihydrocarbostyril.¼-hydrate. White powdery substance. Melting point: 228° C.-229° C. (decomp.).

By using suitable starting materials and by procedures similar to those described in Example 111, there were prepared compounds of Examples 45–47, 53, 94–95 and 97–105.

EXAMPLE 112

(a) 16 Grams of p-[4-(N-methylacetylamino)-1-piperidyl]aniline was dissolved in 150 ml of toluene then to this solution was added 9.12 ml of triethylamine. Next, 11 g of β-bromopropionyl chloride in 30 ml of toluene solution was added dropwise thereto under stirring at 80° C. The reaction was continued further for 30 minutes, then the resinous materials formed in the reaction mixture were removed, then the remaining liquid was washed with water, dried and the solvent was removed by evaporation to yield 18 g of N-(β-bromopropionyl)-p-[4-(N-methylacetylamino)-1-piperidyl]-aniline as in the form of an oily substance.

(b) 2.7 Grams of N-(β-bromopropionyl)-p-[4-(N-methylacetylamino)-1-piperidyl]aniline and 28 g of pulverized aluminum chloride were suspended in 50 ml of carbon disulfide, then the mixture was refluxed by heating for 4 hours. The reaction mixture was poured into ice-water, then the precipitates formed were collected and washed with water, and with diethyl ether, then this substance was converted into a hydrobromide and recrystallized from methanol-diethyl ether to yield 0.8 g of 6-[4-(N-methylacetylamino)-1-piperidyl]-3,4-dihydrocarbostyril. Light yellow needle-like crystals. Melting point: 195° C.-197° C.

By using suitable starting materials and by procedures similar to those described in Example 112, there were prepared compounds of Examples 42-50, 52-93 and 95-105.

EXAMPLE 113

(a) 10.4 Grams of p-[4-(N-methyl-N-benzylamino)-1-piperidylcarbonyl]aniline was dissolved in 100 ml of benzene, to this solution was added 4.56 ml of triethylamine. Next, under refluxing conditions, 3.94 g of -methoxyacrylic chloride in 20 ml of benzene solution was added dropwise to the reaction mixture. After the dropwise addition was finished, the reaction mixture was further refluxed for 1 hour. After the reaction was completed, the reaction mixture was washed with water, dried and the solvent was removed by evaporation. The residue thus obtained was purified by means of a silica gel column chromatography to yield 8 g of N-($\beta$-methoxyacryloyl-p-[4-N-methyl-N-benzylamino)-1-piperidylcarbonyl]aniline.

(b) 4.79 Grams of N-(8-methoxyacryloyl)-p-[4-N-methyl-N-benzylamino)-1-piperidylcarbonyl]aniline was added to 50 ml of 60%-sulfuric acid with stirring at room temperature, the reaction was continued for 2 hours. The reaction mixture was neutralized with 10 N-sodium hydroxide aqueous solution, then the precipitates formed were collected by filtration, washed with water, and recrystallized from ethanol to yield 200 mg of 6-[4-(N-methyl-N-benzylamino)-1-piperidylcarbonyl]carbostyril. White powdery substance. Melting point: 198° C.-200° C.

EXAMPLE 114

5.6 Grams of 6-bromo-3,4-dihydrocarbostyril, 1.8 g of 4-(N-methylacetylamino)-1-piperidine, 1.8 g of potassium carbonate and 0.2 g of copper powder were admixed with 60 ml of 3-methoxybutanol, and the mixture was refluxed for 5 hours. The reaction mixture was filtered and the thus obtained filtrate was concentrated to dryness under reduced pressure, the residue thus obtained was extracted with methanol-chloroform. The chloroform layer was concentrated by evaporation and the residue obtained was purified by means of preparative silica gel thin layer chromatography. Recrystallized from methanol-diethyl ether to yield 450 mg of 6-[4-(N-methylacetylamino)-1-piperidyl]-3,4-dihydrocarbostyril. Light yellow needle-like crystals.

Melting point: 195° C.-197° C.

By using suitable starting materials and by procedures similar to those described in Example 114, there were prepared compounds of examples 95-105.

2.7 Grams of 6-[-N-(1-benzoylmethyl-4-piperidyl)-N-methylamido]-3,4-dihydrocarbostyril was suspended in 150 ml of methanol-dimethylformamide (1:1), then 0.26 g of sodium borohydride was added thereto at room temperature and stirred for 1 hour. The excess sodium borohydride was decomposed by adding 2M-hydrochloric acid, then the solvent was removed by evaporation. The residue was participated with water-ethyl acetate, and the organic layer was washed with water, dried and the solvent was removed by evaporation. The residue thus obtained was converted into a hydrochloride by using ethanol-concentrated hydrochloric acid, and recrystallized from ethanol-water to obtain 0.8 g of 6-{N-[1-(2-phenyl-2-hydroxyethyl)-4-piperidyl]-N-methylamido}-3,4-dihydrocarbostyril.monohydrochloride.¼-hydrate. Colorless needle-like crystals. Melting point: 275° C.-278° C. (decomp.).

EXAMPLE 116

4.7 Grams of 6-[N-(-4-piperidyl)-N-methylamido]-3,4-dihydrocarbostyril and 1.79 g of 2-phenylepoxide in 30 ml of N-methylpyrrolidone solution were heated at 100 to 110° C. for 11 hours with stirring. After the reaction was completed, the solvent was removed under reduced pressure, the residue thus obtained was purified by means of a silica gel column chromatography (eluent: dichloromethane: methanol =25:1), then converted into hydrochloride by using ethanol-concentrated hydrochloric acid, and recrystallized from ethanol-water to yield 2.9 g of 6-{N-[1-(2-hydroxy-2-phenylethyl)-4-piperidyl]-N-methylamido}-3,4-dihydrocarbostyril.monohydrate ¼-hydrate. Colorless needle-like crystals. Melting point: 275° C.-278° C. (decomp.).

EXAMPLE 117

37 Grams of 6-(4-oxo-1-piperidylcarbonyl)-3,4-dihydrocarbostyril, 30.3 g of hydroxylamine.hydrochloride and 83.5 g of sodium acetate were dissolved in 600 ml of ethanol and 300 ml of water, the mixture was stirred overnight at room temperature. The crystals precipitated were collected by filtration, and recrystallized from ethanol to yield 16 g of 6-(4-hydroxylimino-1-piperidylcarbonyl)-3,4-dihydrocarbostyril.

NMR (90 MHz, DMSO-$d_6$) $\delta$ppm: 2.20-2.63 (6H, m), 2.79-3.02 (2H, m), 3.20-3.68 (5H, m), 6.88 (1H, d, J=9Hz), 7.13-7.30 (2H, m), 10.22 (1H, brs).

EXAMPLE 118

15 Grams of 6-(4-hydroxyimino-1-piperidylcarbonyl)-3,4-dihydrocarbostyril, 11.4 ml of acetic anhydride and 31.8 ml of triethylamine in 300 ml of methylene chloride solution were mixed together and stirred at room temperature overnight. The reaction mixture was poured into ice-water, and extracted with chloroform. The chloroform extract was dried with anhydrous sodium carbonate, then the solvent was removed by evaporation to yield 16.5 g of 6-(4-acetyloxyimino-1-piperidylcarbonyl)-3,4-dihydrocarbostyril.

NMR (200 MHz, CDCl$_3$) $\delta$ppm: 2.18 (3H, s), 2.50-2.80 (6H, m), 3.01 (1H, t, J=8.1Hz), 3.77 (4H, m), 6.80 (1H, d, J=8.0Hz), 7.25-7.32 (2H, m), 8.18 (1H, brs).

EXAMPLE 119

10 Grams of 6-(4-acetyloxyimino-1-piperidylcarbonyl)-3,4-dihydrocarbostyril and 0.5 g of platinum oxide were dispersed in 150 ml of acetic acid, then the mixture was catalytically reduced at room temperature under normal pressure. The catalyst was removed by filtration, then the filtrate was concentrated under reduced pressure by evaporating the solvent, the residue thus obtained was purified by means of a silica gel column chromatography (eluent: dichloromethane:methanol = 10:1) to yield 3 g of 6-(4-amino-1-piperidylcarbonyl)-3,4-dihydrocarbostyril.

NMR (250 MHz, DMSO-d$_6$) δppm: 1.26 (2H, m), 1.82 (2H, m), 2.43–2.53 (2H, m), 2.89–3.10 (3H, m), 4.37 (6H, m), 6.90 (1H, d, J=8.0Hz), 7.16–7.22 (2H, m), 10.27 (1H, brs).

EXAMPLE 120

46 Grams of 6-(4,4-ethylenedioxy-1-piperidylcarbonyl)-3,4-dihydrocarbostyril was dispersed in 400 ml of dioxane and 150 ml of water, then 15 ml of concentrated hydrochloric acid was added thereto and the whole mixture was heated at 100° C. for 7 hours with stirring. After the reaction mixture was allowed to stand for cooling, then was made alkaline by adding sodium carbonate, and the solvent was removed by evaporation. The residue thus obtained was extracted with chloroform, and the extract was dried with anhydrous sodium carbonate, and the solvent was removed by evaporation. The residue thus obtained was purified by means of a silica gel column chromatography (eluent: dichloromethane:methanol =10:1) to yield 37.6 g of 6-(4-oxo-1-piperidylcarbonyl)-3,4-dihydrocarbostyril.

NMR (200 MHz, CDCl$_3$) δppm: 2.37–2.49 (4H, m), 2.55–2.63 (2H, m), 2.89–2.98 (2H, m), 3.77–3.92 (4H, m), 6.87 (1H, d, J=8.0Hz), 7.21–7.29 (2H, m), 9.87 (1H, brs).

Example of Preparation of Tablets-1

By using an usual procedure, tablets having the following formulation were prepared.

| | |
|---|---|
| 6-[4-(3-Phenyl-3-hydroxyiminopropyl)-1-piperazinylcarbonyl]-3,4-dihydrocarbostyril | 5 mg |
| Starch | 132 mg |
| Magnesium stearate | 18 mg |
| Lactose | 45 mg |
| Total | 200 mg |

Example of Preparation of Tablets-2

By using an usual procedure, tablets having the following formulation were prepared.

| | |
|---|---|
| 6-[4-(3-Phenyl-3-methylaminopropyl)-1-piperazinylcarbonyl]-3,4-dihydrocarbostyril dicitrate | 10 mg |
| Starch | 127 mg |
| Magnesium stearate | 18 mg |
| Lactose | 45 mg |
| Total | 200 mg |

Example of Preparation of Tablets-3

By using an usual procedure, tablets having the following formulation were prepared.

| | |
|---|---|
| 6-[4-(3-Phenyl-3-pyrrolidinyl)-1-piperazinylcarbonyl]-3,4-dihydrocarbostyril dicitrate | 5 mg |
| Starch | 132 mg |
| Magnesium stearate | 18 mg |
| Lactose | 45 mg |
| Total | 200 mg |

Example of Preparation of Tablets-4

By using an usual procedure, tablets having the following formulation were prepared.

| | |
|---|---|
| 6-{4-[3-(3,4-Dimethoxyphenyl)-3-hydroxyiminopropyl]-1-piperazinylcarbonyl}-3,4-dihydrocarbostyril | 5 mg |
| Starch | 132 mg |
| Magnesium stearate | 18 mg |
| Lactose | 45 mg |
| Total | 200 mg |

Example of Preparation of Tablets-5

By using an usual procedure, tablets having the following formulation were prepared.

| | |
|---|---|
| 6-[4-(N-Benzyl-N-methylamino)-1-piperidylcarbonyl]-3,4-dihydrocarbostyril | 5 mg |
| Starch | 132 mg |
| Magnesium stearate | 18 mg |
| Lactose | 45 mg |
| Total | 200 mg |

Example of Preparation of Injection-1

| | |
|---|---|
| 6-{1-Hydroxyimino-2-[N-methyl-N-(4-methoxybenzyl)amino-]butyl}-carbostyril | 500 mg |
| Polyethylene glycol (Molecular weight: 4,000) | 300 mg |
| Sodium chloride | 900 mg |
| Polyoxyethylene sorbitan monooleate | 400 mg |
| Sodium metabisulfite | 100 mg |
| Methyl p-hydroxybenzoate | 180 mg |
| Propyl p-hydroxybenzoate | 20 mg |
| Distilled water for injection | 100 ml |

Above prescribed methyl p-hydroxybenzoate, propyl p-hydroxybenzoate, sodium chloride and sodium metabisulfite were dissolved in about a half the quantity of distilled water at 80° C. with stirring. The obtained solution was cooled to 40° C., and 6-{1-hydroxyimino-2-[N-methyl-N-(4-methoxybenzyl)amino]butyl}carbostyril, polyethylene glycol and polyoxyethylene sorbitan monooleate were dissolved in this order in said solution. To this solution was further added distilled water for injection to the final regulated volume and then sterilized by sterile filtration with a suitable filter paper. One milliliter each of the obtained solution was filled in an ampoule separately to make injection preparations.

Example of Preparation of Injection-2

| | |
|---|---|
| 6-[4-(3-Phenyl-3-hydroxyiminopropyl)-1-piperazinylcarbonyl]-3,4-dihydrocarbostyril | 500 mg |
| Polyethylene glycol (Molecular weight: 4,000) | 300 mg |
| Sodium chloride | 900 mg |
| Polyoxyethylene sorbitan monooleate | 400 mg |
| Sodium metabisulfite | 100 mg |
| Methyl p-hydroxybenzoate | 180 mg |
| Propyl p-hydroxybenzoate | 20 mg |
| Distilled water for injection | 100 ml |

Above prescribed methyl p-hydroxybenzoate, propyl p-hydroxybenzoate, sodium chloride and sodium metabisulfite were dissolved in about a half the quantity of distilled water at 80° C. with stirring. The obtained solution was cooled to 40° C., and 6-[4--(3-phenyl-3-hydroxyiminopropyl)-1-piperazinylcarbonyl]-3,4-dihydrocarbostyril, polyethylene glycol and polyoxyethylene sorbitan monooleate were dissolved in this order in said solution. To this solution was further added distilled water for injection to the final regulated volume and then sterilized by sterile filtration with a suitable filter paper. One milliliter each of the obtained solution was filled in an ampoule separately to make injection preparations.

Example of Preparation of Injection-3

| | |
|---|---|
| 6-[4-(N-Benzyl-N-methylamino)-1-piperidylcarbonyl]carbostyril | 500 mg |
| Polyethylene glycol (Molecular weight: 4,000) | 300 mg |
| Sodium chloride | 900 mg |
| Polyoxyethylene sorbitan monooleate | 400 mg |
| Sodium metabisulfite | 100 mg |
| Methyl p-hydroxybenzoate | 180 mg |
| Propyl p-hydroxybenzoate | 20 mg |
| Distilled water for injection | 100 ml |

Above prescribed methyl p-hydroxybenzoate, propyl p-hydroxybenzoate, sodium chloride and sodium metabisulfite were dissolved in about a half the quantity of distilled water at 80° C. with stirring. The obtained solution was cooled to 40° C., and 6-[4-(N-benzyl-N-methylamino)-1-piperidylcarbonyl]carbostyril, polyethylene glycol and polyoxyethylene sorbitan monooleate were dissolved in this order in said solution. To this solution was further added distilled water for injection to the final regulated volume and then sterilized by sterile filtration with a suitable filter paper. One milliliter each of the obtained solution was filled in an ampoule separately to make injection preparations.

Pharmacological Test

Pharmacological activities of compounds of the general formula (1) and (101) of the present invention were conducted by test method as explained below with the results as follows.

1) Test Compounds

| Compound No. | |
|---|---|
| 1. | 6-[4-(3-Acetyloxyimino-3-phenyl)-1-piperazinylcarbonyl]-3,4-dihydrocarbostyril oxalate |
| 2. | 6-[4-(4-Cyano-4-phenylbutyl)-1-piperazinylcarbonyl]-3,4-dihydrocarbostyril monohydrochloride |
| 3. | 6-[4-(3-Hydroxyimino-3-phenylpropyl)-1-piperazinylcarbonyl]-3,4-dihydrocarbostyril semihydrate |
| 4. | 6-{1-Hydroxyimino-2-[N-methyl-N-(4-methoxybenzyl)amino]butyl}carbostyril |
| 5. | 6-(4-Benzylamino-1-piperidyl)-3,4-dihydrocarbostyril dihydrochloride hydrate |
| 6. | 6-(4-Ethoxycarbonylamino-1-piperidyl)-3,4-dihydrocarbostyril |
| 7. | 6-(4-Amino-1-piperidyl)-3,4-dihydrocarbostyril dihydrochloride semihydrate |
| 8. | 6-(4-Methylamino-1-piperidyl)-3,4-dihydrocarbostyril dihydrochloride hydrate |
| 9. | 6-(4-Dimethylamino-1-piperidylcarbonyl)-3,4-dihydrocarbostyril dicitrate |

-continued

| Compound No. | |
|---|---|
| 10. | 6-{4-[N-(2-Phenoxyethyl)-N-methylamino]-1-piperidylcarbonyl}-3,4-dihydrocarbostyril hydrochloride sesquihydrate |
| 11. | 6-[4-(N-Benzyl-N-methylamino)-1-piperidylcarbonyl]carbostyril |
| 12. | 6-[1-(2-Phenylthioethyl)-4-piperidylamido]-3,4-dihydrocarbostyril |
| 13. | 6-{1-[2-(N-Methyl-N-phenyl)ethyl]-4-piperidylamido}-3,4-dihydrocarbostyril semihydrate |
| 14. | 6-[1-(4-Methoxybenzyl)-4-piperidylamido]-3,4-dihydrocarbostyril semihydrate |
| 15. | 6-[1-(2,6-Dichlorobenzyl)-4-piperidylamido]-3,4-dihydrocarbostyril semihydrate |
| 16. | 6-[N-(1-Benzyl-4-piperidyl)-N-methylamido]-3,4-dihydrocarbostyril semihydrate |
| 17. | 6-{N-[1-(2-Phenylthioethyl)-4-piperidyl]-N-methylamido-}3,4-dihydrocarbostyril hydrochloride |
| 18. | 6-[N-{1-[2-(N-Methyl-N-phenyl)ethyl]-4-piperidyl}-N-methylamido]-3,4-dihydrocarbostyril hydrochloride. |
| 19. | 6-[N-(1-Benzoylmethyl-4-piperidyl)-N-methylamido]-3,4-dihydrocarbostyril hydrochloride |
| 20. | 6-{N-[1-(2-Hydroxy-2-phenylethyl)-4-piperidyl]-N-methylamido}-3,4-dihydrocarbostyril hydrochloride quaterhydrate |
| 21. | 6-[N-(1-Benzyl-4-piperidyl)-N-ethylamido]-3,4-dihydrocarbostyril hydrochloride |
| 22. | 6-[4-(N-Ethyl-N-benzylamino)-1-piperidylcarbonyl]-3,4-dihydrocarbostyril |
| 23. | 6-[N-(1-Isobutyl-4-piperidyl)-N-methylamido]-3,4-dihydrocarbostyril hydrochloride quaterhydrate |
| 24. | 6-[4-(N-Benzyl-N-methylamino)-1-piperidylcarbonyl]-3,4-dihydrocarbostyril |
| 25. | 6-[N-(1-Cinnamyl-4-piperidyl)-N-ethylamido]-3,4-dihydrocarbostyril hydrochloride |
| 26. | 6-{N-[1-(2-Phenoxyethyl)-4-piperidyl]-N-ethylamido}-3,4-dihydrocarbostyril hydrochloride |

2) Test Method

An adult mongrel dog of either sex, weighing 8-13 kg, was anesthetized with sodium pentobarbital at a rate of 30 mg/kg by intraveneous administration. After another intraveneous administration of sodium heparin at a rate of 1,000 U/kg, the test dog was killed by blood letting. The heart of the test dog was excised and the preparation was essentially consisting of the anterior papillary muscle and the venticular septum. The preparation was perfused, through the cannulated anterior septal artery, with the blood from a donor dog at a constant pressure of 100 mm-Hg. The dog used as donor was weighing 18-27 kg, and was anesthetized with pentobarbital sodium at a rate of 30 mg/kg by intraveneous administration, and further treated with intraveneous administration of sodium heparin at a rate of 1,000 U/kg. The papillary muscle was stimulated by applying a rectangular pulse of about 1.5 times the threshold voltage (i.e., 0.5–3 volts) for 5 milliseconds duration at a fixed rate of 120 beats/minute through a biplor pacing electrode. The papillary muscle was loaded with a weight of about 1.5 g, and the tension developed by the papillary muscle was measured by a train-gauge transducer. The blood flow through the anterior septal artery was measured by an electromagnetic flow meter. The developed tension and the blood flow were recorded on charts by using ink-writing rectigraph recorders. The details of this test method is reported in an article written by Endoh and Hashimoto:

"American Journal of Physiology," 218, pp. 1459–1463, (1970).

Each of the test compounds was intraarterially administered in an amount of 10 to 30 1 in 4 seconds.

The inotropic effect of each of the test compounds is expressed as a percentage of the developed tension before the intraarterial administration of each of the test compounds.

The effect of change of the blood flow in coronary artery of each of the test compounds is expressed as a difference of the absolute values (ml/minute) of before and after the intraarterial injection of each of the test compounds.

The test results are shown in Table 8 as follows:

TABLE 8

| Test Compound No. | Dosage (mol.) | Change of Contriction of Venticular muscle (%) | Change of Blood Flow in Coronary artery (ml/minute) |
| --- | --- | --- | --- |
| 1 | 1 | 74 | 5.9 |
| 2 | 1 | 48 | 8.0 |
| 3 | 1 | 77 | 3.5 |
| 4 | 1 | 42.1 | 2.6 |
| 5 | 1 | 21 | 1.4 |
| 6 | 1 | 27 | 1.3 |
| 7 | 1 | 66 | — |
| 8 | 1 | 54 | — |
| 9 | 1 | 24.6 | 2.1 |
| 10 | 1 | 21 | 3.1 |
| 11 | 1 | 43.5 | 1.3 |
| 12 | 1 | 27.0 | 1.0 |
| 13 | 1 | 38.7 | 2.5 |
| 14 | 1 | 29 | — |
| 15 | 1 | 31 | 2.6 |
| 16 | 1 | 57 | 2.3 |
| 17 | 1 | 73 | 6 |
| 18 | 1 | 28 | 4.3 |
| 19 | 1 | 33 | 4.6 |
| 20 | 1 | 21 | 5.4 |
| 21 | 1 | 37 | 4.3 |
| 22 | 1 | 44 | 4.8 |
| 23 | 1 | 16.5 | 2.1 |
| 24 | 1 | 40.7 | 2.3 |
| 25 | 1 | 35 | 4.1 |

TABLE 8-continued

| Test Compound No. | Dosage (mol.) | Change of Contriction of Venticular muscle (%) | Change of Blood Flow in Coronary artery (ml/minute) |
| --- | --- | --- | --- |
| 26 | 1 | 206.3 | 4.1 |

What is claimed is:

1. A carbostyril compound or salt thereof of the formula

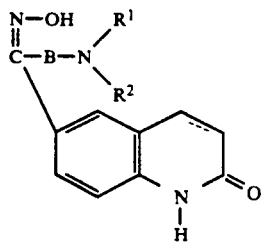

wherein B is a $C_1$–$C_6$ alkylene group; $R^1$ and $R^2$ are each the same or different and are each a $C_1$–$C_6$ alkyl group or a phenyl-$C_1$–$C_6$ alkyl group which may have from 1 to 2 $C_1$–$C_6$ alkoxy groups as substituents on the phenyl ring; and the carbon-carbon bond between the 3- and 4-positions in the carbostyril skeleton is a single or double bond.

2. The carbostyril compound or salt thereof of claim 1, wherein $R^1$ is a $C_1$–$C_6$ alkyl group and $R^2$ is a phenyl-$C_1$–$C_6$ alkyl group which may have from 1 to 2 $C_1$–$C_6$ alkoxy groups as substituents on the phenyl ring.

3. The carbostyril compound or salt thereof of claim 2, wherein the carbon-carbon bond between 3- and 4-positions in the carbostyril skeleton is a double bond.

4. The carbostyril compound or salt thereof of claim 2, wherein the carbon-carbon bond between 3- and 4-positions in the carbostyril skeleton is a single bond.

5. 6-{1-Hydroxyimino-2[N-methyl-N-(4-methoxybenzyl)amino]butyl}carbostyril.

6. A cardiotonic composition comprising an effective amount of a carbostyril compound or a pharmaceutically acceptable salt thereof of claim 1 as the active ingredient and a pharmaceutically acceptable carrier.

* * * * *